(12) United States Patent
Kalaj et al.

(10) Patent No.: US 11,795,505 B2
(45) Date of Patent: Oct. 24, 2023

(54) NUCLEIC ACID DELIVERY SCAFFOLDS

(71) Applicant: Singular Genomics Systems, Inc., San Diego, CA (US)

(72) Inventors: Mark Kalaj, San Diego, CA (US); Daan Witters, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/119,393

(22) Filed: Mar. 9, 2023

(65) Prior Publication Data

US 2023/0287491 A1    Sep. 14, 2023

Related U.S. Application Data

(60) Provisional application No. 63/402,741, filed on Aug. 31, 2022, provisional application No. 63/341,258, filed on May 12, 2022, provisional application No. 63/318,616, filed on Mar. 10, 2022.

(51) Int. Cl.
*C12Q 1/6874* (2018.01)

(52) U.S. Cl.
CPC .................................. *C12Q 1/6874* (2013.01)

(58) Field of Classification Search
None
See application file for complete search history.

(56) References Cited

U.S. PATENT DOCUMENTS

| | | | |
|---|---|---|---|
| 4,318,846 A | 3/1982 | Khanna et al. |
| 4,882,245 A | 11/1989 | Gelorme et al. |
| 4,970,276 A | 11/1990 | Das et al. |
| 5,034,506 A | 7/1991 | Summerton et al. |
| 5,066,580 A | 11/1991 | Lee |
| 5,188,934 A | 2/1993 | Menchen et al. |
| 5,235,033 A | 8/1993 | Summerton et al. |
| 5,366,860 A | 11/1994 | Bergot et al. |
| 5,599,675 A | 2/1997 | Brenner |
| 5,688,648 A | 11/1997 | Mathies et al. |
| 5,750,341 A | 5/1998 | Macevicz |
| 5,763,594 A | 6/1998 | Hiatt et al. |
| 5,800,996 A | 9/1998 | Lee et al. |
| 5,808,045 A | 9/1998 | Hiatt et al. |
| 5,847,162 A | 12/1998 | Lee et al. |
| 5,872,244 A | 2/1999 | Hiatt et al. |
| 6,232,465 B1 | 5/2001 | Hiatt et al. |
| 6,258,568 B1 | 7/2001 | Nyren |
| 6,274,320 B1 | 8/2001 | Rothberg et al. |
| 6,897,012 B2 | 5/2005 | Hada et al. |
| 6,991,888 B2 | 1/2006 | Padmanaban et al. |
| 7,057,026 B2 | 6/2006 | Barnes et al. |
| 7,291,395 B2 | 11/2007 | Pohl et al. |
| 7,467,632 B2 | 12/2008 | Lee et al. |
| 7,541,444 B2 | 6/2009 | Milton et al. |
| 8,003,354 B2 | 8/2011 | Shen et al. |
| 8,039,817 B2 | 10/2011 | Feng et al. |
| 8,178,360 B2 | 5/2012 | Barnes et al. |
| 8,241,573 B2 | 8/2012 | Banerjee et al. |
| 10,738,072 B1 | 8/2020 | Graham et al. |
| 2008/0000373 A1 | 1/2008 | Petrucci-Samija et al. |
| 2010/0160478 A1 | 6/2010 | Nilsson et al. |
| 2011/0059865 A1 | 3/2011 | Smith et al. |
| 2012/0009267 A1 | 1/2012 | Cho et al. |
| 2012/0270305 A1 | 10/2012 | Reed et al. |
| 2013/0178787 A1 | 7/2013 | Klem et al. |
| 2015/0079351 A1 | 3/2015 | Atasoy et al. |
| 2016/0256846 A1 | 9/2016 | Smith et al. |
| 2017/0022553 A1 | 1/2017 | Vijayan et al. |
| 2018/0258472 A1 | 9/2018 | Glezer |
| 2018/0274024 A1 | 9/2018 | Ju et al. |
| 2018/0311378 A1 | 11/2018 | Mitragotri et al. |
| 2019/0046943 A1 | 2/2019 | Barnard et al. |
| 2019/0048404 A1 | 2/2019 | Dambacher |
| 2021/0040555 A1 | 2/2021 | Glezer et al. |
| 2021/0190668 A1 | 6/2021 | Kovacs et al. |
| 2021/0262018 A1 | 8/2021 | Bava et al. |
| 2022/0042087 A1 | 2/2022 | Glezer et al. |

FOREIGN PATENT DOCUMENTS

| | | |
|---|---|---|
| WO | WO-1989/010977 A1 | 11/1989 |
| WO | WO-1996/007669 A1 | 3/1996 |
| WO | WO-2003/081202 A2 | 10/2003 |
| WO | WO-2004/018497 A3 | 6/2004 |
| WO | WO-2003/081202 A3 | 7/2004 |
| WO | WO-2006/029517 A1 | 3/2006 |
| WO | WO-2017/143075 A1 | 8/2017 |
| WO | WO-2017/205336 A1 | 11/2017 |
| WO | WO-2018/148723 A1 | 8/2018 |
| WO | WO-2020/014708 A1 | 1/2020 |
| WO | WO-2020/056044 A1 | 3/2020 |

OTHER PUBLICATIONS

US-PCT/US2022/075197, not yet published, Singular Genomics Systems, Inc.
Bains, W. et al. (Dec. 7, 1988). "A novel method for nucleic acid sequence determination," *Journal of Theoretical Biology* 135(3): 303-307.
Bentley, D. R. et al. (Nov. 6, 2008, e-published May 6, 2009). "Accurate whole human genome sequencing using reversible terminator chemistry," *Nature* 456(7218): 53-59.
Brenner, S. et al. (Jun. 2000). "Gene expression analysis by massively parallel signature sequencing (MPSS) on microbead arrays," *Nature biotechnology* 18(6): 630-634.
Cohen, S. M. (2012). "Postsynthetic methods for the functionalization of metal-organic frameworks," *Chemical reviews* 112(2): 970-1000.
Devaraj, N. K. et al. (Jun. 23, 2021). "Introduction: click chemistry," *Chemical Reviews* 121(12): 6697-6698.
Drmanac, S. et al. (Jan. 1, 1998). "Accurate sequencing by hybridization for DNA diagnostics and individual genomics," *Nature Biotechnology* 16(1): 54-58.

(Continued)

*Primary Examiner* — Teresa E Strzelecka
(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are degradable nanoparticles, nanoarrays, and methods of use thereof in nucleic acid sequencing.

30 Claims, 10 Drawing Sheets

(56) References Cited

OTHER PUBLICATIONS

Feeney, R. E. et al. (Apr. 1, 1982, e-published Jul. 22, 2009). "Chemical modification of proteins: An overview," *Advances in Chemistry Series* 182: 3-55.

Fodor, S. P. A. et al. (Feb. 15, 1991). "Light-directed, spatially addressable parallel chemical synthesis," *Science* 251(4995): 767-773.

Furukawa, H. et al. (Aug. 30, 2013). "The chemistry and applications of metal-organic frameworks," *Science* 341(6149): Article 1230444.

Haas, K.-H. et al. (Aug. 30, 1999, e-published Sep. 2, 1999). "Functionalized coating materials based on inorganic-organic polymers," *Thin Solid Films* 351(1-2): 198-203.

Hein, C. D. et al. (Oct. 2008, e-published May 29, 2008). "Click chemistry, a powerful tool for pharmaceutical sciences," *Pharmaceutical research* 25: 2216-2230.

Kato, M. et al. (Feb. 1, 1995, e-published May 1, 2002) "Polymerization of methyl methacrylate with the carbon tetrachloride/dichlorotris-(triphenylphosphine) ruthenium (II)/methylaluminum bis (2, 6-di-tert-butylphenoxide) initiating system: possibility of living radical polymerization," *Macromolecules* 28(5): 1721-1723.

Larsson, C. et al. (Apr. 11, 2010). "In situ detection and genotyping of individual mRNA molecules," *Nature methods* 7(5): 395-397.

Moad, G. et al. (Jun. 14, 2005) "Living radical polymerization by the RAFT process," *Australian journal of chemistry* 58(6): 379-410.

Otsu, T. et al. (Feb. 16, 1982). "Role of initiator-transfer agent-terminator (iniferter) in radical polymerizations: Polymer design by organic disulfides as iniferters," *Die Makromolekulare Chemie, Rapid Communications* 3(2): 127-132.

Ronaghi, M. et al. (Nov. 1, 1996). "Real-time DNA sequencing using detection of pyrophosphate release," *Analytical Biochemistry* 242(1): 84-89.

Ronaghi, M. et al. (Jul. 17, 1998). "A sequencing method based on real-time pyrophosphate," *Science* 281(5375): 363-365.

Ronaghi, M. (Jan. 2001). "Pyrosequencing sheds light on DNA sequencing," *Genome Research* 11(1): 3-11.

Shendure, J. et al. (Sep. 9, 2005, e-published Aug. 4, 2005). "Accurate multiplex polony sequencing of an evolved bacterial genome," *Science* 309(5741):1728-1732.

Veregin, R. P. N. et al. (Sep. 1, 1993). "Free radical polymerizations for narrow polydispersity resins: electron spin resonance studies of the kinetics and mechanism," *Macromolecules* 26(20): 5316-5320.

Walt, D. R. (Jan. 21, 2000). "Bead-based fiber-optic arrays," *Science* 287(5452): 451-452.

Wang, J-S. et al. (May 1, 1995, e-published May 1, 2002). "Controlled/"living" radical polymerization. atom transfer radical polymerization in the presence of transition-metal complexes," *Journal of the American Chemical Society* 117(20): 5614-5615.

Yeole, N. (May 2010). "Thiocarbonylthio compounds," *Synlett* 2010(10): 1572-1573.

York, A. G. et al. (Nov. 2013, e-published Oct. 6, 2013). "Instant super-resolution imaging in live cells and embryos via analog image processing," *Nature Methods* 10(11): 1122-1126.

Zhang, D. et al. (Nov. 13, 2018). "Preparation and surface properties study of novel fluorine-containing methacrylate polymers for coating," *Materials* 11(11): Article 2258.

Zhou, H-C. et al. (Feb. 8, 2012, e-published Jan. 26, 2012). "Introduction to metal-organic frameworks," *Chemical reviews* 112(2): 673-674.

Invitation to Pay Additional Fees dated May 22, 2023, for PCT application PCT/US2023/014871, filed Mar. 9, 2023, 2 pages.

International Search Report and Written Opinion dated Aug. 24, 2023, for PCT application PCT/US2023/014871, filed Mar. 9, 2023, 18 pages.

Wu, Q. et al. (Apr. 2018, e-published Feb. 9, 2018). "Biocompatible and biodegradable zeolitic imidazolate framework/polydopamine nanocarriers for dual stimulus triggered tumor thermo-chemotherapy," *Biomaterials* 162: 132-143.

Yu, L. et al. (Feb. 25, 2015). "Mitigated reactive oxygen species generation leads to an improvement of cell proliferation on poly [glycidyl methacrylate-co-poly (ethylene glycol) methacrylate] functionalized polydimethylsiloxane surfaces," *Journal of Biomedical Materials Research Part A* 103(9): 2987-2997.

Degradable particle core;
diameter about 500 nm

Degradable particle core + shell;
diameter about 600 nm to about 900 nm

NUCLEIC ACID DELIVERY SCAFFOLDS

CROSS-REFERENCES TO RELATED APPLICATIONS

This application claims the benefit of U.S. Provisional Application No. 63/318,616, filed Mar. 10, 2022, U.S. Provisional Application No. 63/341,258, filed May 12, 2022, and U.S. Provisional Application No. 63/402,741, filed Aug. 31, 2022, each which are incorporated herein by reference in their entirety and for all purposes.

BACKGROUND

Arrays are an important tool in biomedical research, providing a platform that arranges biological samples and enables high-throughput analyses. Delivering breakthroughs in proteomics, multiplexed immunoassays, and complex genomic analyses, arrays (e.g., microarrays and nanoarrays) can be designed to host thousands, millions, or even billions, of features that are subjected to simultaneous reaction conditions. Next generation sequencing (NGS) methodologies make use of simultaneously sequencing millions of fragments of nucleic acids in a single experiment. For example, sequencing-by-synthesis (SBS) is typically performed by imaging clusters of amplicons, referred to as features, each having multiple identical copies of a target polynucleotide. In order to maximize the rate of output of sequencing information, efforts have been made to increase the ratio of nucleotides sequenced per image. Miniaturization is required for increasing the scale and density of the clusters, that could result in lower reagent consumption and faster data acquisitions, however greater challenges arise as the feature dimensions approach submicron domains. Disclosed herein, inter alia, are solutions to these and other problems in the art.

BRIEF SUMMARY

In an aspect is provided a particle including a degradable particle core; a polymer shell surrounding the particle core; wherein the polymer shell includes a plurality of polymerized units of shell monomers and one or more shell monomers includes an oligonucleotide moiety covalently linked to the shell monomer.

In an aspect is a particle including a degradable particle core; a polymer shell surrounding the degradable particle core; and a plurality of oligonucleotide moieties covalently attached to the particle via a polymeric bioconjugate linker. In embodiments, the polymer shell includes a plurality of polymerized units of shell monomers and a plurality of oligonucleotide moieties wherein each oligonucleotide moiety is covalently attached to the polymer shell via a bioconjugate linker. In embodiments, the polymeric bioconjugate linker is the product of a reaction between the two bioconjugate groups (e.g., two complementary click-chemistry groups). In embodiments, the polymeric bioconjugate linker is formed between a first reactive moiety and a second reactive moiety as described herein.

In an aspect is provided a plurality of particles wherein each particle is as described herein. In embodiments, each particle of the plurality of particles has the same oligonucleotide moiety covalently linked to each shell monomer. In embodiments, each particle of the plurality of particles can have different oligonucleotide moieties covalently linked to each shell monomer.

In an aspect is provided a method of attaching a polymer composition to a solid support, the method including contacting a solid support including two or more wells with the plurality of particles as described herein, including embodiments, thereby depositing the one or more particles in a well; contacting the one or more particles with a degrading agent thereby decomposing the degradable particle core and forming a polymer composition attached to the well. In embodiments, the polymer composition includes a plurality of polymerized units of shell monomers wherein one or more shell monomers includes an oligonucleotide moiety covalently linked to the shell monomer. In embodiments, this method further includes hybridizing a biomolecule to the oligonucleotide and detecting the biomolecule, thereby detecting the oligonucleotide. In further embodiments, the oligonucleotide moiety is capable of hybridizing to a complementary sequence of a template nucleic acid.

BRIEF DESCRIPTION OF THE DRAWINGS

FIG. 1A depicts a scanning electron micrograph of a subsection of an array having particles containing a MOF carrier core (avg. diameter 350 nm), wherein the core is coated in a polymeric shell containing polynucleotides covalently linked to the polymer shell. FIG. 1B depicts scanning electron micrograph of the same array following an alkaline (e.g., NaOH) wash that removes the MOF carrier core, leaving behind the polymeric shell. FIG. 1C shows a fluorescent image of the array following hybridization of a complementary florescent probe to the polynucleotides in the polymer after dissolving the MOF carrier core. The brighter spots show where more polynucleotides, and hence originally particles, were loaded into the well.

FIG. 4A is an illustration of functionalized particle including a degradable particle core (e.g., a MOF carrier) and a polymer shell. The illustration depicts the polymer shell as distinct polymeric chains with exaggerated separation for clarity. However, it is understood that the polymer chains may form a network that coat (i.e., surround) the surface of the particle core. Additives may be added to crosslink the linear polymer chains. The thickness of the polymer layer can be controlled by varying the reaction conditions (e.g., time, temperature, and concentration of the corresponding monomers) to provide a thickness of about 50 nm to about 200 nm. FIG. 4B illustrates an embodiment of individual polymeric chain covalently attached to the particle core. The polymer chain is a polyethylene glycol methacrylate (PEGMA) and glicydyl methacrylate azide (GMA azide, or GMA-Az) copolymer in a 2:1 ratio (i.e., having an ng of 3). Alternative ng copolymers were also synthesized by varying the ratio of PEGMA:GMA-Az 5:1 (ng=6) or 8:1 (ng=9), providing tunable parameters to control the density of oligonucleotide, which corresponds to density of the resulting polynucleotides. Only a single polymer is depicted, however it is understood that the solid support includes a plurality of polymers to form a polymer shell, as illustrated in FIG. 4A. FIG. 4C illustrates an example of a polymeric bioconjugate linker being formed between a polymer shell (e.g., a polymer shell attached to a solid support) with a first bioconjugate reactive moiety (i.e., an azide) and an oligonucleotide with a second bioconjugate reactive moiety (i.e., DBCO).

FIG. 6A describes synthesized MOF particles were functionalized through post-synthetic exchange (PSE), followed by atom-transfer radical polymerization (ATRP) to result in a polymer coating around the MOF particle (i.e., formation of the polymer shell). FIG. 6B provides additional details for forming polymer shells around a MOF particle. ZIF-8 MOF particles are treated with an ATRP initiator (e.g., Histamine-BiB) to form a functionalized ZIF-8-BiB particle that undergoes polymerization with monomers of PEGMA and GMA-azide to form a degradable particle core and a polymer shell attached to the degradable particle core. A tunable parameter to modulate the polymer thickness and molecular weight is the number of PEG units within the PEGMA monomer (e.g., by modulating n). In embodiments, n is an integer between 1 and 48. In embodiments, n is an integer between 1 and 12.

Figure 1A:
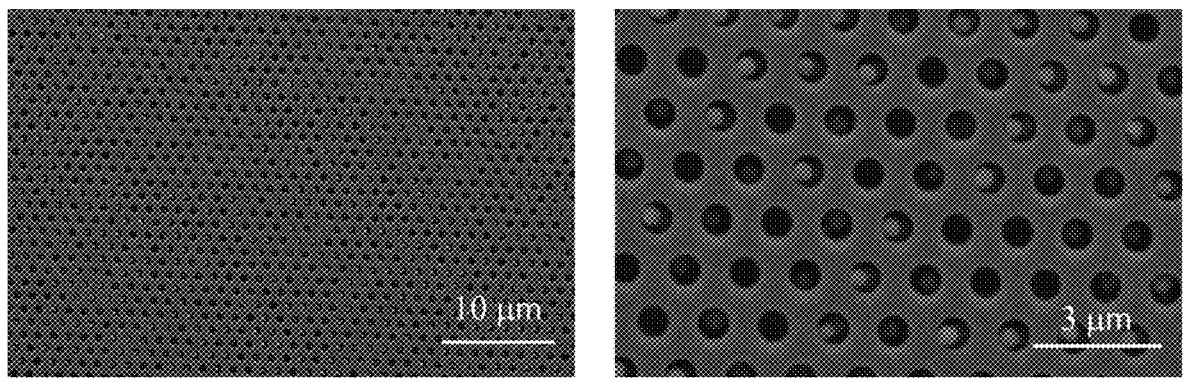
FIGS. 1A-1C provide images of a patterned array containing particles loaded into the wells.

For example, oligonucleotides containing reactive bioconjugate moieties (e.g., primers containing a DBCO moiety on the 5' end) are introduced under suitable conditions such that a polymeric bioconjugate linker forms between the reactive bioconjugate moieties of the oligonucleotides and the bioconjugate reactive moieties attached to the polymer shell.

DETAILED DESCRIPTION

I. Definitions

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The terms "attached," "bind," and "bound" as used herein are used in accordance with their plain and ordinary meanings and refer to an association between atoms or molecules. The association can be direct or indirect. For example, attached molecules may be directly bound to one another, e.g., by a covalent bond or non-covalent bond (e.g. electrostatic interactions (e.g., ionic bond, hydrogen bond, halogen bond, metal coordination bond), van der Waals interactions (e.g., dipole-dipole, dipole-induced dipole, London dispersion), ring stacking (pi effects), hydrophobic interactions, and the like). As a further example, two molecules may be bound indirectly to one another by way of direct binding to one or more intermediate molecules, thereby forming a complex.

As used herein, the term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. Another example of complementary sequences are a template sequence and an amplicon sequence polymerized by a polymerase along the template sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, one or both sequences in a pair of complementary sequences form portions of longer polynucleotides, which may or may not include additional regions of complementarity.

As used herein, the term "hybridize" or "specifically hybridize" refers to a process where two complementary nucleic acid strands anneal to each other under appropriately stringent conditions. Hybridizations are typically and preferably conducted with oligonucleotides. Non-limiting examples of nucleic acid hybridization techniques are described in, for example, Sambrook, et al., Molecular Cloning: A Laboratory Manual (2nd Edition, 1989). Those skilled in the art understand how to estimate and adjust the stringency of hybridization conditions such that sequences having at least a desired level of complementarity will stably hybridize, while those having lower complementarity will not. Hybridization reactions can be performed under conditions of different "stringency". For example, a low stringency hybridization reaction is carried out at about 40° C. in 10×SSC. A moderate stringency hybridization may be performed at about 50° C. in 6×SSC. A high stringency hybridization reaction is generally performed at about 60° C. in 1×SSC. Hybridization reactions can also be performed under "physiological conditions" which is well known to one of skill in the art (e.g., a physiological condition is the temperature, ionic strength, pH and concentration of $Mg^{2+}$ normally found in vivo). The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55. ° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which includes a double stranded portion of nucleic acid.

As used herein, the term "stringent condition" refers to condition(s) under which a polynucleotide probe or primer will hybridize preferentially to its target sequence, and to a lesser extent to, or not at all to, other sequences. A "stringent hybridization" and "stringent hybridization wash conditions" in the context of nucleic acid hybridization are sequence dependent, and are different under different environmental parameters.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer.

Polynucleotides useful in the methods of the disclosure may include natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "polynucleotide template" or "template nucleic acid" refers to any polynucleotide molecule that may be bound by a polymerase and utilized as a template for nucleic acid synthesis. As used herein, the term "polynucleotide primer" refers to any polynucleotide molecule that may hybridize to a polynucleotide template, be bound by a polymerase, and be extended in a template-directed process for nucleic acid synthesis, such as in a PCR or sequencing reaction. A primer can be of any length depending on the particular technique it will be used for. For example, PCR primers are generally between 10 and 40 nucleotides in length. The length and complexity of the nucleic acid fixed onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

As used herein, the term "analogue", in reference to a chemical compound, refers to a compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as primers attached to a polymer. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH═CH$_2$), methoxyalkyl (e.g., —CH$_2$—O—CH$_3$), or —CH$_2$N$_3$. In embodiments, the blocking moiety is attached to the 3' oxygen of the nucleotide and is independently

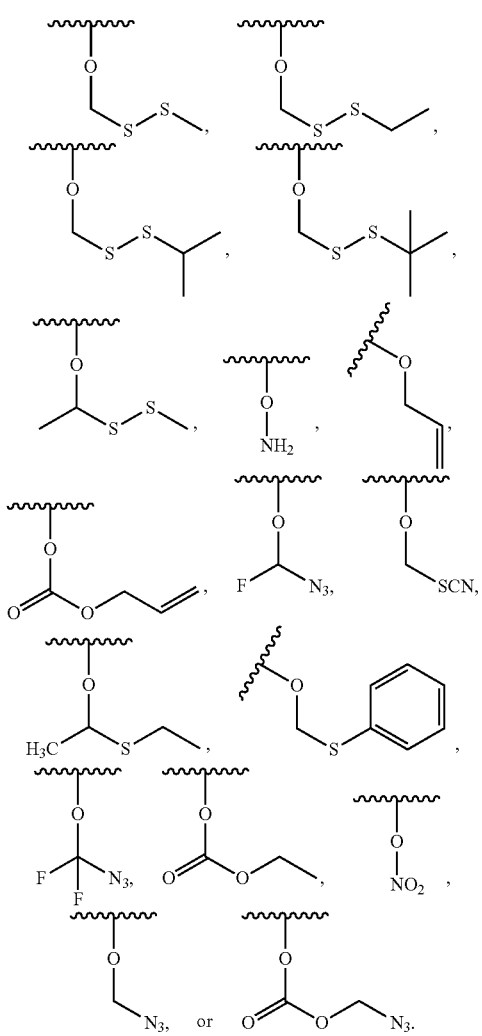

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogs include, without limitation, 7-deaza-adenine, 7-deaza-guanine, the analogs of deoxynucleotides shown herein, analogs in which a label is attached through a cleavable linker to the 5-position of cytosine or thymine or to the 7-position of deaza-adenine or deaza-guanine, and analogs in which a small chemical moiety is used to cap the —OH group at the 3'-position of deoxyribose. As used herein, the terms "blocking moiety," "reversible blocking group," "reversible terminator" and "reversible terminator moiety" are used in accordance with their plain and ordinary meanings and refer to a cleavable moiety which does not interfere with incorporation of a nucleotide including it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein O is the oxygen atom of the 3'-OH of the pentose and R is the blocking group, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is

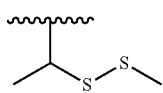 [SMILES: *C(C)SSC]

as described in U.S. Pat. No. 10,738,072, which is incorporated herein by reference for all purposes. In embodiments, the reversible terminator moiety is

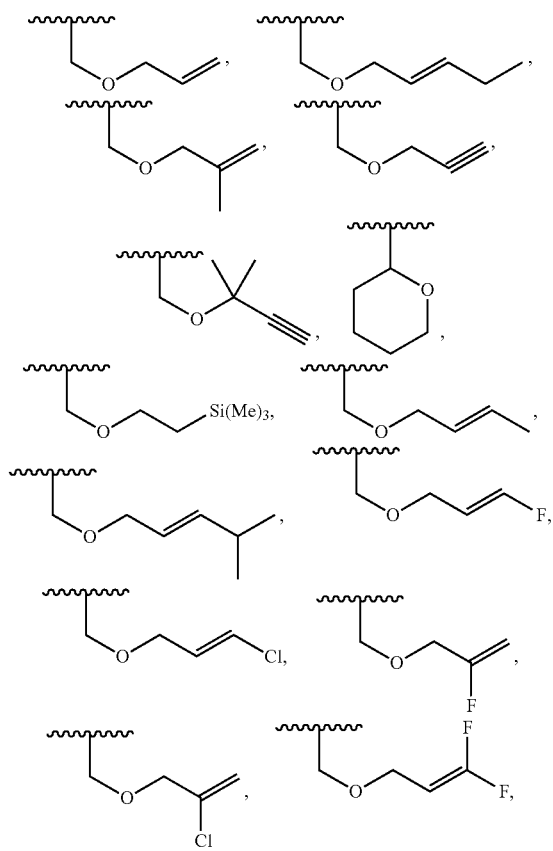

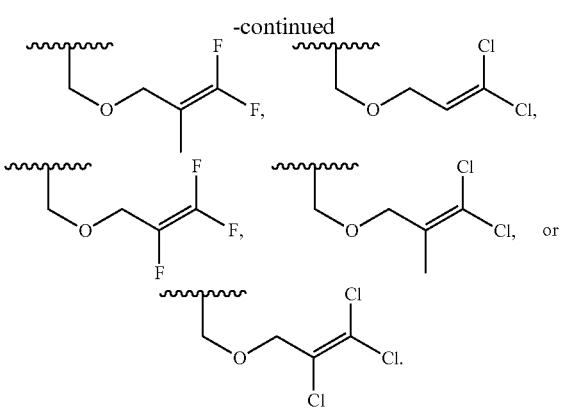

The terms "particle" and "bead" are used interchangeably and mean a small body made of a rigid or semi-rigid material. The body can have a shape characterized, for example, as a sphere, oval, microsphere, or other recognized particle shape whether having regular or irregular dimensions. As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid.

As used herein, the term "discrete particles" refers to physically distinct particles having discernible boundaries. Discrete particles collected in a container and contacting one another will define a bulk volume containing the particles, and will typically leave some internal fraction of that bulk volume unoccupied by the particles, even when packed closely together.

A "nanoparticle," as used herein, is a particle wherein the longest diameter is less than or equal to 1000 nanometers. Nanoparticles may be composed of any appropriate material. Nanoparticles may be composed of at least two distinct materials, one material (e.g., the MOF carrier) forms the core and the other material forms the shell (e.g., copolymer) surrounding the core. In embodiments, the nanoparticle is composed of a copolymer described herein. In embodiments, a nanoparticle has a shortest diameter greater than or equal to 1 nanometer (e.g., diameter from 1 to 1000 nanometers). In contrast to a functionalized particle, an unmodified particle refers to a particle which has not been further functionalized. Thus, for example, an unmodified particle does not include a nitrogen containing moiety (e.g., terminal amine moieties). For example, an unmodified nanoparticle refers to nanoparticle as synthesized without post hoc functionalization. As used herein, the terms "bare particle" and "unmodified particle" are synonymous and interchangeable.

A functionalized particle, as used herein, may refer to the post hoc conjugation (i.e. conjugation after the formation of the particle) of a moiety to a functional group on the surface of a particle. For example, a particle may be further functionalized to include additional atoms (e.g., nitrogen) or chemical entities (e.g., polymeric moieties or bioconjugate group).

Lengths and sizes of nanoparticles and functionalized particles as described herein may be measured using Transmission Electron Microscopy. For example, transmission electron microscopy measurements of the various particle samples may be drop coated (5 μL) onto 200 mesh copper EM grids, air-dried and imaged using a FEI Tecnai 12 TEM equipped with a Gatan Ultrascan 2K CCD camera at an accelerating voltage of 120 kV. The average size distributions of the particles may then be obtained from the TEM images using Image J software that were plotted using software (e.g., Origin Pro 8) to obtain the histogram size distributions of the particles. In embodiment, the length of a nanoparticle refers to the longest dimension of the particle.

The particle includes a degradable particle core, referred to as a "core" and polymer shell surrounding the core. The core may be referred to herein as a nanoparticle core wherein the longest diameter is less than 1000 nanometers. Lengths and sizes of particles and their surrounding cores as described herein may be measured using Transmission Electron Microscopy (TEM). In embodiments, the cores and/or polymer shells of the particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a particle) refers to the average thickness of the polymer layer.

As used herein, the term "degradable particle core" refers to carrier scaffold onto which a polymer is attached, and that is surrounded by a "shell polymer" to which polynucleotide primers may or may not be attached to the shell polymer. The presence of the polynucleotide primer on the shell polymer surrounding the core permits a nucleic acid amplification reaction to take place. In embodiments, the cores are "surrounded" by the shell polymer in the sense that the shell polymer completely covers each core, and no core is in direct contact with any other core. The shell layer may enclose (e.g., surround, encapsulate, envelope) a core. In embodiments, each core surrounded by the shell polymer forms a discrete particle, the outer surface of which is defined by the shell polymer. In embodiments, the shells of discrete core-shell particles suspended in a container (e.g., a well, tube, or flow cell) expands, to fill any space between adjacent particles. In such cases, the boundaries of individual particles may no longer be readily discernable, but each core remains separated from each other by the shell polymer surrounding each, which can be readily observed by, e.g., detecting products of a nucleic acid amplification reaction. The shell polymer may itself surround a degradable particle core. The core can include a variety of materials, including but not limited to a polymer, inorganic material, or hybrid of organic-inorganic material, such as a metal-organic framework (MOF carrier). The degradable particle core may be a hydrophobic particle core made through emulsion or latex. In embodiments, the degradable particle core is a MOF carrier such as Zeolitic Imidazolate Framework (e.g., ZIF-8). In embodiments, the degradable particle core is a hydrophobic particle such as polystyrene (PS) or polymethyl methacrylate (PMMA). The degradable particle core, may be referred to herein as a nanoparticle core wherein the longest diameter is less than 1,000 nanometers. Lengths and sizes of particles and their surrounding cores as described herein may be measured using Transmission Electron Microscopy (TEM). In embodiments, the degradable particle core includes a plurality of oligonucleotide moieties covalently attached to the degradable particle core particle via a polymeric bioconjugate linker. In embodiments, the bioconjugate linker is formed via a reaction between a particle polymer (i.e., a shell polymer) including a first bioconjugate reactive moiety and an oligonucleotide including a second bioconjugate reactive moiety. In embodiments, the degradable particle core is porous. In embodiments the term "degradable particle core" refers to a particle of rigid or semi-rigid material that degrades, disintegrates, and/or dissolves upon contact with a degrading agent. A degradable particle core may include an initial shape, or occupy a characteristic volume in three dimensional space, and following contact with the degrading agent, the shape is changed or diminished. For example, a spherical degradable particle may be a spherical upon deposition to the solid support, and following contact with a degrading agent the degradable particle includes an amorphous shape. In embodiments, the degrading agent breaks the bonds of the degradable particle core. In embodiments, following decomposition, the degradable particle core breaks apart into particle components. In embodiments, the particle components do not react (i.e., do not covalently bind) to the polymer shell. In embodiments, the particle components are capable of being removed and/or washed away from the polymer shell.

The term "carrier scaffold" refers to a rigid three-dimensional structure and functions to retain the shape of the degradable particle core and the polymer shell. Following contact with a degrading agent, the carrier scaffold loses the ability to retain the shape of the degradable particle core.

The terms "shell polymer" and "polymer shell" are used interchangeably and refer to a polymer attached to a particle described herein. In embodiments, the polymer shell includes a plurality of polymerized monomers. In embodiments, the polymer shell encapsulates or envelops the degradable particle core forming a layer around the degradable particle core. In embodiments, the polymer shell conforms to the shape of the underlying degradable particle core. For example, if the degradable particle core is approximately spherical the surrounding polymer shell is spherical. In embodiments, the polymer shell is a brush polymer. In embodiments, the polymer shell is a linear polymer. In embodiments, the polymer shell is a coating. In embodiments, the polymer shell is a continuous polymer layer. In embodiments, the polymer shell is permeable to a degrading agent. In embodiments, the polymer shell includes a plurality of linear polymers, wherein each linear polynomial is attached to the degradable particle core. Following decomposition or dissolution of the degradable particle core, the polymer shell forms a polymer film (e.g., forms a polymer film composition at the location where the degradable particle was previously located). In embodiments, the polymer shell is covalently attached to the degradable particle core, for example via an ATRP initiator such as His-BiB. In embodiments, following decomposition of the degradable particle core at a location, the polymer shell is capable of forming a polymer film at the location.

As used herein, the term "MOF" is used in accordance with its ordinary meaning in the art and refers to a metal-organic framework. A MOF is a type of porous material comprised of metal containing nodes and organic ligands linked through coordination bonds. The structure and topology of MOFs can be designed and tailored so that the MOF can form one-, two-, or three-dimensional structures. The modular nature of MOFs allows for great synthetic tunability so properties such as porosity, stability, particle morphology and conductivity can be tailored for specific applications including encapsulation or release of guest molecules. The organic ligands used in MOFs are also referred to as "linkers" and are typically mono-, di-, tri-, or tetravalent ligands. The choice of metal and linker dictates the structure and properties of the MOF. For example, the metal's coordination preference can influence the size and shape of the pores in the MOF through the metal's preference for number and orientation of binding ligands. A MOF typically has potential voids between the organic ligands which make them valuable in applications such as drug delivery, bio-storage and bio-catalysis. Further MOFs can undergo post-synthetic modification to further tune properties through swapping, altering or removing linker or node components in the framework. The MOF can be modified using a "modulator" or "modulating agent". The modulator competes with the organic linkers to bind to the metal center. In doing so, this prevents formation of impurities and slows down the reaction, allowing for increased reproducibility and crystallinity of the final product. Compounds that can act as modulators include but are not limited to CTAB, 1-methylimidazole, sodium formate and n-butylamine. Additional modulators include cationic surfactants, such as cetyltrimethylammonium chloride (CTAC), stearalkonium chloride, quaternium-15, quaternium-18, benzalkonium chloride, benzethonium chloride, polyquaternium-7, polyquaternium-10, dodecyltrimethylammonium chloride (DTAC), and hexadecyltrimethylammonium chloride (HTAC).

A MOF can be degraded to release the compound(s) and/or material(s) encapsulated by the MOF. A MOF can be degraded in response to changes in pH, temperature, or light. Examples of MOF structures are zinc imidazolate framework (e.g., ZIF-8), Zr based MOFs, mesoporous iron (III) carboxylate MIL-100(Fe). In embodiments, the metal organic framework is a crystalline compound comprising metal ions coordinated to rigid organic molecules to form one-, two-, or three-dimensional structures that are highly porous. Other MOFs that can be used include those described in Furukawa et al. (see Science, vol. 341, No. 6149, 1230444, 2013) or Cohen (see Chem. Reviews, Vol. 112, No. 2, p. 970-1000, 2012). MOF particles may be functionalized using reversible addition-fragmentation chain transfer polymerization (RAFT) in which chain-transfer agents (CTA) are used to form polymer-coated MOFs in a controlled fashion. For example, a catechol-bound chain-transfer agent (CTA) can be used to graft poly(methyl methacrylate) (PMMA) onto the surface of the MOF, thereby functionalizing the particle for additional polymerization. Controlled polymerization of MOF surfaces can also be performed by surface functionalization of MOFs (e.g. UiO-66(Zr), UiO-66(Zr)—$NH_2$ and MIL-88B(Fe)—$NH_2$) with catechol-modified chain-transfer agents (cat-CTAs) followed by surface-initiated reversible addition-fragmentation chain transfer (SI-RAFT) polymerization of methyl methacrylate, resulting in polymer brush coated MOF particles.

As used herein, the term "ZIF-8" refers to a zeolitic imidazolate framework, which is a type of MOF. A ZIF-8 is composed of metal cation $Zn^{2+}$ linked to the 2-methylimidazolate ligand species. On-demand release of material (i.e., controlled degradation) from a ZIF-8 carrier occurs in the presence of an external stimulus such as increased pH and at high efficiency (up to 100%) and/or at high temperature conditions. In embodiments, ZIF-8 may be degraded by reducing the pH with an acid such as HCl, or by raising the pH with a base such as NaOH, and/or in the presence of degrading compounds such as phosphate, thereby eroding or dissolving the MOF.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can include natural or synthetic polymers. In some embodiments, the hydrogel polymer includes 60-90% fluid, such as water, and 10-30% polymer. In certain embodiments, the water content of hydrogel is about 70-80%.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO—PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO).

The term "array" as used herein, refers to a container (e.g., a multiwell container, reaction vessel, or flow cell) including a plurality of features (e.g., wells). For example, an array may include a container with a plurality of wells. In embodiments, the array is a microplate. In embodiments, the array is a flow cell.

The term "microplate," "microtiter plate," or "multiwell plate" as used herein, refers to a substrate including a surface, the surface including a plurality of chambers or wells separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins, or polynucleotides in a cell.

The reaction chambers may be provided as wells, for example an array or microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples.

The terms "iniferter mediated polymerization" and the like refer, in the usual and customary sense, to polymerization employing an "iniferter" which, as known in the art, is a chemical compound that simultaneously acts as initiator, transfer agent, and terminator in controlled free radical polymerization reactions, e.g., dithiocarbamates. See e.g., Otsu, T., & Yashida, M., Mackromol. *Chem., Rapid Commun.,* 1982, 3:127-132.

The terms "stable free radical mediated polymerization," "SRFP" and the like refer, in the usual and customary sense, to polymerization reactions wherein the coupling of the stable free radical with the polymeric radical is sufficiently reversible that the termination step is reversible, and the propagating radical concentration can be limited to levels that allow for controlled polymerization. See e.g., Veregin, R. P. N., et al., *Macromolecules* 1993, 26:5316-5320.

The terms "atom transfer radical polymerization," "ATRP" and the like refer, in the usual and customary sense, to methods of polymerization employing a transition metal catalyst, wherein the atom transfer step is the key step in the reaction responsible for uniform polymer chain growth. See e.g., Kato, M., et al., *Macromolecules* 1995, 28:1721-1723; Wang, J. & Matyjaszewski, K., *J. Am. Chem. Soc.* 1995, 117:5614-5615. Typical polymerization begins with an ATRP initiator in combination with polymerizable monomers. ATRP initiators include an alkyl halide (e.g., Cl or Br), as found in 2-bromopropanitrile, ethyl 2-bromoisobutyrate, ethyl 2-bromopropionate, methyl 2-bromopropionate, 1-phenyl ethylbromide, tosyl chloride, 1-cyano-1-methylethyldiethyldithiocarbamte, 2-(N,N-diethyldithiocarbamyl)-isobutyric acid ethyl ester, or dimethyl 2,6-dibromoheptanedioate. Typical polymerization begins with an ATRP initiator in combination with polymerizable monomers. ATRP initiators include an alkyl halide (e.g., Cl or Br), as found in 2-bromopropanitrile, ethyl 2-bromoisobutyrate, ethyl 2-bromopropionate, methyl 2-bromopropionate, 1-phenyl ethylbromide, tosyl chloride, 1-cyano-1-methylethyldiethyldithiocarbamte, 2-(N,N-diethyldithiocarbamyl)-isobutyric acid ethyl ester, or dimethyl 2,6-dibromoheptanedioate.

The terms "reversible addition fragmentation chain transfer polymerization," "RAFT" and the like refer, in the usual and customary sense, to methods of polymerization which use a chain transfer agent in the form of a thiocarbonylthio compound or the like to afford control over the generated molecular weight and polydispersity during a free-radical polymerization. See e.g., Yeole, N., *Synlett.* 2010(10): 1572-1573; Moad, G., et al., *Aust. J. Chem.,* 2005, 58:379-410.

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. In particular embodiments, a channel can be located in a flow cell, for example, being embedded within the flow cell. A channel in a flow cell can include one or more windows that are transparent to light in a particular region of the wavelength spectrum. In embodiments, the channel contains one or more polymers of the disclosure. In embodiments, the channel is filled by the one or more polymers, and flow through the channel (e.g., as in a sample fluid) is directed through the polymer in the channel. In embodiments, the assay is in a channel of a flow cell.

As used herein, the term "substrate" refers to a solid support material. The substrate can be non-porous or porous. The substrate can be rigid or flexible. As used herein, the terms "solid support" and "solid surface" refers to discrete solid or semi-solid surface. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A nonporous substrate generally provides a seal against bulk flow of liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located within a flow cell. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of the particle (e.g., see FIG. 2C) to maximize the contact between as substantially circular particle. In embodiments, the wells of an array are randomly located such that nearest neighbor features have random spacing between each other. Alternatively, in embodiments the spacing between the wells can be ordered, for example, forming a regular pattern. The term solid substrate is encompassing of a substrate (e.g., a flow cell) having a surface including a polymer coating covalently attached thereto. In embodiments, the solid substrate is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate includes a surface (e.g., a surface of a flow cell, a surface of a tube, a surface of a chip), for example a metal surface (e.g., steel, gold, silver, aluminum, silicon and copper). In embodiments a substrate (e.g., a substrate surface) is coated and/or includes functional groups and/or inert materials. In certain embodiments a substrate includes a bead, a chip, a capillary, a plate, a membrane, a wafer (e.g., silicon wafers), a comb, or a pin for example. In some embodiments a substrate includes a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In embodiments a substrate includes a magnetic material (e.g., iron, nickel, cobalt, platinum, aluminum, and the like). In embodiments a substrate includes a magnetic bead (e.g., DYNABEADS®, hematite, AMPure XP). Magnets can be used to purify and/or capture nucleic acids bound to certain substrates (e.g., substrates including a metal or magnetic material). The flow cell is typically a glass slide containing small fluidic channels (e.g., a glass slide 75 mm×25 mm×1 mm having one or more channels), through which sequencing solutions (e.g., polymerases, nucleotides, and buffers) may traverse. Though typically glass, suitable flow cell materials may include polymeric materials, plastics, silicon, quartz (fused silica), Borofloat® glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength. Conversely, it may be desirable to select a material that does not pass radiation of a certain wavelength (e.g., being opaque, absorptive, or reflective). In embodiments, the material of the flow cell is selected due to the ability to conduct thermal energy. In embodiments, a flow cell includes inlet and outlet ports and a flow channel extending there between.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature or depression in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate may be available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells. In embodiments, a solid support is a flat surface with an array of nanometer-sized wells or reservoirs.

Figure 2A:
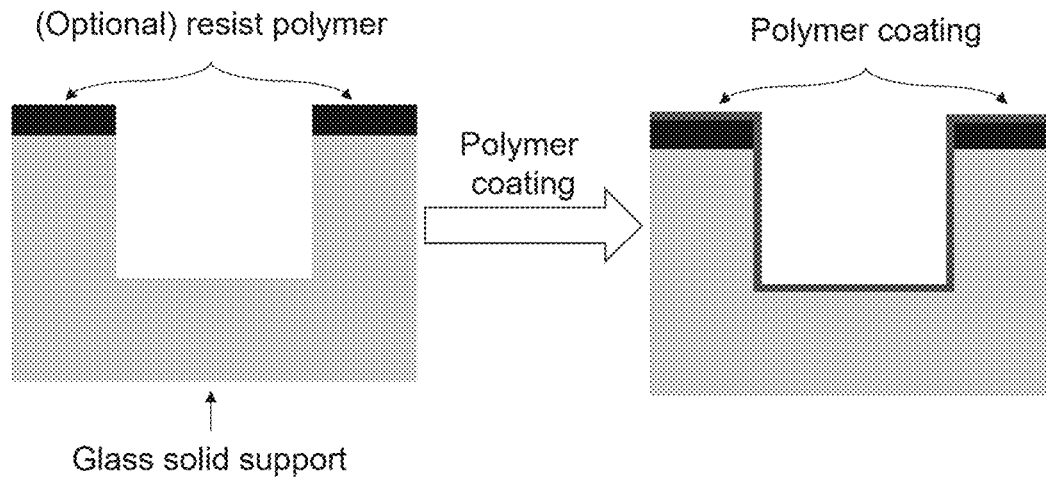
FIGS. 2A-2D. Illustrations of the different well shapes of the array. Using known nanolithographic fabrication techniques, a glass substrate may be etched such that the well is anisotropic (FIG. 2A), partially anisotropic (FIG. 2B), or isotropic (FIG. 2C). The array may include a photoresist (e.g., a fluorinated polymer layer). In embodiments, the wells and interstitial space may further include an additional polymer coating (e.g., a poloxamer or alkoxysilyl polymer coating). The photoresist may be removed prior to the addition of the additional polymer using known techniques in the art (e.g., solvent and/or physical removal of the photoresist). In embodiments, the additional polymer coating reduces the non-specific binding of oligonucleotide moieties. Alternatively, the wells may be directly formed within the resist (e.g., a nanoimprint resist) as depicted in FIG. 2D, wherein the resist is attached to a glass solid support. In embodiments, the resist is not removed prior to loading the particles.
Figure 2B:
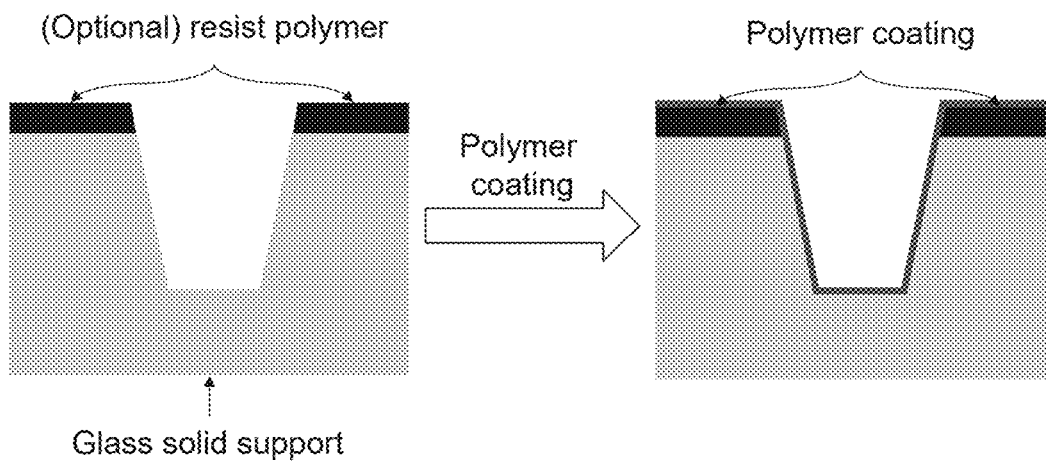
Figure 2C:
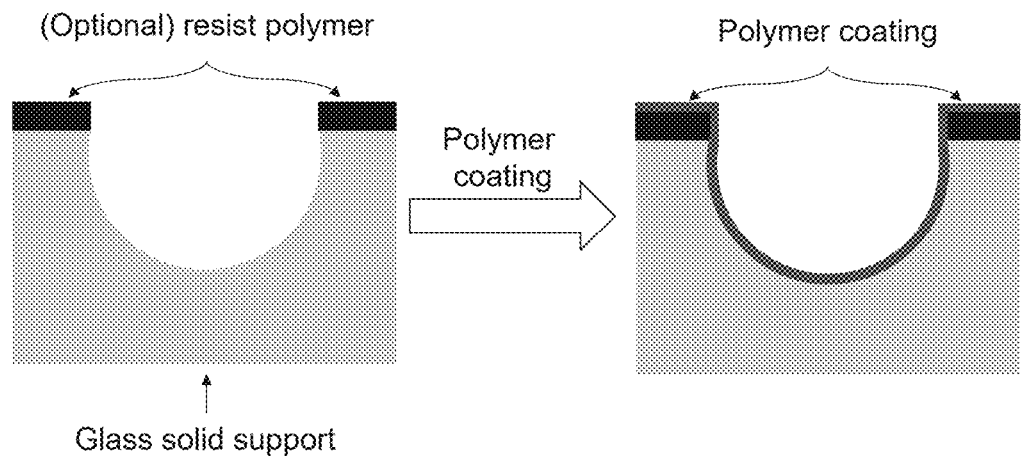

The discrete regions (i.e., features or wells) may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a passivating polymer or copolymer, as depicted in FIGS. 2A-2C). In embodiments, interstitial regions have a surface material that is the same as the surface material of the wells (e.g., both the surface of the interstitial region and the surface of well contain a polymer or copolymer).

As used herein, the term "feature" refers a point or area in a pattern that can be distinguished from other points or areas according to its relative location. An individual feature can include one or more polynucleotides. For example, a feature can include a single target nucleic acid molecule having a particular sequence or a feature can include several nucleic acid molecules having the same sequence (and/or complementary sequence, thereof). Different molecules that are at different features of a pattern can be differentiated from each other according to the locations of the features in the pattern. Non-limiting examples of features include wells in a substrate, particles (e.g., beads) in or on a substrate, polymers in or on a substrate, projections from a substrate, ridges on a substrate, or channels in a substrate.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. In embodiments, one nucleotide (e.g., a modified nucleotide) is incorporated per sequencing cycle. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes, and other substances can be removed between steps by washing. Cycles may include repeating these steps, and the sequence of each cluster is read over the multiple repetitions.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence.

In embodiments, a sequencing read includes reading a barcode and not a template nucleotide sequence. Reads of length 20-40 base pairs (bp) are referred to as ultra-short. Typical sequencers produce read lengths in the range of 100-500 bp. Read length is a factor which can affect the results of biological studies. For example, longer read lengths improve the resolution of de novo genome assembly and detection of structural variants. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label. In some embodiments, a sequencing read may include 500, 600, 700, 800, 900, 1,000, 1,100, 1,200, 1,300, 1,400, 1,500, or more nucleotide bases.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain.

Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in addition to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in addition to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'- and -R'C(O)$_2$-. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. A bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)w, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. A bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form (CH$_2$)$_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings. In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C1-C4)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom (s) are optionally quaternized. Thus, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. A 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "$\sim\!\sim$" denotes the point of attachment of a chemical moiety to the remainder of a molecule or chemical formula.

The term "oxo," as used herein, means an oxygen that is double bonded to a carbon atom.

The term "nucleophile" as used herein refers to a chemical group that is capable of donating electron density. All molecules or ions with a free pair of electrons or at least one pi bond can act as nucleophiles. The term "electrophile" as used herein refers to a chemical group that is capable of accepting electron density. An "electrophilic substituent", "electrophilic chemical moiety", or "electrophilic moiety" refers to an electron-poor chemical group, substituent, or moiety (monovalent chemical group), which may react with an electron-donating group, such as a nucleophile, by accepting an electron pair or electron density to form a bond.

The term "alkoxysilyl" as used herein refers to silicon atom covalently bound to one or more alkoxy groups. In embodiments, the alkoxysilyl moiety has the formula-$(R)_n$—Si(—O-alkyl)$_3$ moiety, wherein n is 1, 2, or 3 and R is an unsubstituted $C_1$-$C_6$ alkyl. When used in combination with a polymerizable monomer (e.g., acrylate, methacrylate, acrylamide), it is understood the polymerizable monomer is covalently linked to the alkoxysilyl moiety. For example, alkoxysilyl methacrylate has the formula

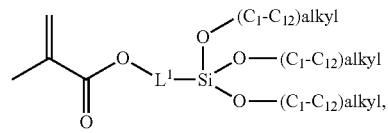

wherein $L^1$ is substituted or unsubstituted alkylene or substituted or unsubstituted heteroalkylene as described herein. In embodiments, alkoxysilyl acrylate has the formula

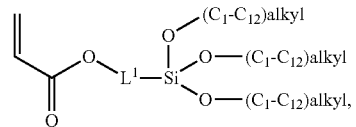

wherein $L^1$ is substituted or unsubstituted alkylene or substituted or unsubstituted heteroalkylene as described herein. In embodiments, alkoxysilyl methylacrylamide has the formula

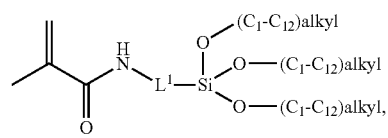

wherein $L^1$ is substituted or unsubstituted alkylene or substituted or unsubstituted heteroalkylene as described herein. In embodiments, alkoxysilyl acrylamide has the formula

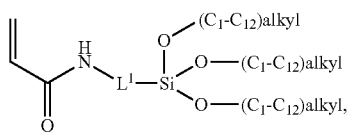

wherein $L^1$ is substituted or unsubstituted alkylene or substituted or unsubstituted heteroalkylene as described herein.

The term "alkylarylene" as an arylene moiety covalently bonded to an alkylene moiety (also referred to herein as an alkylene linker). In embodiments, the alkylarylene group has the formula:

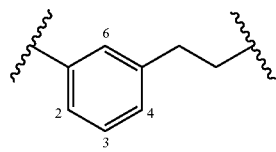

or

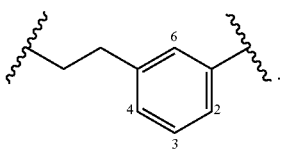

An alkylarylene moiety may be substituted (e.g., with a substituent group) on the alkylene moiety or the arylene linker (e.g., at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$, —SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: (a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g., $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g., $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$, ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g., $R^{1.3}$, $R^{2.3}$, $R^{3.3}$, $R^{4.3}$, $R^{5.3}$ ... $R^{100.3}$, $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.11}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

$R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)

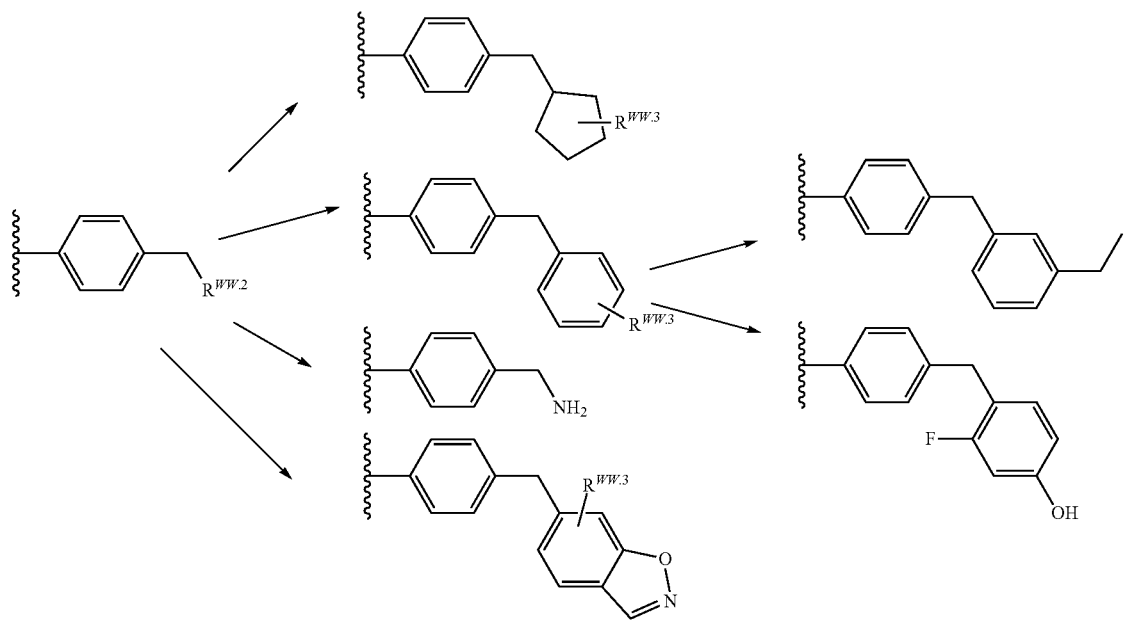

NH$_2$, —NHSO$_2$H, —NHC=(O)H, —NHC(O)—OH, —NHOH, —N$_3$, R$^{WW.3}$—substituted or unsubstituted alkyl (e.g., C$_1$-C$_8$, C$_1$-C$_6$, C$_1$-C$_4$, or C$_1$-C$_2$), R$^{WW.3}$—substituted or unsubstituted heteroalkyl (e.g., 2 to 8 membered, 2 to 6 membered, 4 to 6 membered, 2 to 3 membered, or 4 to 5 membered), R$^{WW.3}$—substituted or unsubstituted cycloalkyl (e.g., C$_3$-C$_8$, C$_3$-C$_6$, C$_4$-C$_6$, or C$_5$-C$_6$), R$^{WW.3}$—substituted or unsubstituted heterocycloalkyl (e.g., 3 to 8 membered, 3 to 6 membered, 4 to 6 membered, 4 to 5 membered, or 5 to 6 membered), R$^{WW.3}$—substituted or unsubstituted aryl (e.g., C$_6$-C$_{12}$, C$_6$-C$_{10}$, or phenyl), or R$^{WW.3}$—substituted or unsubstituted heteroaryl (e.g., 5 to 12 membered, 5 to 10 membered, 5 to 9 membered, or 5 to 6 membered). In embodiments, R$^{WW.2}$ is independently oxo, halogen, —CX$^{WW.2}_3$, —CHX$^{WW.2}_2$, —CH$_2$X$^{WW.2}$, —OCX$^{WW.2}_3$, —OCH$_2$X$^{WW.2}$, —OCHX$^{WW.2}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{WW.2}$ is independently —F, —Cl, —Br, or —I.

R$^{WW.3}$ is independently oxo, halogen, —CX$^{WW.3}_3$, —CHX$^{WW.3}_2$, —CH$_2$X$^{WW.3}$, —OCX$^{WW.3}_3$, —OCH$_2$X$^{WW.3}$, —OCHX$^{WW.3}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{WW.3}$ is independently —F, —Cl, —Br, or —I.

Where two different R$^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as R$^{WW.1}$; each first substituent group, R$^{WW.1}$, may be unsubstituted or independently substituted with one or more second substituent groups, referred to herein as R$^{WW.2}$; and each second substituent group, R$^{WW.2}$, may be unsubstituted or independently substituted with one or more third substituent groups, referred to herein as R$^{WW.3}$; and each third substituent group, R$^{WW.3}$, is unsubstituted. Each first substituent group is optionally different. Each second substituent group is optionally different. Each third substituent group is optionally different. In the context of two different R$^{WW}$ substituents joined together to form an openly substituted ring, the "WW" symbol in the R$^{WW.1}$, R$^{WW.2}$ and R$^{WW.3}$ refers to the designated number of one of the two different R$^{WW}$ substituents. For example, in embodiments where R$^{100A}$ and R$^{100B}$ are optionally joined together to form an openly substituted ring, R$^{WW.1}$ is R$^{100.1}$, R$^{WW.2}$ is R$^{100A.2}$, and R$^{WW.3}$ is R$^{100A.3}$. Alternatively, in embodiments where R$^{100A}$ and R$^{100B}$ are optionally joined together to form an openly substituted ring, R$^{WW.1}$ is R$^{100B.1}$, R$^{WW.2}$ is R$^{100B.2}$, and R$^{WW.3}$ is R$^{100B.3}$, R$^{WW.1}$, R$^{WW.2}$ and R$^{WW.3}$ in this paragraph are as defined in the preceding paragraphs.

R$^{LWW.1}$ is independently oxo, halogen, —CX$^{LWW.1}_3$, —CHX$^{LWW.1}_2$, —CH$_2$X$^{LWW.1}$, —OCX$^{LWW.1}_3$, —OCH$_2$X$^{LWW.1}$, —OCHX$^{LWW.1}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{LWW.2}$—substituted or unsubstituted alkyl (e.g., C$_1$-C$_8$, C$_1$-C$_6$, C$_1$-C$_4$, or C$_1$-C$_2$), R$^{LWW.2}$—substituted or unsubstituted heteroalkyl (e.g., 2 to 8 membered, 2 to 6 membered, 4 to 6 membered, 2 to 3 membered, or 4 to 5 membered), R$^{LWW.2}$—substituted or unsubstituted cycloalkyl (e.g., C$_3$-C$_8$, C$_3$-C$_6$, C$_4$-C$_6$, or C$_5$-C$_6$), R$^{LWW.2}$—substituted or unsubstituted heterocycloalkyl (e.g., 3 to 8 membered, 3 to 6 membered, 4 to 6 membered, 4 to 5 membered, or 5 to 6 membered), R$^{LWW.2}$—substituted or unsubstituted aryl (e.g., C$_6$-C$_{12}$, C$_6$-C$_{10}$, or phenyl), or R$^{LWW.2}$—substituted or unsubstituted heteroaryl (e.g., 5 to 12 membered, 5 to 10 membered, 5 to 9 membered, or 5 to 6 membered). In embodiments, R$^{LWW.1}$ is independently oxo, halogen, —CX$^{LWW.1}_3$, —CHX$^{LWW.1}_2$—CH$_2$X$^{LWW.1}$, —OCX$^{LWW.1}_3$—OCH$_2$X$^{LWW.1}$, —OCHX$^{LWW.1}_2$—CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). X$^{LWW.1}$ is independently —F, —Cl, —Br, or —I.

R$^{LWW.2}$ is independently oxo, halogen, —CX$^{LWW.2}_3$, —CHX$^{LWW.2}_2$, —CH$_2$X$^{LWW.2}$, —OCX$^{LWW.2}_3$, —OCH$_2$X$^{LWW.2}$, —OCHX$^{LWW.2}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{LWW.3}$—substituted or unsubstituted alkyl (e.g., C$_1$-C$_8$, C$_1$-C$_6$, C$_1$-C$_4$, or C$_1$-C$_2$), R$^{LWW.3}$—substituted or unsubstituted heteroalkyl (e.g., 2 to 8 membered, 2 to 6 membered, 4 to 6 membered, 2 to 3 membered, or 4 to 5 membered), R$^{WW.3}$—substituted or unsubstituted cycloalkyl (e.g., C$_3$-C$_8$, C$_3$-C$_6$, C$_4$-C$_6$, or C$_5$-C$_6$), R$^{LWW.3}$—substituted or unsubstituted heterocycloalkyl (e.g., 3 to 8 membered, 3 to 6 membered, 4 to 6 membered, 4 to 5 membered, or 5 to 6 membered), R$^{LWW.3}$—substituted or unsubstituted aryl (e.g., C$_6$-C$_{12}$, C$_6$-C$_{10}$, or phenyl), or R$^{LWW.3}$—substituted or unsubstituted heteroaryl (e.g., 5 to 12 membered, 5 to 10 membered, 5 to 9 membered, or 5 to 6 membered). In embodiments, R$^{LWW.2}$ is independently oxo, halogen, —CX$^{LWW.2}_3$, —CHX$^{LWW.2}_2$, —CH$_2$X$^{LWW.2}$, —OCX$^{LWW.2}_3$, —OCH$_2$X$^{LWW.2}$, —OCHX$^{LWW.2}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)

$NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently $-F$, $-Cl$, $-Br$, or $-I$.

$R^{LWW.3}$ is independently oxo, halogen, $-CX^{LWW.3}_3$, $-CHX^{LWW.3}_2$, $-CH_2X^{LWW.3}$, $-OCX^{LWW.3}_3$, $-OCH_2X^{LWW.3}$, $-OCHX^{LWW.3}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently $-F$, $-Cl$, $-Br$, or $-I$.

In the event that any R group recited in a claim or chemical formula description set forth herein ($R^{WW}$ substituent) is not specifically defined in this disclosure, then that R group ($R^{WW}$ group) is hereby defined as independently oxo, halogen, $-CX^{WW}_3$, $-CHX^{WW}_2$, $-CH_2X^{WW}$, $-OCX^{WW}_3$, $-OCH_2X^{WW}$, $-OCHX^{WW}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{WW.1}$—substituted or unsubstituted alkyl (e.g., $C_1$-$C_8$, $C_1$-$C_6$, $C_1$-$C_4$, or $C_1$-$C_2$), $R^{WW.1}$—substituted or unsubstituted heteroalkyl (e.g., 2 to 8 membered, 2 to 6 membered, 4 to 6 membered, 2 to 3 membered, or 4 to 5 membered), $R^{WW.1}$—substituted or unsubstituted cycloalkyl (e.g., $C_3$-$C_8$, $C_3$-$C_6$, $C_4$-$C_6$, or $C_5$-$C_6$), $R^{WW.1}$—substituted or unsubstituted heterocycloalkyl (e.g., 3 to 8 membered, 3 to 6 membered, 4 to 6 membered, 4 to 5 membered, or 5 to 6 membered), $R^{WW.1}$—substituted or unsubstituted aryl (e.g., $C_6$-$C_{12}$, $C_6$-$C_{10}$, or phenyl), or $R^{WW.1}$—substituted or unsubstituted heteroaryl (e.g., 5 to 12 membered, 5 to 10 membered, 5 to 9 membered, or 5 to 6 membered). $X^{WW}$ is independently $-F$, $-Cl$, $-Br$, or $-I$. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, $-O-$, $-NH-$, $-C(O)-$, $-C(O)NH-$, $-NHC(O)-$, $-NHC(O)NH-$, $-C(O)O-$, $-OC(O)-$, $-S-$, $-SO_2NH-$, $R^{LWW.1}$—substituted or unsubstituted alkylene (e.g., $C_1$-$C_8$, $C_1$-$C_6$, $C_1$-$C_4$, or $C_1$-$C_2$), $R^{LWW.1}$—substituted or unsubstituted heteroalkylene (e.g., 2 to 8 membered, 2 to 6 membered, 4 to 6 membered, 2 to 3 membered, or 4 to 5 membered), $R^{LWW.1}$—substituted or unsubstituted cycloalkylene (e.g., $C_3$-$C_8$, $C_3$-$C_6$, $C_4$-$C_6$, or $C_5$-$C_6$), $R^{LWW.1}$—substituted or unsubstituted heterocycloalkylene (e.g., 3 to 8 membered, 3 to 6 membered, 4 to 6 membered, 4 to 5 membered, or 5 to 6 membered), $R^{LWW.1}$—substituted or unsubstituted arylene (e.g., $C_6$-$C_{12}$, $C_6$-$C_{10}$, or phenyl), or $R^{LWW.1}$—substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.1}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium (3H), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby including another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^3A$, $R^{13B}$, $R^{13C}$, $R^{13D}$, etc. is defined within the scope of the definition of $R^{13}$ and optionally differently.

Descriptions of compounds (e.g., polymers) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccinimide,-maleimide,

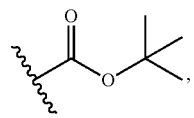 [SMILES: *C(=O)OC(C)(C)C]

or

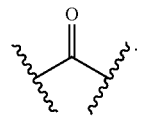

In embodiments, the bioconjugate reactive group may be protected (e.g., with a protecting group). In embodiments, the bioconjugate reactive moiety is —$N_3$,-DBCO, a norbornene moiety, alkynyl,

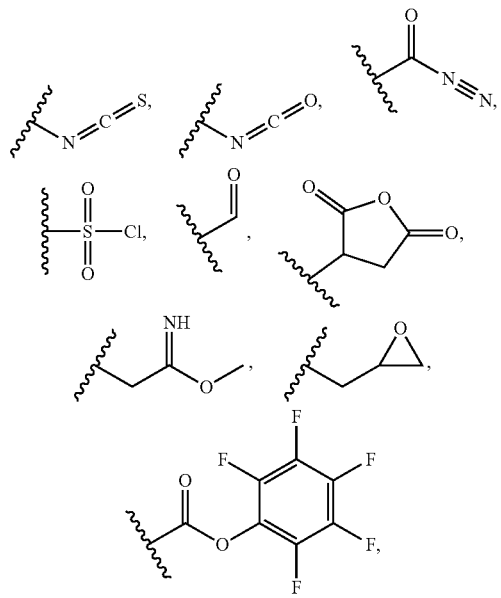

or —$NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate reactive moiety" and "bioconjugate reactive group" refers to a moiety or group capable of forming a bioconjugate linker (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g.,-sulfo-N-hydroxysuccinimide moiety) is covalently attached to the second bioconjugate reactive group (e.g., an amine). In embodiments, a bioconjugate linker is formed by the reaction between an azide moiety and a dibenzocyclooctyne (DBCO) moiety.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized;(i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds.; (n) azides coupled to alkynes using copper catalyzed cycloaddition click chemistry; (o) biotin conjugate can react with avidin or strepavidin to form a avidin-biotin complex or streptavidin-biotin complex.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "non-reactive moiety" is used in accordance with its plain ordinary meaning and refers to a moiety that does not react with a nucleophile or an electrophile (e.g., under reaction conditions wherein other moieties in the same molecule may react with a nucleophile or electrophile, under click chemistry reaction conditions such as those conditions wherein an azide may react with dibenzocyclooctyne (DBCO) or an epoxide). In embodiments, the non-reactive moiety is attached to a polymer. In embodiments, the non-reactive moiety is hydrophilic. In embodiments, the non-reactive moiety increases the water solubility of a polymer that includes the non-reactive moiety. In embodiments, the non-reactive moiety is not a bioconjugate reactive moiety. In embodiments, the non-reactive moiety is an unsubstituted alkyl. In embodiments, the non-reactive moiety is hydrogen.

"Contacting" is used in accordance with its plain ordinary meaning and refers to the process of allowing at least two distinct species (e.g., chemical compounds including biomolecules, particles, solid supports, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be an oligonucleotide and a polymer composition as described herein. In some embodiments contacting includes allowing a particle described herein to interact with an array.

As used herein, a "plurality" refers to two or more.

As used herein, "capable of hybridizing" is used in accordance with its ordinary meaning in the art and refers to two oligonucleotides that, under suitable conditions, can form a duplex (e.g., Watson-Crick pairing) which includes a double-stranded portion of nucleic acid. Such conditions, known in the art and described herein, depend upon, for example, the nature of the nucleotide sequence, temperature, and buffer conditions. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "Tm"; parameters such as salts, buffers, pH, temperature, GC % content of the polynucleotide and primers, and/or time. Typically, hybridization is favored in lower temperatures and/or increased salt concentrations, as well as reduced concentrations of organic solvents. Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher. In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer. In some embodiments, hybridization or wash conditions can be conducted at a pH range of about 5-10, or about pH 6-9, or about pH 6.5-8, or about pH 6.5-7.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

The term "adapter" as used herein refers to any linear oligonucleotide that can be ligated to a nucleic acid molecule, thereby generating nucleic acid products that can be sequenced on a sequencing platform (e.g., an Illumina or Singular Genomics sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., primer sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing.

As used herein, a "platform primer" is a primer oligonucleotide immobilized or otherwise bound to a solid support (i.e. an immobilized oligonucleotide). Examples of platform primers include P7 and P5 primers, or S1 and S2 sequences, or the reverse complements thereof. A "platform primer binding sequence" refers to a sequence or portion of an oligonucleotide that is capable of binding to a platform primer (e.g., the platform primer binding sequence is complementary to the platform primer). In embodiments, a platform primer binding sequence may form part of an adapter. In embodiments, a platform primer binding sequence is complementary to a platform primer sequence. In embodiments, a platform primer binding sequence is complementary to a primer. In embodiments, the oligonucleotide attached to the polymer shell is a platform primer or includes a platform primer sequence.

A "degrading agent" refers to an external stimulus agent (e.g., a substance) that when applied to a degradable particle core reduces the mass of the degradable particle core. In embodiments, the degrading agent is dissolved in a buffer. In embodiments, the degrading agent is a dissolving agent. For example, a degrading agent may dissolve the degradable particle core, permitting the structural elements that compose the degradable particle core to be removed. In embodiments, the degrading agent does not destroy, substantially damage, or substantially modify chemical or structural properties of the oligonucleotide, the polymer, or the bioconjugate reactive moiety. In embodiments, the degrading agent, when applied to the degradable particle core, causes the release of the polymer shell from the degradable particle core. In embodiments, the degrading agent, when applied to a particle including a degradable particle core surrounded by a polymer shell, releases the polymer shell from the degradable particle core, wherein a substantial amount of the degradable particle core is removed and the polymer shell remains at the location wherein the particles was located. In embodiments, a degrading agent breaks down the degradable particle core into smaller constituents capable of being removed (e.g., washed away from the location). The degrading agent may include a change in reaction conditions (e.g., elevated temperatures to 30° C., 40° C., 50° C., 60° C. or higher) relative to reaction conditions during deposition. In embodiments, contacting the degradable particle core with a degrading agent includes an increase in temperature. In embodiments, the degrading agent changes the shape of the degradable particle core. In embodiments, the degrading agent disrupts the bonds of the degradable particle core. In embodiments, the degrading agent binds to the components that compose the degradable particle core. In embodiments, the degrading agent transforms the shape of the particle from a defined shape to an amorphous shape. In embodiments, the degrading agent catalyzes acid-labile or base-labile bonds (e.g., ionic bonds and/or coordination bonding involving metal ions). In embodiments, the degrading agent breaks the coordination complexes of the degradable particle core.

A "pH-sensitive particle core" is a degradable particle core, wherein the carrier scaffold is stable at a neutral pH (e.g., pH of 7.0-7.4) and dissolves or is degraded upon a modulation in the pH (i.e., a deviation from neutral pH). A typical pH-sensitive particle core maintains a shape (e.g., spherical or cuboidal) at a first pH (e.g., 7.0) and loses the shape (e.g., becomes amorphous) at a second pH (e.g., 12.0). For example, the pH-sensitive particle core may swell, collapse, or dissolve depending on the pH of degrading agent. Poly(acrylic acid), poly(allylamine hydrochloride), and metal organic frameworks are non-limiting examples of materials known to be pH sensitive materials. Additional examples of pH sensitive nanoparticles may be found in Lee et al (J Control Release. 2008 Dec. 18; 132(3):164-70) and Zhou et al. (Angew Chem Int Ed Engl. 2011 Jun. 27; 50(27):6109-14), each of which are incorporated herein by reference. In embodiments, the pH sensitive particle core is a MOF core described herein. In embodiments, the pH sensitive core includes incorporation of compounds including cleavable bonds (e.g., imine, hydrazone, hydrazide, oxime, and (di)methyl maleate). An example of a pH-sensitive core is poly(L-histidine)-b-poly(ethylene glycol) (PH-PEG) combined with poly(L-lactic acid)-b-poly(ethylene glycol) (PLA-PEG). In embodiments, the pH-sensitive particle core is a salt particle.

An "acid" is used in accordance with its known meaning in the art and refers to a chemical species (e.g., molecule, ion, or aqueous solution) capable of donating a proton (i.e., a hydrogen ion) and/or accepts electrons. Common aqueous acids include hydrochloric acid, sulfuric acid, acetic acid, and citric acid. The higher the concentration of hydrogen ions produced by an acid, the higher its acidity and the lower the pH of the solution. An aqueous solution of an acid has a pH less than 7.0 and is also referred to as "acid." In embodiments, an acid is an aqueous solution having a pH less than 7.0. A "base" is used in accordance with its known meaning in the art and refers to a chemical species (e.g., molecule, ion, or aqueous solution) that donates electrons, accepts protons, or releases hydroxide (OH—) ions in aqueous solution. A base turns litmus paper blue, methyl orange yellow, and phenolphthalein pink. An aqueous solution of an acid has a pH greater than 7.0 and is also referred to as a "base." In embodiments, a base is an aqueous solution having a pH greater than 7.0. In embodiments, the acid or base may be in a buffered solution to maintain a pH. A buffer is a solution containing either a weak acid and its salt or a weak base and its salt, which is typically resistant to significant changes in pH. In embodiments, a buffer is an aqueous solution of either a weak acid and its conjugate base or a weak base and its conjugate acid.

The term "polish" is used in accordance with its ordinary meaning and refers to rubbing, cleaning, or grinding a surface.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is provided a particle including a degradable particle core; a polymer shell surrounding the particle core (e.g., a polymer shell that is attached to the particle core); wherein the polymer shell includes a plurality of polymerized units of shell monomers and one or more shell monomers includes an oligonucleotide moiety covalently linked to the shell monomer. In embodiments, the polymerized units of shell monomers may be referred to herein as a particle polymer. In embodiments, the oligonucleotide moiety is covalently linked to the particle polymer via a bioconjugate linker. In embodiments, the particle has an average longest dimension of the particle of about 100 nm to about 3000 nm. In embodiments, the average longest dimension of the degradable particle core is about 100 nm to about 3000 nm. In embodiments, the degradable particle core is a pH-sensitive particle core.

In an aspect is provided a particle including a degradable particle core; a polymer shell surrounding the particle core (e.g., a polymer shell that is attached to the particle core); wherein the polymer shell includes a plurality of polymerized units of shell monomers and one or more shell monomers includes a bioconjugate reactive moiety covalently linked to the shell monomer. In embodiments, the polymerized units of shell monomers may be referred to herein as a particle polymer or particle shell. In embodiments, the oligonucleotide moiety is covalently linked to the particle polymer via a bioconjugate linker (i.e., a reaction between a first bioconjugate reactive moiety and a second bioconjugate reactive moiety. In embodiments, the particle has an average longest dimension of the particle of about 100 nm to about 3000 nm. In embodiments, the average longest dimension of the degradable particle core is about 100 nm to about 3000 nm. In embodiments, the degradable particle core is a pH-sensitive particle core.

In an aspect is a particle including a degradable particle core; a polymer shell surrounding the degradable particle core; and a plurality of oligonucleotide moieties covalently attached to the particle via a polymeric bioconjugate linker. In embodiments, the polymer shell includes a plurality of polymerized units of shell monomers and a plurality of oligonucleotide moieties wherein each oligonucleotide moiety is covalently attached to the polymer shell via a bioconjugate linker. In embodiments, the polymeric bioconjugate linker is the product of a reaction between the two bioconjugate group (e.g., click chemistry group). In embodiments, the polymeric bioconjugate linker is formed between a first reactive moiety and a second reactive moiety as described herein. In embodiments, the degradable particle core is a pH-sensitive particle core.

In an aspect is provided a particle, wherein the particle includes a plurality of oligonucleotide moieties covalently attached to the particle via a polymeric bioconjugate linker. In embodiments, the particle includes a plurality of polymeric bioconjugate linkers. In embodiments, the bioconjugate linker is formed via a reaction between a particle polymer including a first bioconjugate reactive moiety and an oligonucleotide comprising a second bioconjugate reactive moiety. In embodiments, the particle polymer includes polymerized units of polyacrylamide (AAm), glicydyl methacrylate (GMA), glicydyl methacrylate (GMA) azide, polyethylene glycol methacrylate (PEGMA), polyethylene glycol methacrylate (PEGMA), isocyanatoethyl methacrylate (IEM), or a copolymer thereof. In embodiments, the first bioconjugate reactive moiety and the second bioconjugate reactive moiety is selected from the following: an amine moiety, azide moiety, alkyne moiety, dibenzocyclooctyne (DBCO) moiety, epoxy moiety, and isocyanate moiety. In embodiments, the degradable particle core is a pH-sensitive particle core.

In embodiments, each particle includes a plurality of oligonucleotide moieties covalently attached to said particle via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the average longest dimension of the particle is from about 100 nm to about 3000 nm. In embodiments, each particle includes a plurality of oligonucleotide moieties covalently attached to said particle via a bioconjugate linker, wherein the polymeric bioconjugate linker is formed through a reaction between a particle polymer (e.g., a polymer covalently attached to the surface of the particle) including a first bioconjugate reactive moiety (e.g., an azide) and an oligonucleotide including a second bioconjugate reactive moiety (e.g., DBCO). Bioconjugate reactive moieties are described herein, and for example further characterized and described in Hein et al (Pharm Res. 2008 October; 25(10): 2216-2230) and Devaraj and Finn (Chem. Rev. 2021, 121, 12, 6697-6698), both of which are each incorporated herein by reference in their entirety.

Figure 4A:
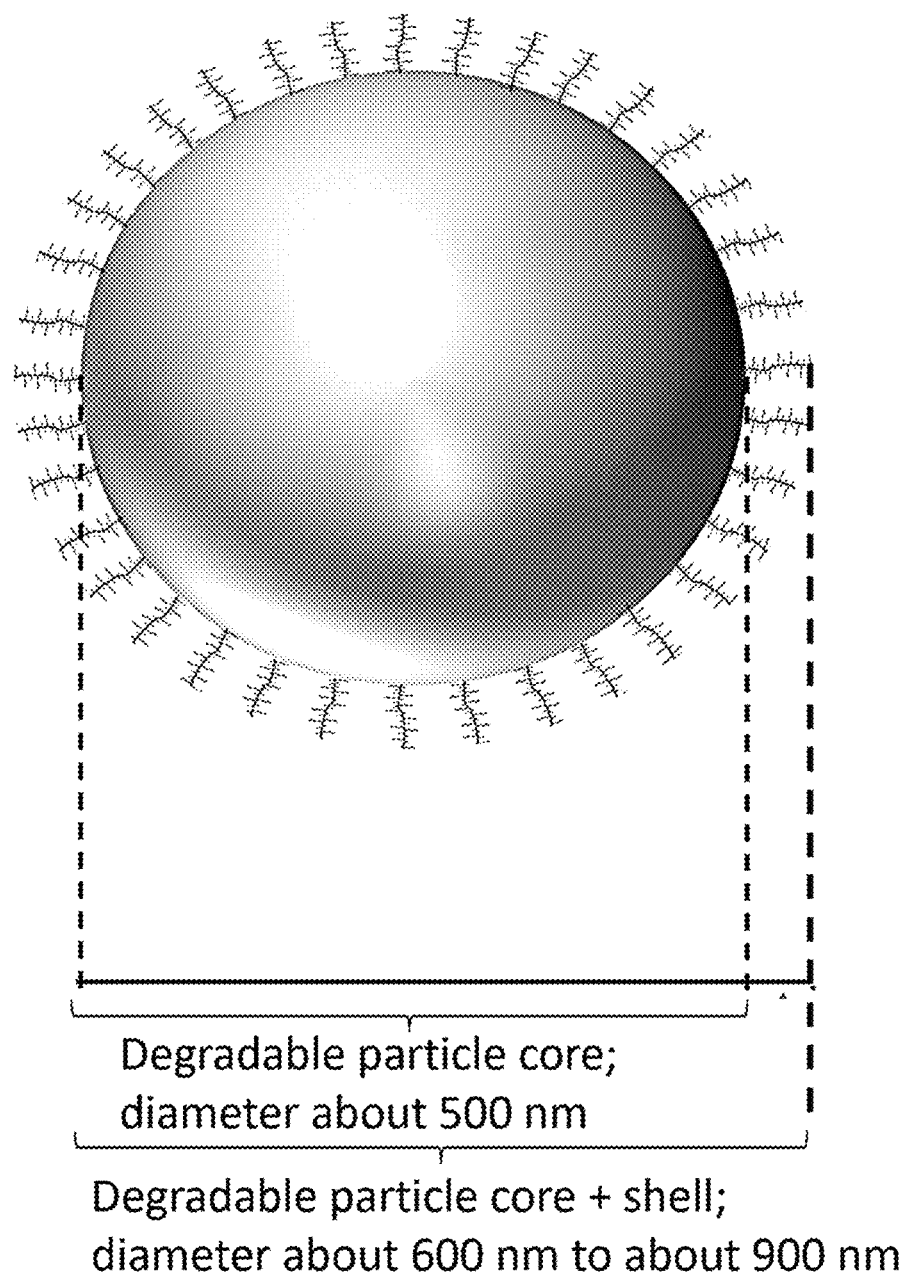
FIGS. 4A-4C.
Figure 4B:
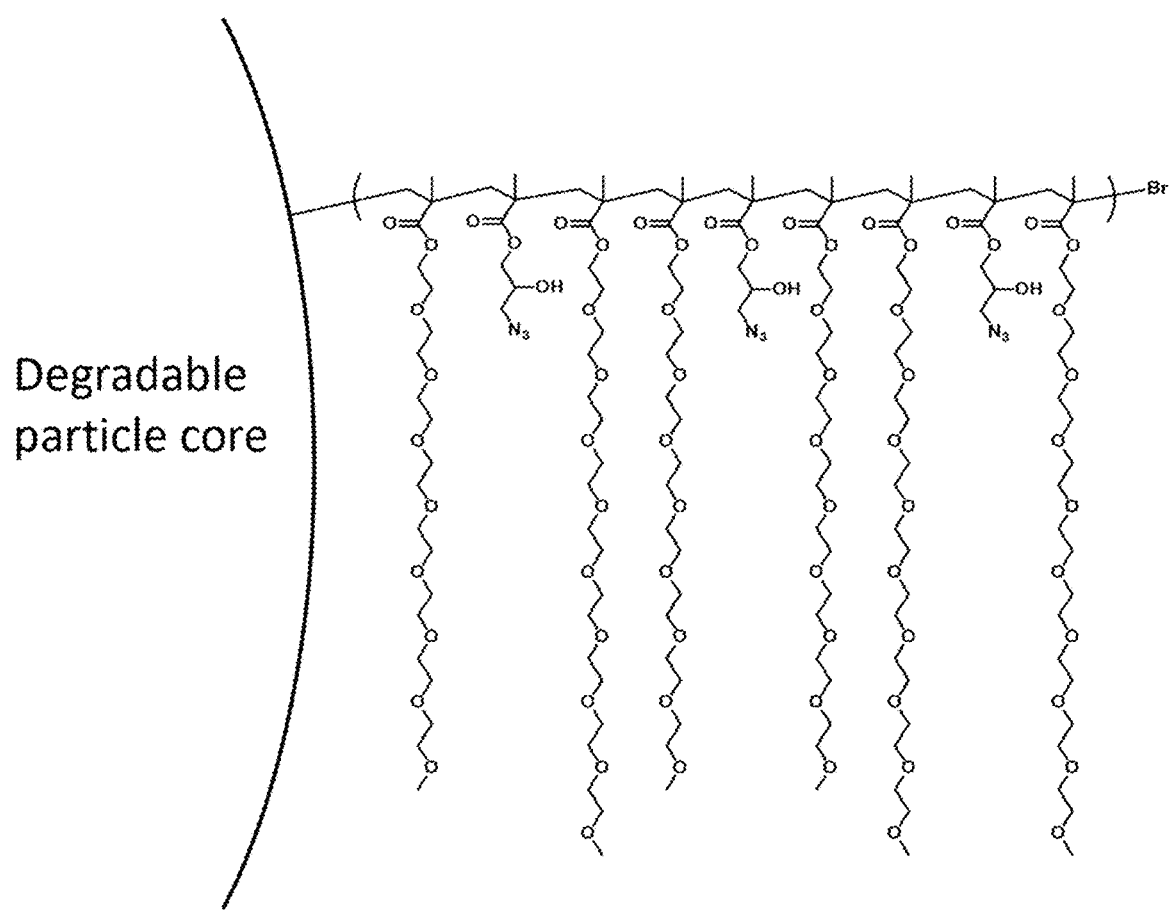
Figure 4C:
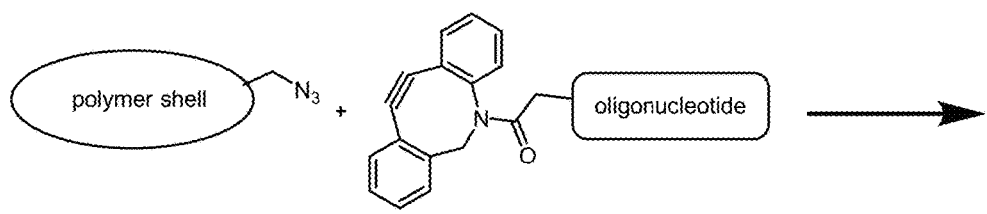
Figure 4C:
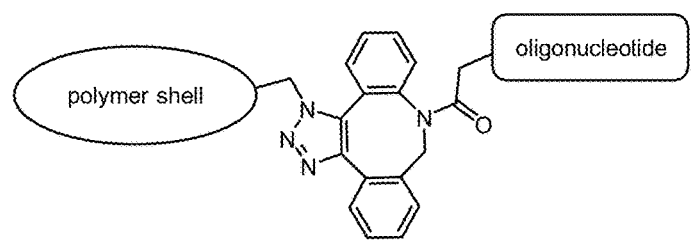

In embodiments, the particle is a solid particle. In embodiments, the particle is rigid and includes a shape. In embodiments, the particle is substantially spherical. In embodiments, the particle is substantially cuboidal. In embodiments, the particle is not an emulsion or droplet. In embodiments, the particle is a functionalized particle including a degradable particle core (e.g., a MOF particle core) and a polymer shell, wherein the polymer shell is covalently attached to the particle core and includes a plurality of polymerized units of shell monomers and one or more shell monomers includes an oligonucleotide moiety covalently linked to the shell monomer. In embodiments, the particle is a functionalized particle including a degradable particle core and a polymer shell surrounding the particle core wherein the polymer shell includes a plurality of polymerized units of shell monomers and one or more of the shell monomers includes an oligonucleotide moiety covalently linked to the shell monomer via a bioconjugate linker. FIGS. 4A-4B illustrate an example of a functionalized particle with a degradable particle core and polymer shell. The polymer shell includes a polymerized units of shell monomers (e.g., PEGMA) linked with bioconjugate reactive moieties (e.g., GMA-Az). In embodiments, the polymerized shell includes linear polymerized units of shell monomers linked with bioconjugate reactive moieties. In embodiments, the linear polymerized units of shell monomers may be crosslinked. In embodiments, the polymerized units of shell monomer are covalently bound to the degradable particle core. For example, the polymerized units of shell monomers are attached to the particle via a polymerization initiator. FIG. 4C illustrates an example of how a polymeric bioconjugate linker is formed between the polymer shell and oligonucleotide through a first reactive moiety (e.g., an azide) and second reactive moiety (e.g., DBCO). In embodiments, the degradable particle core includes a shape and retains its shape during polymerization of the polymer shell (e.g., the spherical degradable particle core remains spherical as the polymer shell is attached to the spherical degradable particle core).

In embodiments, each particle includes a plurality of oligonucleotide moieties covalently attached to the particle via a polymeric bioconjugate linker. In embodiments, the polymeric bioconjugate linker is a polymer (i.e., a molecule including structurally unique repeating units) including one or more reacted bioconjugate reactive moieties. In embodiments, the bioconjugate linker is illustrated in Scheme 1. In embodiments, the polymeric bioconjugate linker is a polymer including a subunit of formula Ia, Ib, II, or III as described in U.S. Pat. No. 11,236,387, which is incorporated herein by reference in its entirety and for all purposes.

In embodiments, the particle includes a degradable particle core surrounded by a polymer shell wherein the polymer shell is functionalized for primer attachment. In embodiments, the particle comprises a degradable particle core surrounded by a polymer shell wherein the polymer shell includes a plurality of polymerized units of shell monomers and one or more shell monomers includes an oligonucleotide moiety covalently linked to the shell monomer. In embodiments, the particle (e.g., a nanoparticle) includes a plurality of oligonucleotide moieties covalently attached to the polymer shell via a bioconjugate linker, wherein the bioconjugate linker is formed via a reaction between a particle polymer including a first bioconjugate reactive moiety and an oligonucleotide including a second bioconjugate reactive moiety as described herein. In embodiments, the particle includes a polymer shell (e.g., a polymer or copolymer described herein).

In embodiments, the oligonucleotide moiety includes a DBCO bioconjugate reactive moiety that reacts with an azide bioconjugate reactive moiety on the particle polymer and forms a bioconjugate linker that covalently links the oligonucleotide moiety to the particle polymer, for example according to the following scheme:

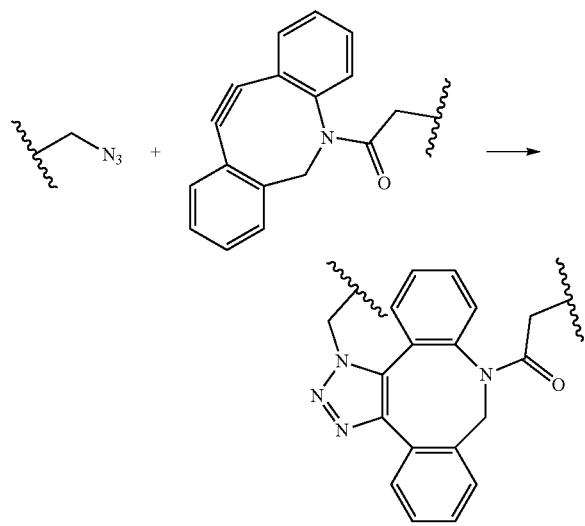

Scheme 1. An example mechanism of the bioconjugate covalent linker formed by reacting a DBCO containing oligonucleotide (oligonucleotide not depicted) with a particle containing an azide moiety (e.g., wherein the azide moiety is provided by the particle shell), wherein the refers to the attachment point to the oligonucleotide moiety and the particle polymer (i.e., the polymer shell), respectively.

In an aspect is provided a plurality of particles wherein each particle is as described herein. In embodiments, each particle of the plurality of particles has the same oligonucleotide moiety or bioconjugate reactive moiety covalently linked to each shell monomer. In embodiments, each particle of the plurality of particles has different oligonucleotide moieties covalently linked to each shell monomer (e.g., a first oligonucleotide moiety with a first sequence and a second oligonucleotide moiety with a second, different, sequence). In embodiments, each particle of the plurality of particles has the same bioconjugate reactive moiety covalently linked to each shell monomer.

In embodiments, the particle includes a degradable particle core surrounded by a polymer shell wherein the polymer shell is functionalized for oligonucleotide (i.e., primer) attachment. In embodiments, the particle includes a degradable particle core surrounded by a polymer shell wherein the polymer shell includes a plurality of polymerized units of shell monomers and one or more shell monomers includes an oligonucleotide moiety covalently linked to the shell monomer.

In embodiments, the particle has a degradable particle core that is a metal-organic framework (MOF) particle core. MOFs are a form of a porous coordination polymer. In embodiments, the MOF particle core is an Isoreticular Metal-Organic Framework (IR-MOF) core, Zeolitic Imidazolate Framework (ZIF) core, Porous Coordination Network (PCN) core, Materials Institute Lavoisier (MIL) MOF core, Porous Coordination Polymer (PCP) core, or University of Oslo (UiO) MOF core. In embodiments, the MOF core is a Zeolitic Imidazolate Framework 8 (ZIF-8) core or a UiO-66 MOF core. The aforementioned MOF cores are known in the art, see for example Zhou et al. review article titled "Introduction to Metal-Organic Framewoks" published in Chem. Rev. 2012, 112, 2, 673-674, Furukawa et al. (see Science, vol. 341, No. 6149, 1230444, 2013), and/or Cohen (see Chem. Reviews, Vol. 112, No. 2, p. 970-1000, 2012).

In embodiments, the MOF particle core is MOF-5 (e.g., Cu-MOF-5, Co-MOF-5, MOF-74 (e.g., Co-MOF-74, Mg-MOF-74, Cu-MOF-74, Zn-MOF-74, or Ni-MOF-74), Cu-BTC (i.e., copper benzene-1,3,5-tricarboxylate (BTC)), HKUST-1 (Hong Kong University of Science and Technology-1), IRMOF-1, IRMOF-3, MIL-100, MIL-100(Fe), MIL-101 (e.g., MIL-101(Cr)), MIL-125 (e.g., MIL-125 (Ti)), MIL-140A, MIL-53 (e.g., MIL-53(Al)), MOF-177, MOF-199, MOF-5, MOF-808 (e.g., MOF-808(Co), MOF-808(Mn), MOF-808(Ni), or MOF-808(Zn)) NOTT-202, NOTT-202 (Nano-Organic-Templated Tecto-Framework-202), NU-1000 (Nanjing University-1000), PCN-14, PCN-222, PCN-222, PCN-224, PCN-225, PCN-227, PCN-244, PCN-245, PCN-250, UiO-66 (University of Oslo-66), UiO-67, UiO-68, UiO-69, UiO-70, UiO-71, ZIF-8 (Zinc Imidazolate Framework-8), or ZIF-90.

In embodiments, the degradable particle core is a polystyrene (PS) particle, or polymethyl methacrylate (PMMA) particle, or latex particle. In embodiments, the MOF particle is any metal-organic framework particle that can be degraded by a change in external conditions, including a change in pH, temperature, or other chemical degrading agent. In embodiments, the MOF particle is a Zeolitic Imidazolate Framework 8 (ZIF-8) particle. In embodiments, the MOF particle is UiO-66. In embodiments, the MOF particle is a Zr based MOFs, mesoporous iron (III) carboxylate MIL-100(Fe). In embodiments, the degrading the degradable particle core does not destroy or damage the oligonucleotide. In embodiments, the degrading the degradable particle core does not destroy or damage the polymer shell. In embodiments, the MOF particle is as described in Furukawa et al. (see Science, vol. 341, No. 6149, 1230444, 2013) or Cohen (see Chem. Reviews, Vol. 112, No. 2, p. 970-1000, 2012).

MOFs comprise both organic and inorganic components. The organic components (bridging ligands/linkers) include a conjugate base of a carboxylic acid or anions, such as organophosphorus compounds, salts of sulfonic acid, and heterocyclic compounds. In embodiments, the MOF particle is synthesized by joining metal-containing units, also known as secondary building units (SBUs), with organic linkers using reticular synthesis. In embodiments, the MOF particle may vary in size and nature of its structure without changing its underlying topology. In embodiments, the MOF particle may be post-synthetically modified so that organic units and metal-organic complexes may be incorporated by reactions with linkers so that the reactivity of the pores is changed. In embodiments, the MOF particle may be multivariate wherein multiple organic functionalities are incorporated within a single framework.

In embodiments, the MOF particle is MOF-5; MOF-177 [Zn₄O(BTB)₂ wherein BTB=4,4',4"-benzene-1,3,5-triyl-bribenzoate]; MOF-200 [Zn₄O(BBC)₂ wherein BBC³⁻ is 4,4',4"'-(benzene-1,3,5-triyl-tris(benzene-4,1-diyl)tribenzoate]; MOF-210 [(Zn₄O)₃(BTE)₄(BPDC)₃ wherein BTE=4, 4',4"-(benzene-1,3,5-triyl-tris(ethyne-2,1-diyl))tribenzoate and BPDC=bipheyl-4,4'-dicarboxylate]; NU-110[Cu₃(BHEHPI) wherein BHEHPI⁶⁻ is 5,5',5"-((((benzene-1,3,5-triyltris(benzene-4,1-diyl))tris(ethyne-2,1-diyl))-tris(benzene-4,1,-diyl))tris(ethyne-2,1-diyl))triisophthalate]; IRMOF-1; 1IMOF-16 [Zn₃O(TPDC)₃ wherein TPDC²⁻ is terphenyl-5,5"-dicarboxylate]; MOF-180 [Zm₄O(BTE)₂], HKUST-1 [Cu₃(BTC)₂ wherein BTC³⁻ is benzene-1,3,5-tricarboxylate]; MOF-399 [Zn₃(TPBTM) wherein TPBTM⁶⁻ is 5,5',5"-((benzene-1,3,5-tricarbonyl)tris(azanediyl))triisophthalate]; Cu₃(TPBTM); Cu₃(TDPAT) wherein TDPAT⁶⁻ is 5,5',5"-(1,3,5-triazine-2,4,6-triyl)tris(azanediyl) triisophthalate; NOTT-112 [Cu₃(BTPI)] wherein BTPI⁶⁻ is 5,5',5"-(benzene-1,3,5-triyl-tris)benzene-4,1-diyl))triisophthalate]; NOTT-116, also known as PCN-68, [Cu₃(PTEI) wherein PTEI⁶⁻ is 5,5',5"-((benzene-1,3,5-triyl-trisbenzene-4,1-diyl)tris(ethyne-2,1-diyl))triisophthalate]; PCN-61 [Cu₃(BTEI) wherein BTEI⁶⁻ is 5,5',5"-(benzene-1,3,5-triyl-tris (ethyne-2,1-diyl))triisophthalate]; PCN-66 [Cu₃(NTEI) wherein NTEI⁶⁻ is 5,5',5"-((nitrilotris(benzene-4,1-diyl))tris (ethyne-2,1-diyl))triisophthalate]; PCN-69, also known as NOTT-119, [Cu₃(BTTI) wherein BTTI⁶⁻ is 5,5',5"=(benzene-1,3,5-triyl-tris(biphenyl-4,4'-dyl))triisophthalate];
PCN-610, also known as NU-100, [Cu₃(TTEI) wherein TTEI⁶⁻ is 5,5',5"-(((benzene-1,3,5-triyl-tris(ethyne-2,1-diyl))tris(benzene-4,1-diyl))tris(ethyne-2,1-diyl))triisophthalate]; NU-108 [Cu₃(BTETCA) wherein BTETCA⁶⁻ is 5,5"",5""'-(benzene-1,3,5-triyl-tris(ethyne-2,1-diyl))tris(([1, 1':3'1"-terphenyl]-4,4"-dicarboxylate))]; NU-109 [Cu₃(BNETPI) wherein BNETPI⁶⁻ is 5,5',5"-(((benzene-1,3,5-triyl-tris(ethyne-2,1-diyl))tris(benzene-4,1-diyl))tris(buta-1, 3-diyne-4,1-diyl))triisophthalate]; NU-110 and NU-111 [Cu₃(BHEI), wherein BHEI⁶⁻ is 5,5',5"-(benzene-1,3,5-ytiyl-tris(buta-1,3-diyne-4,1-diyl))triisophthalate]. In embodiments, the MOF particle is M₃(BTC)₂ wherein M is Zn(II), Fe(II), Mo(II), Cr(II) and Ru(II), MOF-74 [M₂(DOT) wherein DOT is dioxidoterephthalate using divalent metal ions such as Mg, Co, Ni and Mn and M²⁺ is Zn or Mg]. In embodiments, the MOF particle is IRMOF-74-I, IRMOF-74-II, IRMOF-74-III, IRMOF-74-IV, IRMOF-74-V, IRMOF-74-VI, IRMOF-74-VII, IRMOF-74-VIII, IRMOF-74-IX, IRMOF-74-X and IRMOF-74-XI. In embodiments, the MOF particle is MTV-MOF-5, Ag₆(OH₂)(H₂O₄) (TIPA)₅, PCN-14, MOF-2, MOF-11, MOF-73 or POST-1. In embodiments the MOF particle is UiO-66, MOT-525, MOF-545, MOF-11, IRMOF-3, UMCM-1-NH₂, MIL-101, Mn-BTT, MOF-48, PIZA-3, MIL-101(Cr), MIL-53, MIL-68, MOF-5, NU-100, Ni-MOF-74, Mg-MOF-74, Fe-MOF-74, MOF-508, MOF-1001, CPM-7 or CPM-24. In embodiments, the MOF particle is MOF-LIC-1, DMOF-1, UMCM-1, ZIF-90, STAM-1, SNU-30, CAU-1, or SIM-1. In embodiments the MOF particle is ZIF-8, also known as Zn(MIm)₂ wherein MIm is 2-methylimidazolate.

Figure 6A:
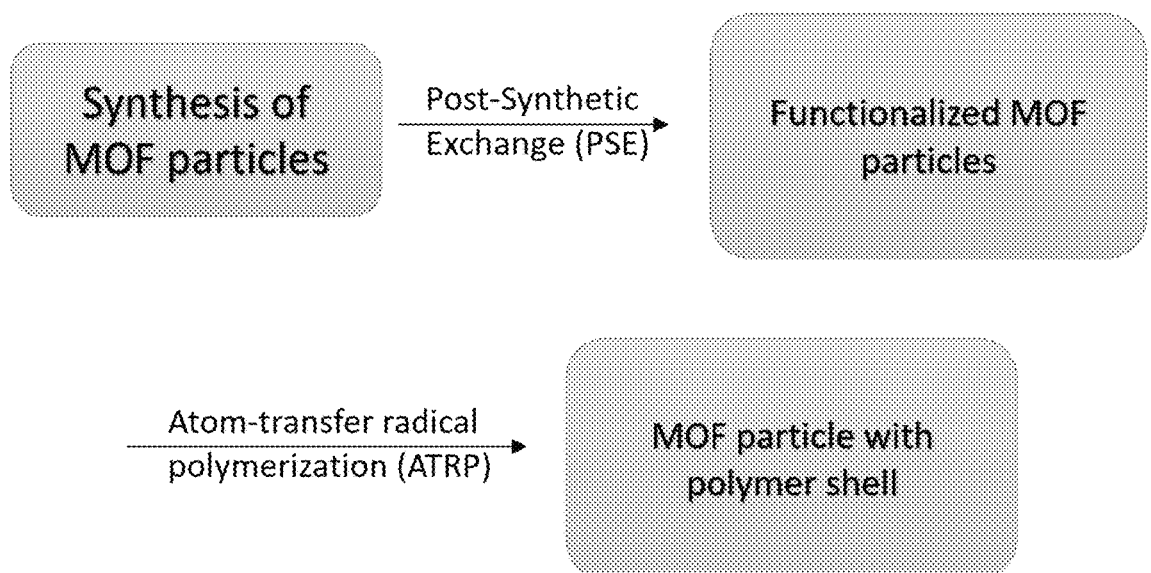
FIGS. 6A-6B depicts a workflow for generating a degradable particle including the polymer shell.
Figure 6B:
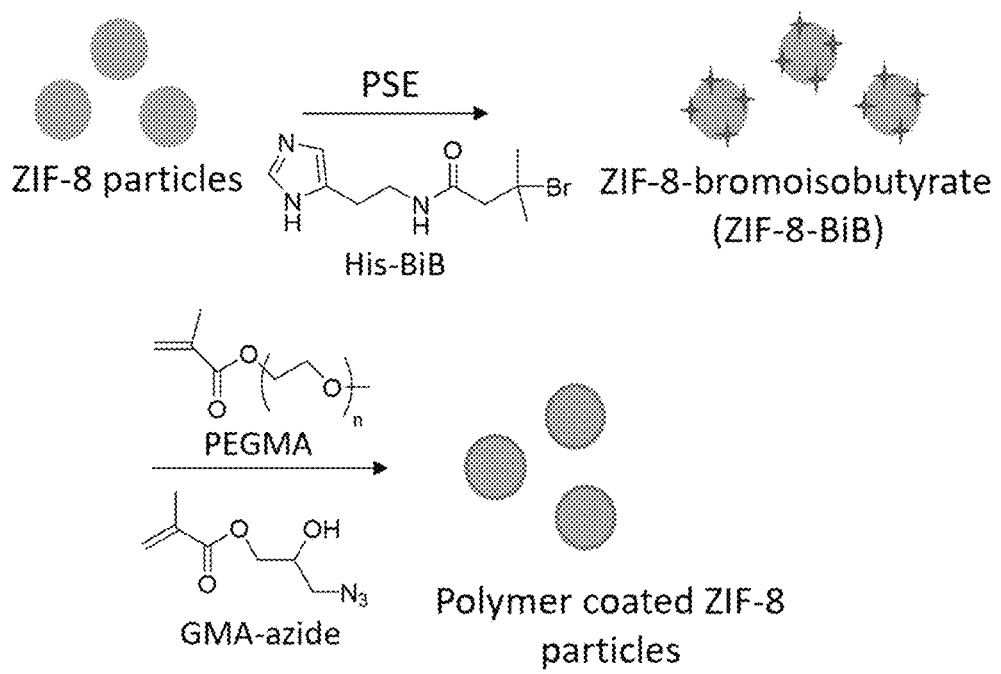

In embodiments, the MOF particle includes a polymer attached to the surface of the particle. In embodiments, polymer coated MOF particles (i.e. MOF particles with a polymer shell) are formed according to the workflow presented in FIGS. 6A-6B. In embodiments, the polymer shell is attached to the MOF particle via post synthetic polymerization (PSP) wherein controlled polymerization occurs from active sites on the MOF surface via a "grafting from" approach common in polymerization protocols. In embodiments, functional groups on the MOF or from the MOF surface (e.g., amino groups of UiO-66(Zr)—NH₂) are used as anchors for polymer attachment. In embodiments, post-synthetic exchange (PSE) is used to functionalize MOF particles (e.g., ZIF-8) that do not inherently include functional groups on the surface as shown in FIG. 6B. In embodiments, the MOF particle undergoes PSE so that an initiator is present on the MOF, thereby allowing atom-transfer radical polymerization (ATRP) which results in surface-modification of the MOF. In embodiments, the MOF particle is functionalized with an ATRP initiator. In embodiments, the MOF particle is functionalized with an ATRP initiator that includes an alkyl halide. In embodiments, the MOF particle is functionalized with the ATRP initiator which contains an alkyl halide and imidazolium moiety. In embodiments, MOF particles including a polymer shell are formed through surface-initiated atom-transfer radical polymerization (SI-ATRP) of methyl methacrylate. In embodiments, the MOF particle is functionalized with the ATRP initiator, N-2(2-(1H-imidazol-4-yl)ethyl)-2-bromo-2-methylpropanamide (His-BiB), having the structure

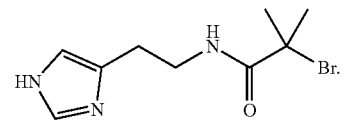

In embodiments, the MOF particle is functionalized with a halogen (e.g., Br group). In embodiments, MOF particles including a polymer shell are formed through surface-initiated atom-transfer radical polymerization (SI-ATRP) of polyethylene glycol methacrylate (PEGMA) and glicydyl methacrylate-azide (GMA-azide) monomers as shown in FIG. 6B. The polymerized PEGMA monomers have the formula

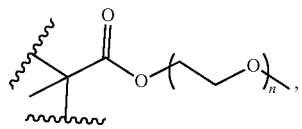

wherein

represents the attachment point to the remainder of the polymer or the ATRP initiator and n is an integer from 1 to 24. The polymerized GMA-azide monomers have the formula

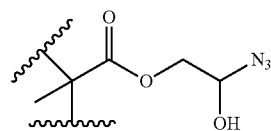 [SMILES: *C(*)(C)C(=O)OCC(O)N=[N+]=[N-]]

or

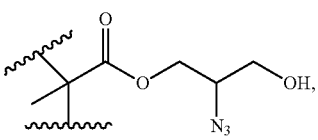

wherein

"⸳⸳⸳§⸳⸳⸳"

represents the attachment point to the remainder of the polymer or the ATRP initiator. In embodiments, a ZIF-8 particle is functionalized with His-BiB then undergoes ATRP with PEGMA and GMA-azide monomers to form a polymer coated ZIF-8 particle as shown in FIG. 6B. In embodiments, the MOF particle is functionalized with an ATRP initiator that includes a vinyl or acrylate moiety, for example styrene, 4VP, 4-vinylpyridine; 2VP, 2-vinylpyridine; MMA, methyl methacrylate; BMA, benzyl methacrylate; DMAEMA, dimethylaminoethyl methacrylate; DMA, N,N-dimethylacrylamide; OEGMA, oligo(ethyleneglycol) methacrylate; HEA, or 2-hydroxyethyl acrylate.

In embodiments, a MOF particle is surface functionalized with a catechol-modified chain-transfer agent (cat-CTA), for example

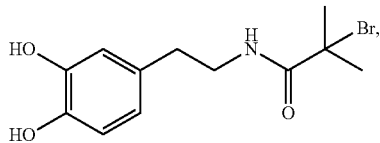 [SMILES: CC(C)(Br)C(=O)NCCc1ccc(O)c(O)c1]

followed by polymer synthesis through surface-initiated reversible addition-fragmentation chain transfer (SI-RAFT) polymerization of a polymer (e.g., methyl methacrylate). RAFT is a controlled-radical polymerization method known for high functional group tolerance and predictable molecular weights.

Figure 7:
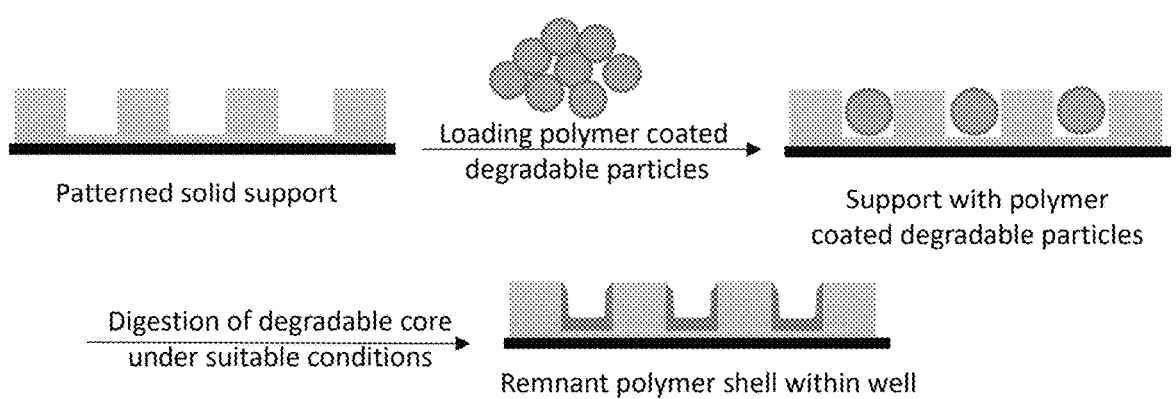
FIG. 7 shows an embodiment for loading the polymer shell into a multiwell container. The degradable particle core and a polymer shell attached to the degradable particle core is deposited onto a solid support containing a plurality of wells. Following deposition, the degradable core is digested under suitable conditions (e.g., contacting the core with an acid or basic solution), rendering the polymer shell attached to and remaining within the wells. The patterned support may then be stored in solution, or further functionalized with oligonucleotides.

In embodiments, a plurality of oligonucleotide moieties is covalently attached to said particle via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the polymeric bioconjugate linker is formed before the degradable particle core is contacted with an external stimulus (e.g. acid or base solution which degrades the particle core). In embodiments, the polymeric bioconjugate linker is formed after the degradable particle core is contacted with an external stimulus (e.g. acid or base solution which degrades the particle core) as shown in FIG. 7.

In embodiments, the degradable particle core can be removed to release material through the presence of an external stimulus. In embodiments, the external stimulus is a change in pH. In embodiments, the pH is altered with a base to degrade the particle core. In embodiments, the base is NaOH. In embodiments, the pH is altered with an acid to degrade the particle core. In embodiments, the external stimulus is the presence of a compound such as phosphate. In embodiments, degrading the particle core causes the release of the polymer shell. In embodiments, the degradable particle core is degraded under conditions that would not degrade and/or alter an oligonucleotide. In embodiments, the mass of the degradable particle core reduces upon incubation with the external stimulus. In embodiments, the shape of the degradable particle core changes to amorphous upon incubation with the external stimulus.

In embodiments, the particle has a polymer shell surrounding the degradable particle core. In embodiments, the polymer shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the polymer shell includes polymerized units of polyethylene glycol methacrylate (PEGMA) and glicydyl methacrylate (GMA). In embodiments, the polymer shell includes polymerized units of polyethylene glycol methacrylate (PEGMA) and isocyanatoethyl methacrylate (IEM). In embodiments, the polymer shell includes polymerized units of glicydyl methacrylate azide (GMA azide) and polyethylene glycol methacrylate (PEGMA).

In embodiments, the polymer shell includes polymerized units of 3-azido-2-hydroxypropyl methacrylate, 2-azido-3-hydroxypropyl methacrylate, 2-(((2-azidoethoxy)carbonyl) amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the polymer shell includes polymerized units of 3-azido-2-hydroxypropyl methacrylate, 2-azido-3-hydroxypropyl methacrylate, or 2-(((2-azidoethoxy)carbonyl) amino)ethyl methacrylate. In embodiments, the polymer shell includes polymerized units of 3-azido-2-hydroxypropyl methacrylate. In embodiments, the polymer shell includes polymerized units of 3-azido-2-hydroxypropyl methacrylate 2-azido-3-hydroxypropyl methacrylate. In embodiments, the polymer shell includes polymerized units of 3-azido-2-hydroxypropyl methacrylate 2-(((2-azidoethoxy)carbonyl)amino)ethyl methacrylate. In embodiments, the polymer shell includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide. In embodiments, the polymer shell is permeable to a polymerase.

In embodiments, the polymer shell includes polymerized units of glicydyl methacrylate azide (GMA azide) and polyethylene glycol methacrylate (PEGMA) in the ratio of 1:1. In embodiments, the ratio of GMA azide to PEGMA is 1:2. In embodiments, the ratio of GMA azide to PEGMA is 1:3. In embodiments, the ratio of GMA azide to PEGMA is 1:4. In embodiments, the ratio of GMA azide to PEGMA is 1:5. In embodiments, the ratio of GMA azide to PEGMA is 1:6. In embodiments, the ratio of GMA azide to PEGMA is 1:7. In embodiments, the ratio of GMA azide to PEGMA is 1:8.

The polymer shell may be polymerized from a mixture of functionalized and non-functionalized monomers, such that at least some functionalized monomers that provide attachment points (e.g., azide moieties) for primers (e.g., DBCO-containing oligonucleotide primers) are spaced from one another by one or more monomers lacking such attachment points (e.g., PEG or AAm). The frequency of monomer units attached to primers within a polymer can be adjusted by changing the concentration of the corresponding functionalized monomer in the mixture of monomers. In embodiments, monomer units of the polymer that are attached to a polynucleotide primer (referred to herein as oligonucleotide moieties) are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the polymer that are attached to a polynucleotide primer are separated by, on average, about or at least about 4 to 8 monomer units that are not attached to a primer. In embodiments, monomer units of the polymer that are attached to a polynucleotide primer are separated by, on average, about or at least about 6, 7, or 8 monomer units that are not attached to a primer. In embodiments, primer-attached monomers are separated by, on average, about 1-50, 2-40, 3-30, 4-25, or 5-20 monomers not attached to primers. In embodiments, monomer units of the polymer that are attached to a polynucleotide primer are separated by 3 monomer units that are not attached to a primer (referred to as having a degree of polymerization of 3, also referred to as 3 ng). In embodiments, monomer units of the polymer that are attached to a polynucleotide primer are separated by 6 ng. In embodiments, monomer units the polymer that are attached to a polynucleotide primer are separated by 9 ng. The mixture can include monomers with different functional groups (e.g., azides, alkynes, DBCO, etc.) as described herein.

In embodiments, the polymer shell is permeable to a polymerase. In embodiments, the particle is permeable to a polymerase. In embodiments, the polymer shell is permeable to an amplification reaction mixture and/or a sequencing reaction mixture. In embodiments, the particle is permeable to an amplification reaction mixture and/or a sequencing reaction mixture. In embodiments, the polymer shell is permeable to a sequencing reaction mixture. In embodiments, the particle is permeable to a sequencing reaction mixture. In embodiments, the particle is permeable to a polymerase for amplifying the target polynucleotide. In embodiments, the polymer shell is permeable to a polymerase for amplifying the target polynucleotide, such that the interface of the core is in contact with the polymerase. The term "sequencing reaction mixture" and refers to an aqueous mixture that contains the agents and reagents necessary to allow addition of a nucleotide to a polynucleotide strand by a polymerase (e.g., addition of a dNTP or dNTP analogue to a DNA strand by a DNA polymerase) and subsequent detection. Exemplary mixtures of agents and reagents include buffers (e.g., saline-sodium citrate (SSC), tris(hydroxymethyl)aminomethane or "Tris", or TE), salts (e.g., KCl or (NH4)2SO4)), nucleotides (e.g., modified nucleotides), polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), detergents and/or crowding agents (e.g., PEG, Tween, BSA). In embodiments, the modified nucleotides are reversibly terminated nucleotides linked to fluorescent dyes, such that the identity of a nucleotide added in a sequencing reaction can be identified based on the fluorescent dye with which it is associated. The term "amplification reaction mixture" refers to an aqueous mixture that contains the agents and reagents necessary to make one or more copies of a nucleic acid. Exemplary components include s polymerase, a nucleic acid template, a suitable primer or set of primers, suitable nucleotides (e.g., dNTPs), and a suitable buffer. In embodiments, the polymer shell is porous.

In embodiments, the average longest dimension of the particle is from about 100 nm to about 3000 nm. In embodiments, the average longest dimension of the particle is from about 200 nm to about 2900 nm. In embodiments, the average longest dimension of the particle is from about 300 nm to about 2800 nm. In embodiments, the average longest dimension of the particle is from about 400 nm to about 2700 nm. In embodiments, the average longest dimension of the particle is from about 500 nm to about 2600 nm. In embodiments, the average longest dimension of the particle is from about 600 nm to about 2500 nm. In embodiments, the average longest dimension of the particle is from about 700 nm to about 2400 nm. In embodiments, the average longest dimension of the particle is from about 800 nm to about 2300 nm. In embodiments, the average longest dimension of the particle is from about 900 nm to about 2200 nm. In embodiments, the average longest dimension of the particle is from about 1000 nm to about 2100 nm. In embodiments, the average longest dimension of the particle is from about 900 nm to about 2000 nm. In embodiments, the average longest dimension of the particle is from about 150 nm to about 600 nm. In some embodiments, the average longest dimension of the particle is from about 350 nm to about 600 nm. In some embodiments, the average longest dimension of the particle is from about 400 nm to about 500 nm. In some embodiments, the average longest dimension of the particle is about 500 nm. In some embodiments, the average longest dimension of the particle is about 400 nm. In some embodiments, the average longest dimension of the particle is about 400 nm, 450 nm, 500 nm, or 550 nm. In some embodiments, the average longest dimension of the particle is about 410 nm, 420 nm, 430 nm, 440 nm or 450 nm. In some embodiments, the average longest dimension of the particle is about 460 nm, 470 nm, 480 nm, 490 nm or 500 nm. In some embodiments, the average longest dimension of the particle is at least, about, or at most 100, 200, 300, 400, 500, 600, 700, 800, 900, 1000 nm or a number or a range between any two of these values. In embodiments, the average longest dimension of the degradable particle core is from about 100 nm to about 3000 nm. In embodiments, the average longest dimension of the degradable particle core is from about 200 nm to about 2900 nm. In embodiments, the average longest dimension of the degradable particle core is from about 300 nm to about 2800 nm. In embodiments, the average longest dimension of the degradable particle core is from about 400 nm to about 2700 nm. In embodiments, the average longest dimension of the degradable particle core is from about 500 nm to about 2600 nm. In embodiments, the average longest dimension of the degradable particle core is from about 600 nm to about 2500 nm. In embodiments, the average longest dimension of the degradable particle core is from about 700 nm to about 2400 nm. In embodiments, the average longest dimension of the degradable particle core is from about 800 nm to about 2300 nm. In embodiments, the average longest dimension of the degradable particle core is from about 900 nm to about 2200 nm. In embodiments, the average longest dimension of the degradable particle core is from about 1000 nm to about 2100 nm. In embodiments, the average longest dimension of the degradable particle core is from about 900 nm to about 2000 nm. In embodiments, the average longest dimension of the degradable particle core is from about 150 nm to about 600 nm. In some embodiments, the average longest dimension of the degradable particle core is from about 350 nm to about 600 nm.

In some embodiments, the average longest dimension of the degradable particle core is from about 400 nm to about 500 nm. In some embodiments, the average longest dimension of the degradable particle core is about 500 nm. In some embodiments, the average longest dimension of the degradable particle core is about 400 nm. In some embodiments, the average longest dimension of the degradable particle core is about 400 nm, 450 nm, 500 nm, or 550 nm. In some embodiments, the average longest dimension of the degradable particle core is about 410 nm, 420 nm, 430 nm, 440 nm or 450 nm. In some embodiments, the average longest dimension of the degradable particle core is about 460 nm, 470 nm, 480 nm, 490 nm or 500 nm. In embodiments, the average longest dimension of the degradable particle core is at least, about, or at most 100, 200, 300, 400, 500, 600, 700, 800, 900, 1000 nm or a number or a range between any two of these values. In embodiments, the shell diameter is about 0.1-10 microns, 0.25-5 microns, 0.5-2 microns, 1 micron, or a number or a range between any two of these values. In embodiments, the particle shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 µm or a number or a range between any two of these values. In embodiments, the core diameter is about 150-700 nanometers, and/or the shell diameter is about 0.25-5 µm (microns).

In embodiments, the average longest dimension of the nanoparticle is from about 100 nm to about 400 nm. In embodiments, the average longest dimension of the nanoparticle is about 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm. In embodiments, the average longest dimension of the nanoparticle is less than about 1000 nm. In embodiments, the average longest dimension of the nanoparticle is less than about 900 nm. In embodiments, the average longest dimension of the nanoparticle is less than about 800 nm. In embodiments, the average longest dimension of the nanoparticle is less than about 700 nm. In embodiments, the average longest dimension of the nanoparticle is less than about 600 nm. In embodiments, the average longest dimension of the nanoparticle is less than about 500 nm. In embodiments, the average longest dimension of the nanoparticle is less than about 400 nm. In embodiments, the average longest dimension of the nanoparticle is less than about 300 nm. In embodiments, the average longest dimension of the nanoparticle is less than about 200 nm. In embodiments, the average longest dimension of the nanoparticle is less than about 100 nm. In embodiments, the average longest dimension of the nanoparticle is 400 nm without the particle shell.

In embodiments, the particle has a polymer shell that includes polymerized units of shell monomers. The oligonucleotide moieties are covalently attached via a bioconjugate linker to the polymer shell. The bioconjugate linker is the product of a reaction between the two bioconjugate group (e.g., click chemistry group). The manner in which an oligonucleotide primer is attached to the polymer will depend on the type of functional group used to form the attachment. A variety of suitable functional groups are available, examples of which are provided herein. The polymer may be polymerized from a mixture of functionalized and non-functionalized monomers, and/or a mixture of monomers with different functional groups. In embodiments, functional groups are selected that specifically react with their intended target (e.g., a paired functional group attached to a desired target, such as a primer), while also exhibiting anti-fouling characteristics that prevent, or have a reduced propensity for, non-specific binding of enzymes, dye-labeled nucleotides, and nucleic acids. In embodiments, the oligonucleotide moiety (alternatively referred to herein as primer or polynucleotide primer) is covalently attached to the polymer. In embodiments, the 5' end of the oligonucleotide moiety contains a functional group that is tethered to the polymer (i.e., the polymer shell of the particle). Non-limiting examples of covalent attachment include amine-modified oligonucleotide moieties reacting with epoxy or isothiocyanate groups on the polymer, succinylated oligonucleotide moieties reacting with aminophenyl or aminopropyl functional groups on the polymer, dibenzocyclocytne-modified oligonucleotide moieties reacting with azide functional groups on the polymer (or vice versa), trans-cyclooctyne-modified oligonucleotide moieties reacting with tetrazine or methyl tetrazine groups on the polymer (or vice versa), disulfide modified oligonucleotide moieties reacting with mercapto-functional groups on the polymer, amine-functionalized oligonucleotide moieties reacting with carboxylic acid groups on the polymer via 1-ethyl-3-(3-dimethylaminopropyl)-carbodiimide hydrochloride (EDC) chemistry, thiol-modified oligonucleotide moieties attaching to a polymer via a disulfide bond or maleimide linkage, alkyne-modified oligonucleotide moieties attaching to a polymer via copper-catalyzed click reactions to azide functional groups on the polymer, and acrydite-modified oligonucleotide moieties polymerizing with free acrylic acid monomers on the polymer to form polyacrylamide or reacting with thiol groups on the polymer. In embodiments, the oligonucleotide moiety is attached to the polymer through electrostatic binding. For example, the negatively charged phosphate backbone of the primer may be bound electrostatically to positively charged monomers in the polymer. In embodiments, each platform primer is attached to the polymer, each of which may be present in multiple copies. In embodiments, about or at most at most about 50%, 40%, 30%, 25%, 20%, 15%, 10%, 5%, or less of the polymerized monomers are attached to a platform primer (i.e. a first platform primer, a second platform primer, or a complement of any of these thereof). In embodiments, about 1-25%, about 2-20%, about 3-15%, about 4-14%, or about 5-12% of the polymerized monomers are attached to a copy of a platform primer, or a number or a range between any two of these values. In embodiments, about 5-10% of the polymerized monomers are attached to a copy of a platform primer.

In embodiments, the particle includes a plurality of bioconjugate reactive moieties, wherein the bioconjugate reactive moiety is provided by the polymer shell. In embodiments, a bioconjugate reactive moiety includes an amine moiety, aldehyde moiety, alkyne moiety, azide moiety, carboxylic acid moiety, dibenzocyclooctyne (DBCO) moiety, norbornene moiety, tetrazine moiety, epoxy moiety, isocyanate moiety, furan moiety, maleimide moiety, thiol moiety, or transcyclooctene (TCO) moiety. In embodiments, the particle includes a plurality of azide moieties, alkyne moieties, dibenzocyclooctyne (DBCO) moieties, norbornene moieties, epoxy moieties, or isocyanate moieties. In some embodiments, the particle includes a plurality of oligonucleotide moieties (e.g., ssDNA moieties) covalently attached via a bioconjugate linker to the polymer shell. The bioconjugate linker is the product of a reaction between the two bioconjugate group (e.g., click chemistry group). In embodiments, each of the plurality of bioconjugate reactive moieties includes an amine moiety, aldehyde moiety, alkyne moiety, azide moiety, carboxylic acid moiety, dibenzocyclooctyne (DBCO) moiety, norbornene moiety, tetrazine moiety, epoxy moiety, isocyanate moiety, furan moiety, maleimide moiety, thiol moiety, or transcyclooctene (TCO) moiety. In embodiments, each of the plurality of bioconjugate reactive moieties include an amine moiety, azide moiety, dibenzocyclooctyne (DBCO) moiety, epoxy moiety, or isocyanate moiety. In embodiments, each of the plurality of bioconjugate reactive moieties include an amine moiety, azide moiety, alkyne moiety, dibenzocyclooctyne (DBCO) moiety, epoxy moiety, or isocyanate moiety. In embodiments, the bioconjugate reactive moiety is an azido moiety. In embodiments, the first bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the second bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the first and the second bioconjugate reactive moieties are different. In embodiments, the first and the second bioconjugate reactive moieties are reactive with each other (e.g., an azide moiety and an DBCO moiety) and form a bioconjugate linker.

In embodiments, the particle polymers (e.g., polymerized units of shell monomers) include the same set of first bioconjugate reactive moieties. In embodiments, the oligonucleotide moieties include the same set of second bioconjugate reactive moieties. In embodiments, the same set of first bioconjugate reactive moieties is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the same set of second bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the same set of first bioconjugate reactive moieties is an azide moiety. In embodiments, the same set of second bioconjugate reactive moieties is a DBCO moiety. In embodiments, the first bioconjugate reactive moiety of the particle polymer reacts with the second bioconjugate reactive moiety of the oligonucleotide moieties to form a bioconjugate linker. In embodiments, the bioconjugate linker is formed by the reaction between an azide moiety and a dibenzocyclooctyne (DBCO) moiety.

In embodiments, each particle includes multiple copies of one or more oligonucleotide moieties. In embodiments, each particle includes multiple copies oligonucleotide moieties having the same sequence. In embodiments, the one or more oligonucleotide moieties include at least two different primers attached to the polymer (e.g., a forward and a reverse primer), each of which may be present in multiple copies. In embodiments, about or at most at most about 50%, 40%, 30%, 25%, 20%, 15%, 10%, 5%, or less of the monomers in the polymer of each particle are attached to a copy of the oligonucleotide moiety. In embodiments, about 1-25%, about 2-20%, about 3-15%, about 4-14%, or about 5-12% of the monomers in the polymer of each particle are attached to a copy of the oligonucleotide moiety, or a number or a range between any two of these values. In embodiments, about 5-10% of the monomers in the polymer of each particle are attached to a copy of the oligonucleotide moiety. In embodiments, two different oligonucleotide moieties are attached to the particle (e.g., a forward and a reverse primer), which facilitates generating multiple amplification products from the first extension product or a complement thereof. In embodiments, forward primers anneal to the antisense strand of the double-stranded DNA, which runs from the 3' to 5' direction. Forward primers, for example, initiate the synthesis of a gene in the 5' to 3' direction. In embodiments, reverse primers anneal to the sense strand of the double-stranded DNA, which runs from the 5' to 3' direction. Reverse primers, for example, initiate the synthesis of a gene in the 3' to 5' direction.

In embodiments, the particle includes a first plurality of oligonucleotide moieties and a second plurality of oligonucleotide moieties. The first plurality of oligonucleotide moieties is different from the second plurality of oligonucleotide moieties. In embodiments, the particle has a plurality of oligonucleotide moieties that is about 10 to about 250 nucleotides in length. In embodiments, the particle has a plurality of oligonucleotide moieties that is about 15 to about 60 nucleotides in length. In embodiments, each of the particles include substantially the same oligonucleotide moieties (e.g., a first population of oligonucleotide moieties and a different second population of oligonucleotide moieties). In embodiments, each of the particles include at least two species of substantially the same oligonucleotide moieties (i.e., the same sequences). In embodiments, each particle includes a first plurality of a platform primer sequence and a second plurality of a differing platform primer sequence. In embodiments, the platform primer sequence is used during amplification reactions (e.g., solid phase amplification).

In embodiments, each particle includes a plurality of P7 or P5 nucleic acid sequences or complementary sequences thereof (i.e., P5' or P7'). The P5 and P7 adapter sequences are described in U.S. Patent Publication No. 2011/0059865 A1, which is incorporated herein by reference in its entirety. The terms P5 and P7 may be used when referring to amplification primers, e.g., universal primers. The terms P5' (P5 prime) and P7' (P7 prime) refer to the complement of P5 and P7, respectively. In embodiments, each particle includes a plurality of S1 or S1 nucleic acid sequences or complementary sequences thereof (i.e., S1' or S2'). The S1 and S2 sequences are described in PCT/US2022/075197, which is incorporated herein by reference in its entirety. The terms S1 and S2 may be used when referring to amplification primers, e.g., universal primers. The terms S1 (S1 prime) and S2' (S2 prime) refer to the complement of S1 and S2, respectively. In embodiments, each particle includes oligonucleotide moieties capable of annealing to an adapter of a library nucleic acid molecule. The term "library" merely refers to a collection or plurality of template nucleic acid molecules which share common sequences at their 5' ends (e.g., the first end) and common sequences at their 3' ends (e.g., the second end). The term "adapter" as used herein refers to any linear oligonucleotide that can be ligated to a nucleic acid molecule, thereby generating nucleic acid products that can be sequenced on a sequencing platform (e.g., an Illumina® or Singular Genomics® sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 or Si and S2 sequences sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In embodiments, each of the particles include at least two populations of substantially the same oligonucleotide moieties.

In some embodiments, the oligonucleotide moiety is about 5 to about 250 nucleotides in length. In some embodiments, the oligonucleotide moiety is about 5 to about 200 nucleotides in length. In some embodiments, the oligonucleotide moiety is about 5 to about 150 nucleotides in length. In some embodiments, the oligonucleotide moiety is about 5 to about 100 nucleotides in length. In some embodiments, the oligonucleotide moiety is about 5 to about 60 nucleotides in length. In some embodiments, the oligonucleotide moiety is about 5 to about 50 nucleotides in length. In some embodiments, the oligonucleotide moiety is about 5 to about 40 nucleotides in length. In some embodiments, the oligonucleotide moiety is about 10 to about 250 nucleotides in length. In some embodiments, the oligonucleotide moiety is about 10 to about 200 nucleotides in length. In some embodiments, the oligonucleotide moiety is about 10 to about 150 nucleotides in length. In some embodiments, the oligonucleotide moiety is about 10 to about 100 nucleotides in length. In some embodiments, the oligonucleotide moiety is about 10 to about 60 nucleotides in length. In some embodiments, the oligonucleotide moiety is about 10 to about 50 nucleotides in length. In some embodiments, the oligonucleotide moiety is about 10 to about 45 nucleotides in length. In some embodiments, the oligonucleotide moiety is about 10 to about 40 nucleotides in length. In some embodiments, the oligonucleotide moiety is about 15 to about 100 nucleotides in length. In some embodiments, the oligonucleotide moiety is about 15 to about 90 nucleotides in length. In some embodiments, the oligonucleotide moiety is about 15 to about 80 nucleotides in length. In some embodiments, the oligonucleotide moiety is about 15 to about 70 nucleotides in length. In some embodiments, the oligonucleotide moiety is about 15 to about 60 nucleotides in length. In some embodiments, the oligonucleotide moiety is about 15 to about 50 nucleotides in length. In some embodiments, the oligonucleotide moiety is about 15 to about 40 nucleotides in length. In some embodiments, the oligonucleotide moiety is about 15 to about 30 nucleotides in length. In some embodiments, the oligonucleotide moiety is about 20 to about 35 nucleotides in length. In some embodiments, the oligonucleotide moiety is about 20 to about 30 nucleotides in length. In some embodiments, the oligonucleotide moiety is about 25 to about 30 nucleotides in length. In some embodiments, the oligonucleotide moiety is about 25 to about 35 nucleotides in length. In some embodiments, the oligonucleotide moiety is about 30 to about 50 nucleotides in length. In some embodiments, the oligonucleotide moiety is about 30 to about 75 nucleotides in length. In some embodiments, the oligonucleotide moiety is about 50 to about 150 nucleotides in length. In some embodiments, the oligonucleotide moiety is about 75 to about 200 nucleotides in length. In embodiments, the oligonucleotide moiety is a capture oligonucleotide, wherein the oligonucleotide is capable of hybridizing to a common sequence in a library of nucleic acid molecules. In embodiments, the oligonucleotide is capable of hybridizing to a common sequence (e.g., a sequence described in U.S. Patent Publication 2016/0256846, which is incorporated herein by reference, for example SEQ ID NO: 3, SEQ ID NO: 4, SEQ ID NO: 5, or SEQ ID NO: 11 of U.S. Patent Publication 2016/0256846).

In embodiments, the oligonucleotide moiety includes spacer nucleotides. Including spacer nucleotides in the linker puts the target polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the particle or is attached through a very short linker (e.g., a linker including about 1 to 3 carbon atoms). Spacer nucleotides form part of the oligonucleotide moiety but do not participate in any reaction carried out on or with the oligonucleotide (e.g., a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use polyT spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of oligonucleotide which are attached to the particle. Attachment can be achieved via a phosphorothioate present at the 5' end of the oligonucleotide, an azide moiety, a dibenzocyclooctyne (DBCO) moiety, or any other bioconjugate reactive moiety. The linker may be a carbon-containing chain such as those of formula —$(CH_2)_n$— wherein "n" is an integer from 1 to about 1000. However, a variety of other linkers may be used so long as the linkers are stable under conditions used in DNA sequencing. In embodiments, the linker includes polyethylene glycol (PEG) having a general formula of —$(CH_2—CH_2—O)_m$—, wherein m is an integer from about 1 to about 500. In embodiments, m is an integer from 8 to 24. In embodiments, m is 4, 8, 12, 16, or 24. In embodiments, the oligonucleotide includes a plurality of consecutive dTTP nucleotides (e.g., 4 to 12 dTTP nucleotides). In embodiments, the oligonucleotide includes a plurality of consecutive dUTP nucleotides (e.g., 4 dUTP nucleotides).

In embodiments, the linker, or the oligonucleotides (e.g., primers) include a cleavable site. A cleavage site is a site which allows controlled cleavage of the immobilized polynucleotide strand (e.g., the linker, the primer, or the polynucleotide) by chemical, enzymatic or photochemical means. Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the oligonucleotide (e.g., within the oligonucleotide sequence of the primer). In embodiments, the linker or the oligonucleotide, includes a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Oligonucleotide nucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof. In embodiments, the oligonucleotide includes one or more uracil nucleotides.

In embodiments, each of the particle-immobilized oligonucleotides (e.g., immobilized primers) is about 5 to about 25 nucleotides in length. In embodiments, each of the particle-immobilized oligonucleotides (e.g., immobilized primers) is about 10 to about 40 nucleotides in length. In embodiments, each of the particle-immobilized oligonucleotides (e.g., immobilized primers) is about 15 to 60 nucleotides in length. In embodiments, each of the particle-immobilized oligonucleotides (e.g., immobilized primers) is about 5 to about 100 nucleotides in length. In embodiments, each of the particle-immobilized oligonucleotides (e.g., immobilized primers) is about 20 to 200 nucleotides in length. In embodiments, each of the particle-immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more particle-immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the 3' modification is a 3'-phosphate modification includes a 3' phosphate moiety, which is removed by a PNK enzyme.

In embodiments, the oligonucleotide moiety includes one or more phosphorothioate nucleotides. In embodiments, the oligonucleotide moiety includes a plurality of phosphorothioate nucleotides. In embodiments, about or at least about 20%, 30%, 40%, 50%, 60%, 70%, 80%, 90%, or about 100% of the nucleotides in the oligonucleotide moiety are phosphorothioate nucleotides. In embodiments, most of the nucleotides in the oligonucleotide moiety are phosphorothioate nucleotides. In embodiments, all of the nucleotides in the oligonucleotide moiety are phosphorothioate nucleotides. In embodiments, none of the nucleotides in the oligonucleotide moiety are phosphorothioate nucleotides.

In some embodiments, the oligonucleotide moiety is capable of hybridizing to a complementary sequence of a template nucleic acid. In embodiments, the oligonucleotide moiety includes DNA. In embodiments, the oligonucleotide moiety includes RNA. In embodiments, the oligonucleotide moiety is DNA. In embodiments, the oligonucleotide moiety is RNA. In embodiments, the oligonucleotide moiety includes a single-stranded DNA. In embodiments, the oligonucleotide moiety includes a single-stranded RNA. In embodiments, the oligonucleotide moiety is a single-stranded DNA. In embodiments, the oligonucleotide moiety is a single-stranded RNA. In embodiments, the oligonucleotide moiety is a nucleic acid sequence complementary to a target polynucleotide (e.g., complementary to a common adapter sequence of the target polynucleotide).

In embodiments, each of the oligonucleotide moieties (e.g., the platform primers) include a cleavable site. The cleavable site in the platform primer is a site which allows controlled cleavage of the polynucleotide strand by chemical, enzymatic, or photochemical means. In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent. In embodiments, the cleavable site includes one or more deoxyuracil nucleobases (dUs). In embodiments, the cleavable site includes one or more ribonucleotides. In embodiments, the cleavable site includes 2 to 5 ribonucleotides. In embodiments, the cleavable site includes one ribonucleotide. In embodiments, the cleavable site includes more than one ribonucleotide. In embodiments, the cleavable site includes deoxyuracil triphosphate (dUTP) or deoxy-8-oxo-guanine triphosphate (d-8-oxoG). The cleavable site can be cleaved using methods described herein. For example, in embodiments, cleaving the cleavable site includes contacting the cleavable site with a cleaving agent. In embodiments, the cleaving agent is selected from sodium periodate, RNase, formamidopyrimidine DNA glycosylase (Fpg), endonuclease, uracil DNA glycosylase (UDG), TCEP, THPP, sodium dithionite ($Na_2S_2O_4$), hydrazine ($N_2H_4$), Pd(0), or ultraviolet radiation.

In embodiments, cleavage of the cleavable site, which includes a modified nucleotide, for example, one or more uracils, may be accomplished using a cleavage mixture including about 150 mM to about 300 mM glycine-KOH, about 5 mM to about 15 mM MgCl2, about 0.05% to about 0.15% Triton X-100, and about 0.05 U/uL to about 0.2 U/uL uracil DNA glycosylase (UDG). In embodiments, the cleavage mixture can have a pH greater than pH 8.0, greater than pH 8.5, greater than pH 9.0, greater than pH 9.5, or greater than pH 10.0. In other embodiments, the cleavage mixture can have a pH ranging, for example, from about pH 8.0 to about pH 10.0, from about pH 8.5 to about pH 10.0, or from about pH 9.0 to about pH 10.0. For example, the cleavage mixture is applied to an immobilized oligonucleotide (i.e. a platform primer) including one or more uracils, incubated at about 37° C. to about 42° C. for 10 min, and then incubated at about 65° C. to about 72° C. for 30 min. Following cleavage, the surface is washed with wash buffer, followed by subsequent washes with about 0.05M NaOH to about 0.15M NaOH, and another wash with wash buffer.

In embodiments, the particles are non-covalently attached to the wells (e.g., one or more particles are non-covalently attached to a surface inside or within the well). In embodiments, the particles are physiosorbed to the wells. In embodiments, the particles are covalently attached to the wells. In embodiments, each particle attaches to the polymer layer of the surface (e.g., non-covalently attach to the polymer layer). In embodiments, the particles contact the well and remain attached without any additional means for attachment (e.g., hybridization of complementary oligonucleotides immobilized on the solid support). In embodiments, the solid support does not include immobilized oligonucleotides.

In an aspect is provided a solid support (e.g., a patterned glass slide or planar support) including one or more particle having a degradable particle core; a polymer shell attached to the particle core wherein the polymer shell includes a plurality of polymerized units of shell monomers, wherein one or more shell monomers include an oligonucleotide moiety covalently linked to the shell monomer, as described herein. In embodiments, the solid support includes two or more wells, wherein each well includes a particle as described herein.

In embodiments, the solid support includes a plurality of wells (e.g., a billion or more wells). In embodiments, the wells (e.g., each well) is separated from each other by about 0.2 µm to about 2.0 µm. In embodiments, the wells (e.g., each well) is separated from each other by about 0.3 µm to about 2.0 µm. In embodiments, the wells (e.g., each well) is separated from each other by about 0.4 µm to about 2.0 µm. In embodiments, the wells (e.g., each well) is separated from each other by about 0.5 µm to about 2.0 µm. In embodiments, the wells (e.g., each well) is separated from each other by about 1.0 µm to about 2.0 µm. In embodiments, the wells (e.g., each well) is separated from each other by about 1.0 µm to about 1.5 µm. In embodiments, the wells of the solid support are all substantially the same size (e.g., within a tolerance). In embodiments, the solid support includes wells that are from about 0.1 µm to about 3 µm in diameter. In embodiments, the solid support includes wells that are from about 0.2 µm to about 3 m in diameter. In embodiments, the solid support includes wells that are from about 0.3 µm to about 3 µm in diameter. In embodiments, the solid support includes wells that are from about 0.4 m to about 3 µm in diameter. In embodiments, the solid support includes wells that are from about 0.5 µm to about 3 µm in diameter. In embodiments, the solid support includes wells that are from about 0.6 µm to about 3 µm in diameter. In embodiments, the solid support includes wells that are from about 0.7 µm to about 3 µm in diameter. In embodiments, the solid support includes wells that are from about 0.8 µm to about 3 µm in diameter. In embodiments, the solid support includes wells that are from about 0.9 µm to about 3 µm in diameter. In embodiments, the solid support includes wells that are from about 1.0 µm to about 3 µm in diameter. In embodiments, the solid support includes wells that are from about 0.1 µm to about 2 µm in diameter. In embodiments, the solid support includes wells that are from about 0.2 µm to about 2 m in diameter. In embodiments, the solid support includes wells that are from about 0.3 µm to about 2 µm in diameter. In embodiments, the solid support includes wells that are from about 0.4 m to about 2 µm in diameter. In embodiments, the solid support includes wells that are from about 0.5 µm to about 2 µm in diameter. In embodiments, the solid support includes wells that are from about 0.6 µm to about 2 µm in diameter. In embodiments, the solid support includes wells that are from about 0.7 µm to about 2 µm in diameter. In embodiments, the solid support includes wells that are from about 0.8 µm to about 2 µm in diameter. In embodiments, the solid support includes wells that are from about 0.9 µm to about 2 µm in diameter. In embodiments, the solid support includes wells that are from about 1.0 µm to about 2 µm in diameter. In embodiments, the solid support includes wells that are from about 1.0 µm to about 1.5 µm in diameter. In embodiments, the solid support includes wells that are about 0.1 µm to about 2 µm in depth. In embodiments, the solid support includes wells that are about 0.2 µm to about 2 µm in depth. In embodiments, the solid support includes wells that are about 0.3 µm to about 2 µm in depth. In embodiments, the solid support includes wells that are about 0.4 µm to about 2 µm in depth. In embodiments, the solid support includes wells that are about 0.5 µm to about 2 µm in depth. In embodiments, the solid support includes wells that are about 0.6 µm to about 2 µm in depth. In embodiments, the solid support includes wells that are about 0.7 µm to about 2 µm in depth. In embodiments, the solid support includes wells that are about 0.8 µm to about 2 µm in depth. In embodiments, the solid support includes wells that are about 0.9 µm to about 2 µm in depth. In embodiments, the solid support includes wells that are about 1.0 µm to about 2 µm in depth. In embodiments, the solid support includes wells that are about 0.1 µm to about 1.5 µm in depth. In embodiments, the solid support includes wells that are about 0.2 µm to about 1.5 µm in depth. In embodiments, the solid support includes wells that are about 0.3 µm to about 1.5 µm in depth. In embodiments, the solid support includes wells that are about 0.4 µm to about 1.5 µm in depth. In embodiments, the solid support includes wells that are about 0.5 µm to about 1.5 µm in depth. In embodiments, the solid support includes wells that are about 0.6 µm to about 1.5 µm in depth. In embodiments, the solid support includes wells that are about 0.7 µm to about 1.5 µm in depth. In embodiments, the solid support includes wells that are about 0.8 µm to about 1.5 µm in depth. In embodiments, the solid support includes wells that are about 0.9 µm to about 1.5 µm in depth. In embodiments, the solid support includes wells that are about 1.0 µm to about 1.5 µm in depth. In embodiments, one or more wells are different sizes (e.g., one population of wells are 1.0 µm in diameter, and a second population are 0.5 µm in diameter). In embodiments, the solid support is a glass slide about 75 mm by about 25 mm.

In some embodiments, the wells of the array are separated from each other by about 0.7 m to about 1.5 µm. In some embodiments, the wells of the array are separated from each other by at least or at most 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm. In some embodiments, the wells of the array are from about 0.2 µm to about 3 µm in diameter, and wherein the wells of the array are about 0.1 µm to about 2 µm in depth. In some embodiments, the wells of the array are from about 0.2 µm to about 2 µm in diameter, and wherein the wells of the array are about 0.5 µm to about 1.5 µm in depth. In some embodiments, the wells of the array are from about 0.5 µm to about 2 µm in diameter, and wherein the wells of the array are about 0.5 µm to about 1.5 µm in depth. Each well of the multiwell container is capable of retaining a volume of liquid. For example, the volume of the wells can be at least about $1 \times 10^{-3}$ µm$^3$, about $1 \times 10^{-2}$ µm$^3$, about 0.1 µm$^3$, about 1 µm$^3$, about 10 µm$^3$, about 100 µm$^3$, or more. In embodiments, the volume of the wells can be at most about $1 \times 10^4$ µm$^3$, about $1 \times 10^3$ µm$^3$, about 100 µm$^3$, about 10 µm$^3$, about 1 µm$^3$, about 0.1 µm$^3$, or less. In embodiments, the depth of the well is measured from the bottom of the well to the top of the array. In embodiments, the depth of the well is measured from the bottom of the well to the top of the interstitial region. In embodiments, the depth of the well is measured from the bottom of the well to the top of the photoresist. In embodiments, the array is a nanoarray which can have nanowells having a diameter sufficient to allow only one particle into the well. It is understood that the size of the nanowell will be dependent upon the size of the particle. In some embodiments, the diameter of the nanowells are less than 700 nm, less than 600 nm, less than 500 nm, less than 400 nm, less than 300 nm, less than 200 nm, or less than 100 nm. It is also understood that the size of the wells on the array can be of various sizes and will ultimately depend on the systems and/or apparatus used to analyze later reactions.

In embodiments, density of wells on the solid support may be tuned. For example, in embodiments, the multiwell container includes a density of at least about 100 wells per mm$^2$, about 1,000 wells per mm$^2$, about 0.1 million wells per mm$^2$, about 1 million wells per mm$^2$, about 2 million wells per mm$^2$, about 5 million wells per mm$^2$, about 10 million wells per mm$^2$, about 50 million wells per mm$^2$, or more. In embodiments, the multiwell container includes no more than about 50 million wells per mm$^2$, about 10 million wells per mm$^2$, about 5 million wells per mm$^2$, about 2 million wells per mm$^2$, about 1 million wells per mm$^2$, about 0.1 million wells per mm$^2$, about 1,000 wells per mm$^2$, about 100 wells per mm$^2$, or less.

In embodiments, the wells are separated from each other by interstitial regions. In embodiments, the interstitial regions include a polymer layer as described herein (e.g., an amphiphilic copolymer). In embodiments, the solid support further includes a photoresist, wherein the photoresist does not contact the bottom of the well. In embodiments, the polymer layer is substantially free of oligonucleotide moieties. In embodiments, the solid support does not include a polymer (e.g., the solid support is a patterned glass slide). In embodiments, the wells do not include a polymer (e.g., an amphiphilic polymer as described herein) prior to particle loading. In some embodiments, the interstitial regions are substantially free of oligonucleotide moieties. In some embodiments, the interstitial regions are substantially free of particles. In embodiments, the interstitial regions are substantially free of polynucleotides. In embodiments, the interstitial regions are substantially free of a polymer. In embodiments, the interstitial regions include a photoresist.

In some embodiments, greater than 50%, 60%, 70%, 80%, 90% or 95% of the wells include a particle. In some embodiments, greater than 50% of the wells include a particle. In some embodiments, greater than 60% of the wells include a particle. In some embodiments, greater than 70% of the wells include a particle. In some embodiments, greater than 80% of the wells include a particle. In some embodiments, greater than 90% of the wells include a particle. In some embodiments, greater than 90%, 91%, 92%, 93%, 94%, 95%, 96%, 97%, 98%, or 99% of the wells include a particle. In some embodiments, about 50%, 60%, 70%, 80%, 90% or 95% of the wells include a particle. In some embodiments, about 50% of the wells include a particle. In some embodiments, about 60% of the wells include a particle. In some embodiments, about 70% of the wells include a particle. In some embodiments, about 80% of the wells include a particle. In some embodiments, about 90% of the wells include a particle. In some embodiments, about 90%, 91%, 92%, 93%, 94%, 95%, 96%, 97%, 98%, or 99% of the wells include a particle. In embodiments, each well includes one particle. In embodiments, each well include 10 to 100 nanoparticles (e.g., the diameter of the well is 5 mm). In embodiments, greater than 90% of the wells of the solid support contain a particle.

In embodiments, each well contains a plurality of particles (e.g., wherein the well is at least twice the diameter of the longest dimension of the particle). In embodiments, each well is referred to as a feature. In embodiments, the arrays include about 10,000,000 features/cm$^2$ to about 5,000,000,000 features/cm$^2$. In embodiments, the arrays include about 100,000,000 features/cm$^2$ to about 1,000,000,000 features/cm$^2$. In embodiments, the arrays include about 100,000 features/cm$^2$ to about 100,000,000 features/cm$^2$. In embodiments, the arrays include about or about 10,000,000 features/cm$^2$ to about 50,000,000 features/cm$^2$.

In embodiments, the wells have a mean or median separation from one another of about 0.5-5 µm. In embodiments, the mean or median separation is about 0.1-10 µm, 0.25-5 µm, 0.5-2 µm, 1 µm, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm or a number or a range between any two of these values. In embodiments, the mean or median separation is about or at least about 0.1 µm. In embodiments, the mean or median separation is about or at least about 0.2 µm. In embodiments, the mean or median separation is about or at least about 0.3 µm. In embodiments, the mean or median separation is about or at least about 0.4 µm. In embodiments, the mean or median separation is about or at least about 0.5 µm. In embodiments, the mean or median separation is about or at least about 0.6 µm. In embodiments, the mean or median separation is about or at least about 0.7 µm. In embodiments, the mean or median separation is about or at least about 0.8 µm. In embodiments, the mean or median separation is about or at least about 0.9 µm. In embodiments, the mean or median separation is about or at least about 1.0 µm. In embodiments, the mean or median separation is about or at least about 1.1 µm. In embodiments, the mean or median separation is about or at least about 1.2 µm. In embodiments, the mean or median separation is about or at least about 1.3 µm. In embodiments, the mean or median separation is about or at least about 1.4 µm. In embodiments, the mean or median separation is about or at least about 1.5 µm. In embodiments, the mean or median separation is about or at least about 1.6 µm. In embodiments, the mean or median separation is about or at least about 1.7 µm. In embodiments, the mean or median separation is about or at least about 1.8 µm. In embodiments, the mean or median separation is about or at least about 1.9 µm. In embodiments, the mean or median separation is about or at least about 2.0 µm. In embodiments, the mean or median separation is about or at least about 2.1 µm. In embodiments, the mean or median separation is about or at least about 2.2 µm. In embodiments, the mean or median separation is about or at least about 2.3 µm. In embodiments, the mean or median separation is about or at least about 2.4 µm. In embodiments, the mean or median separation is about or at least about 2.5 µm. In embodiments, the mean or median separation is about or at least about 2.6 µm. In embodiments, the mean or median separation is about or at least about 2.7 µm. In embodiments, the mean or median separation is about or at least about 2.8 µm. In embodiments, the mean or median separation is about or at least about 2.9 µm. In embodiments, the mean or median separation is about or at least about 3.0 µm. In embodiments, the mean or median separation is about or at least about 3.1 µm. In embodiments, the mean or median separation is about or at least about 3.2 µm. In embodiments, the mean or median separation is about or at least about 3.3 µm. In embodiments, the mean or median separation is about or at least about 3.4 µm. In embodiments, the mean or median separation is about or at least about 3.5 µm. In embodiments, the mean or median separation is about or at least about 3.6 µm. In embodiments, the mean or median separation is about or at least about 3.7 µm. In embodiments, the mean or median separation is about or at least about 3.8 µm. In embodiments, the mean or median separation is about or at least about 3.9 µm. In embodiments, the mean or median separation is about or at least about 4.0 µm. In embodiments, the mean or median separation is about or at least about 4.1 µm. In embodiments, the mean or median separation is about or at least about 4.2 µm. In embodiments, the mean or median separation is about or at least about 4.3 µm. In embodiments, the mean or median separation is about or at least about 4.4 µm. In embodiments, the mean or median separation is about or at least about 4.5 µm. In embodiments, the mean or median separation is about or at least about 4.6 µm. In embodiments, the mean or median separation is about or at least about 4.7 µm. In embodiments, the mean or median separation is about or at least about 4.8 µm. In embodiments, the mean or median separation is about or at least about 4.9 µm. In embodiments, the mean or median separation is about or at least about 5.0 µm. The mean or median separation may be measured center-to-center (i.e., the center of one well to the center of a second well). In embodiments of the methods provided herein, the wells have a mean or median separation (measured center-to-center) from one another of about 0.5-5 µm. The mean or median separation may be measured edge-to-edge (i.e., the edge of well to the edge of a second well). In embodiments, the wells have a mean or median separation (measured edge-to-edge) from one another of about 0.2-1.5 µm. In embodiments, the wells have a mean or median separation (measured center-to-center) from one another of about 0.7-1.5 µm.

Neighboring features of a solid support (e.g., array) can be discrete one from the other in that they do not overlap. Accordingly, the features can be adjacent to each other or separated by a gap (e.g., an interstitial space). In embodiments where features are spaced apart, neighboring sites can be separated, for example, by a distance of less than 10 µm, 5 µm, 1 µm, 0.9 µm, 0.8 µm, 0.7 µm, 0.6 µm, 0.5 m or less. The layout of features on an array can also be understood in terms of center-to-center distances between neighboring features. A solid support useful in the invention can have neighboring features with center-to-center spacing of less than about 10 µm, 5 µm, 1 µm, 0.9 µm, 0.8 µm, 0.7 µm, 0.6 µm, 0.5 µm, 0.4 m or less. In embodiments, the solid support has neighboring features with center-to-center spacing of less than about 10 µm. In embodiments, the solid support has neighboring features with center-to-center spacing of less than about 5 µm. In embodiments, the solid support has neighboring features with center-to-center spacing of less than about 1 µm. In embodiments, the solid support has neighboring features with center-to-center spacing of less than about 0.9 µm. In embodiments, the solid support has neighboring features with center-to-center spacing of less than about 0.8 µm. In embodiments, the solid support has neighboring features with center-to-center spacing of less than about 0.7 µm. In embodiments, the solid support has neighboring features with center-to-center spacing of less than about 0.6 µm. In embodiments, the solid support has neighboring features with center-to-center spacing of less than about 0.5 µm. In embodiments, the solid support has neighboring features with center-to-center spacing of less than about 0.4 µm. Furthermore, it will be understood that the distance values described above and elsewhere herein can represent an average distance between neighboring features of a solid support. As such, not all neighboring features need to fall in the specified range unless specifically indicated to the contrary, for example, by a specific statement that the distance constitutes a threshold distance between all neighboring features of an array.

The solid supports for some embodiments have at least one surface located within a flow cell. Flow cells provide a convenient format for housing an array of clusters produced by the methods described herein, in particular when subjected to an SBS or other detection technique that involves repeated delivery of reagents in cycles.

In embodiments, the solid support is subjected to lithographic patterning methods (e.g., nanolithographic to microlithographic patterning). Typically, features smaller than 10 micrometers are considered microlithographic, and features smaller than 100 nanometers are considered nanolithographic. Lithographic techniques make use of masks or templates to transfer patterns over a large area simultaneously. A powerful microfabrication technique is photolithography, i.e. the lithography using a UV light source and a photosensitive material as resist.

In embodiments, the solid support includes a photoresist. In embodiments, the wells are separated from each other by interstitial regions. In embodiments, the solid support further includes a photoresist, wherein the photoresist does not contact the bottom of the well. As the name suggests, the photoresist (alternatively referred to as a resist) is an active material layer that can be patters by selective exposure and must "resist" chemical/physical attach of the underlying substrate. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly(vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276). In embodiments, the solid support includes a photoresist and polymer layer, wherein the photoresist is between the solid support and the polymer layer (e.g., as depicted in FIGS. 2A-2C). In embodiments, the photoresist is on the interstitial areas and not the surface of the wells. Suitable photoresist compositions are known in the art, such as, for example the compositions and resins described in U.S. Pat. Nos. 6,897,012; 6,991,888; 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer. In embodiments, the resist is an amorphous (non-crystalline) fluoropolymer (e.g., CYTOP® from Bellex), a crystalline fluoropolymer, or a fluoropolymer having both amorphous and crystalline domains. In embodiments, the resist is a suitable polysiloxane, such as polydimethylsiloxane (PDMS).

In some embodiments, the solid support includes a hydrophobic polymer layer. In embodiments, the solid support includes a perfluorinated polymer. In embodiments, the solid support includes a polyfluorinated polymer. In embodiments, the solid support includes polymerized units of a fluorine-containing methacrylate (e.g., $CH_2=C(CH_3)COOC-(CF_3)_2CF_2CF_2CF_3$). Non-limiting examples and synthetic protocols of fluorine-containing methacrylate monomers may be found in Zhang, D., (2018). Materials (Basel, Switzerland), 11(11), 2258 (2018), which is incorporated herein by reference. In embodiments, the fluorinated polymer is an amorphous (non-crystalline) fluoropolymer (e.g., CYTOP® from Bellex), a crystalline fluoropolymer, or a fluoropolymer having both amorphous and crystalline domains.

In embodiments, the solid support includes a polymer layer. In embodiments, the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

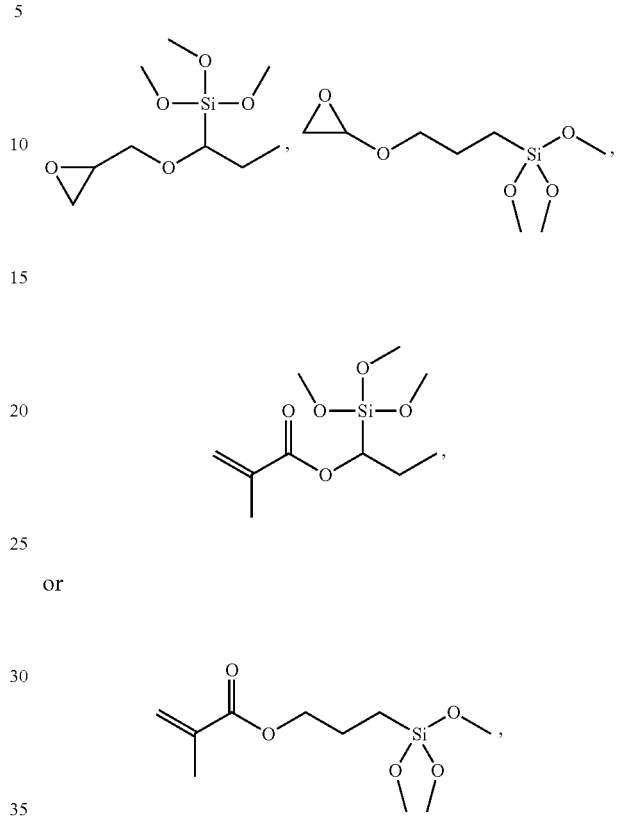

or a copolymer thereof.

In embodiments, the polymer layer includes polymerized units of alkoxysilyl polymers having the formula:

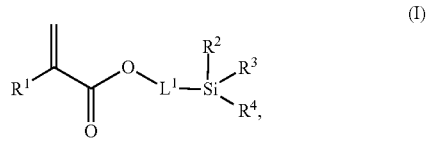

(I)

wherein $R^1$ is H or methyl; $R^2$, $R^3$, and $R^4$ are each independently substituted or unsubstituted alkyl or substituted or unsubstituted heteroalkyl, wherein at least one of $R^2$, $R^3$, and $R^4$ includes an alkoxy bond to the Si atom; and $L^1$ is substituted or unsubstituted alkylene or substituted or unsubstituted heteroalkylene. In embodiments, the polymer layer further includes polymerized units of polyethylene glycol methacrylate (PEGMA), polyethylene glycol acrylate (PEGA), sulfobetaine acrylate (SBA), carboxybetaine acrylate (CBA), phosphorylcholine acrylate (PCA), sulfobetaine methacrylate (SBMA), carboxybetaine methacrylate (CBMA), or phosphorylcholine methacrylate (PCMA). In embodiments, $R^1$ is H. In embodiments, $R^1$ is unsubstituted methyl. In embodiments, the polymer layer is an organically-modified ceramic polymer. In embodiments, the polymer includes polymerized monomers of alkoxysilyl polymers, such as

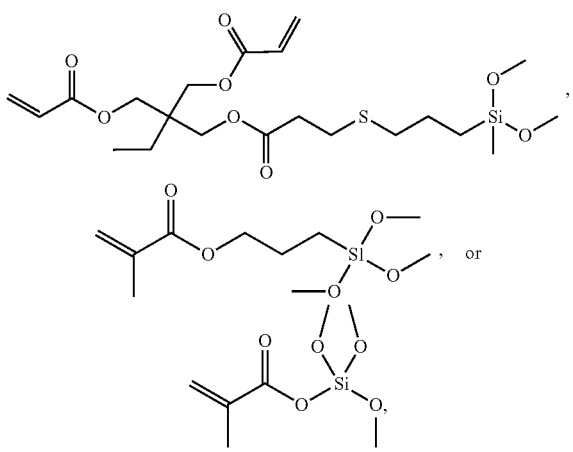

embodiments, the polymer layer includes one or more ceramic particles, (e.g., silicates, aluminates, and titanates). In embodiments, the polymer layer includes titanium dioxide, zinc oxide, and/or iron oxide.

In embodiments, $R^2$ is $R^{2A}$—substituted or unsubstituted alkyl (e.g., $C_1$-$C_{20}$, $C_{10}$-$C_{20}$, $C_1$-$C_8$, $C_1$-$C_6$, or $C_1$-$C_4$), or $R^{2A}$—substituted or unsubstituted heteroalkyl (e.g., 2 to 20, 8 to 20, 2 to 10, 2 to 8, 2 to 6, or 2 to 4 membered). In embodiments, $R^2$ is substituted or unsubstituted alkyl (e.g., $C_1$-$C_{20}$, $C_{10}$-$C_{20}$, $C_1$-$C_8$, $C_1$-$C_6$, or $C_1$-$C_4$), or substituted or unsubstituted heteroalkyl (e.g., 2 to 20, 8 to 20, 2 to 10, 2 to 8, 2 to 6, or 2 to 4 membered).

In embodiments, $R^2$ is unsubstituted —O—$C_1$-$C_6$ or —O-$C_1$-$C_4$ alkyl. In embodiments, $R^2$ is unsubstituted —O—$C_1$-$C_4$ alkyl. In embodiments, $R^2$ is unsubstituted —O—$C_1$-$C_6$ alkyl. In embodiments, $R^2$ is unsubstituted —O—methyl. In embodiments, $R^2$ is unsubstituted —O—$C_2$ alkyl. In embodiments, $R^2$ is unsubstituted —O—$C_3$ alkyl. In embodiments, $R^2$ is unsubstituted —O—$C_4$ alkyl. In embodiments, $R^2$ is unsubstituted —O—$C_5$ alkyl. In embodiments, $R^2$ is unsubstituted —O—$C_6$ alkyl. In embodiments, $R^2$ is $R^{2A}$—substituted —O—$C_1$-$C_6$ or —O—$C_1$-$C_4$ alkyl. In embodiments, $R^2$ is $R^{2A}$—substituted —O—$C_1$-$C_4$ alkyl. In embodiments, $R^2$ is $R^{2A}$—substituted —O—$C_1$-$C_6$ alkyl. In embodiments, $R^2$ is $R^{2A}$—substituted —O—methyl. In embodiments, $R^2$ is $R^{2A}$—substituted —O—$C_2$ alkyl. In embodiments, $R^2$ is $R^{2A}$—substituted —O—$C_3$ alkyl. In embodiments, $R^2$ is $R^{2A}$—substituted —O—$C_4$ alkyl. In embodiments, $R^2$ is $R^{2A}$—substituted —O—$C_5$ alkyl. In embodiments, $R^2$ is $R^{2A}$—substituted —O—$C_6$ alkyl. In embodiments, $R^2$ is $R^{2A}$—substituted 2 to 10 membered heteroalkyl. In embodiments, $R^2$ is $R^{2A}$—substituted 2 to 8 membered heteroalkyl. In embodiments, $R^2$ is $R^{2A}$—substituted 2 to 6 membered heteroalkyl. In embodiments, $R^2$ is $R^{2A}$—substituted 2 to 4 membered heteroalkyl. In embodiments, $R^2$ is an unsubstituted 2 to 10 membered heteroalkyl. In embodiments, $R^2$ is an unsubstituted 2 to 8 membered heteroalkyl. In embodiments, $R^2$ is an unsubstituted 2 to 6 membered heteroalkyl. In embodiments, $R^2$ is an unsubstituted 2 to 4 membered heteroalkyl.

$R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{2A}$ is —OH.

In embodiments, $R^3$ is $R^{3A}$—substituted or unsubstituted alkyl (e.g., $C_1$-$C_{20}$, $C_{10}$-$C_{20}$, $C_1$-$C_8$, $C_1$-$C_6$, or $C_1$-$C_4$), or $R^{3A}$—substituted or unsubstituted heteroalkyl (e.g., 2 to 20, 8 to 20, 2 to 10, 2 to 8, 2 to 6, or 2 to 4 membered). In embodiments, $R^3$ is substituted or unsubstituted alkyl (e.g., $C_1$-$C_{20}$, $C_{10}$-$C_{20}$, $C_1$-$C_8$, $C_1$-$C_6$, or $C_1$-$C_4$), or substituted or unsubstituted heteroalkyl (e.g., 2 to 20, 8 to 20, 2 to 10, 2 to 8, 2 to 6, or 2 to 4 membered).

In embodiments, $R^3$ is unsubstituted —O—$C_1$-$C_6$ or —O—$C_1$-$C_4$ alkyl. In embodiments, $R^3$ is unsubstituted —O—$C_1$-$C_4$ alkyl. In embodiments, $R^3$ is unsubstituted —O—$C_1$-$C_6$ alkyl. In embodiments, $R^3$ is unsubstituted —O—methyl. In embodiments, $R^3$ is unsubstituted —O—$C_2$ alkyl. In embodiments, $R^3$ is unsubstituted —O—$C_3$ alkyl. In embodiments, $R^3$ is unsubstituted —O—$C_4$ alkyl. In embodiments, $R^3$ is unsubstituted —O—$C_5$ alkyl. In embodiments, $R^3$ is unsubstituted —O—$C_6$ alkyl. In embodiments, $R^3$ is $R^{3A}$—substituted —O—$C_1$-$C_6$ or —O—$C_1$-$C_4$ alkyl. In embodiments, $R^3$ is $R^{3A}$—substituted —O—$C_1$-$C_4$ alkyl. In embodiments, $R^3$ is $R^{3A}$—substituted —O—$C_1$-$C_6$ alkyl. In embodiments, $R^3$ is $R^{3A}$—substituted —O—methyl. In embodiments, $R^3$ is $R^{3A}$—substituted —O—$C_2$ alkyl. In embodiments, $R^3$ is $R^{3A}$—substituted —O—$C_3$ alkyl. In embodiments, $R^3$ is $R^{3A}$—substituted —O—$C_4$ alkyl. In embodiments, $R^3$ is $R^{3A}$—substituted —O—$C_5$ alkyl. In embodiments, $R^3$ is $R^{3A}$—substituted —O—$C_6$ alkyl. In embodiments, $R^3$ is $R^{3A}$—substituted 2 to 10 membered heteroalkyl. In embodiments, $R^3$ is $R^{3A}$—substituted 2 to 8 membered heteroalkyl. In embodiments, $R^3$ is $R^{3A}$—substituted 2 to 6 membered heteroalkyl. In embodiments, $R^3$ is $R^{3A}$—substituted 2 to 4 membered heteroalkyl. In embodiments, $R^3$ is an unsubstituted 2 to 10 membered heteroalkyl. In embodiments, $R^3$ is an unsubstituted 2 to 8 membered heteroalkyl. In embodiments, $R^3$ is an unsubstituted 2 to 6 membered heteroalkyl. In embodiments, $R^3$ is an unsubstituted 2 to 4 membered heteroalkyl.

$R^{3A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{3A}$ is —OH.

In embodiments, $R^4$ is $R^{4A}$—substituted or unsubstituted alkyl (e.g., $C_1$-$C_{20}$, $C_{10}$-$C_{20}$, $C_1$-$C_8$, $C_1$-$C_6$, or $C_1$-$C_4$), or $R^{4A}$—substituted or unsubstituted heteroalkyl (e.g., 2 to 20, 8 to 20, 2 to 10, 2 to 8, 2 to 6, or 2 to 4 membered). In embodiments, $R^4$ is substituted or unsubstituted alkyl (e.g., $C_1$-$C_{20}$, $C_{10}$-$C_{20}$, $C_1$-$C_8$, $C_1$-$C_6$, or $C_1$-$C_4$), or substituted or unsubstituted heteroalkyl (e.g., 2 to 20, 8 to 20, 2 to 10, 2 to 8, 2 to 6, or 2 to 4 membered).

In embodiments, $R^4$ is unsubstituted —O—$C_1$-$C_6$ or —O—$C_1$-$C_4$ alkyl. In embodiments, $R^4$ is unsubstituted —O—$C_1$-$C_4$ alkyl. In embodiments, $R^4$ is unsubstituted —O—$C_1$-$C_6$ alkyl. In embodiments, $R^4$ is unsubstituted —O—methyl. In embodiments, $R^4$ is unsubstituted —O—$C_2$ alkyl. In embodiments, $R^4$ is unsubstituted —O—$C_3$ alkyl. In embodiments, $R^4$ is unsubstituted —O—$C_4$ alkyl.

In embodiments, $R^4$ is unsubstituted —O—$C_5$ alkyl. In embodiments, $R^4$ is unsubstituted —O—$C_6$ alkyl. In embodiments, $R^4$ is $R^{4A}$—substituted —O—$C_1$-$C_6$ or —O—$C_1$-$C_4$ alkyl. In embodiments, $R^4$ is $R^{4A}$—substituted —O—$C_1$-$C_4$ alkyl. In embodiments, $R^4$ is $R^{4A}$—substituted —O—$C_1$-$C_6$ alkyl. In embodiments, $R^4$ is $R^{4A}$—substituted —O—methyl. In embodiments, $R^4$ is $R^{4A}$—substituted —O—$C_2$ alkyl. In embodiments, $R^4$ is $R^{4A}$—substituted —O—$C_3$ alkyl. In embodiments, $R^4$ is $R^{4A}$—substituted —O—$C_4$ alkyl. In embodiments, $R^4$ is $R^{4A}$—substituted —O—$C_5$ alkyl. In embodiments, $R^4$ is $R^{4A}$—substituted —O—$C_6$ alkyl. In embodiments, $R^4$ is $R^{4A}$—substituted 2 to 10 membered heteroalkyl. In embodiments, $R^4$ is $R^{4A}$—substituted 2 to 8 membered heteroalkyl. In embodiments, $R^4$ is $R^{4A}$—substituted 2 to 6 membered heteroalkyl. In embodiments, $R^4$ is $R^{4A}$—substituted 2 to 4 membered heteroalkyl. In embodiments, $R^4$ is an unsubstituted 2 to 10 membered heteroalkyl. In embodiments, $R^4$ is an unsubstituted 2 to 8 membered heteroalkyl. In embodiments, $R^4$ is an unsubstituted 2 to 6 membered heteroalkyl. In embodiments, $R^4$ is an unsubstituted 2 to 4 membered heteroalkyl.

$R^{4A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{4A}$ is —OH.

In embodiments, $L^1$ is $R^{1A}$-substituted or unsubstituted alkylene (e.g., $C_1$-$C_{20}$, $C_{10}$-$C_{20}$, $C_1$-$C_8$, $C_1$-$C_6$, or $C_1$-$C_4$), or $R^{1A}$-substituted or unsubstituted heteroalkylene (e.g., 2 to 20, 8 to 20, 2 to 10, 2 to 8, 2 to 6, or 2 to 4 membered). In embodiments, $L^1$ is substituted or unsubstituted alkylene (e.g., $C_1$-$C_{20}$, $C_{10}$-$C_{20}$, $C_1$-$C_8$, $C_1$-$C_6$, or $C_1$-$C_4$), or substituted or unsubstituted heteroalkylene (e.g., 2 to 20, 8 to 20, 2 to 10, 2 to 8, 2 to 6, or 2 to 4 membered).

In embodiments, $L^1$ is unsubstituted $C_1$-$C_6$ or $C_1$-$C_4$ alkylene. In embodiments, $L^1$ is unsubstituted $C_1$-$C_4$ alkylene. In embodiments, $L^1$ is unsubstituted $C_1$-$C_6$ alkylene. In embodiments, $L^1$ is unsubstituted methylene. In embodiments, $L^1$ is unsubstituted $C_2$ alkylene. In embodiments, $L^1$ is unsubstituted $C_3$ alkylene. In embodiments, $L^1$ is unsubstituted $C_4$ alkylene. In embodiments, $L^1$ is unsubstituted $C_5$ alkylene. In embodiments, $L^1$ is unsubstituted $C_6$ alkylene. In embodiments, $L^1$ is $R^{1A}$-substituted $C_1$-$C_6$ or $C_1$-$C_4$ alkylene. In embodiments, $L^1$ is $R^{1A}$-substituted $C_1$-$C_4$ alkylene. In embodiments, $L^1$ is $R^{1A}$-substituted $C_1$-$C_6$ alkylene. In embodiments, $L^1$ is $R^{1A}$-substituted methylene. In embodiments, $L^1$ is $R^{1A}$-substituted $C_2$ alkylene. In embodiments, $L^1$ is $L^{1A}$-substituted $C_3$ alkylene. In embodiments, $L^1$ is $R^{LA}$—substituted $C_4$ alkylene. In embodiments, $L^1$ is $R^{1A}$-substituted $C_5$ alkylene. In embodiments, Li is $L^{1A}$-substituted $C_6$ alkylene. In embodiments, $L^1$ is $R^{1A}$-substituted 2 to 10 membered heteroalkylene. In embodiments, $L^1$ is $R^{1A}$-substituted 2 to 8 membered heteroalkylene. In embodiments, $L^1$ is $R^{1A}$-substituted 2 to 6 membered heteroalkylene. In embodiments, $L^1$ is $R^{LA}$—substituted 2 to 4 membered heteroalkylene. In embodiments, $L^1$ is an unsubstituted 2 to 10 membered heteroalkylene. In embodiments, $L^1$ is an unsubstituted 2 to 8 membered heteroalkylene. In embodiments, Li is an unsubstituted 2 to 6 membered heteroalkylene. In embodiments, $L^1$ is an unsubstituted 2 to 4 membered heteroalkylene.

$R^{1A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{1A}$ is —$CH_3$.

In embodiments, the polymer layer attached to the solid support includes polymerized units of 3-(trimethoxysilyl)propyl methacrylate (TMSPM)

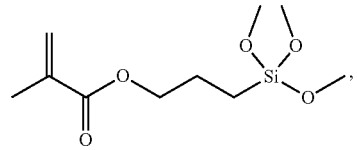 [SMILES: C=C(C)C(=O)OCCC[Si](OC)(OC)OC]

3a (trimethoxysilyl)propyl methacrylate (TMSPA)

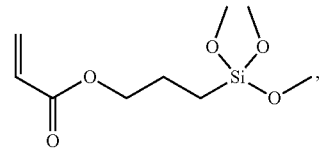

3-(triethoxysilyl)propyl methacrylate (TESPM),

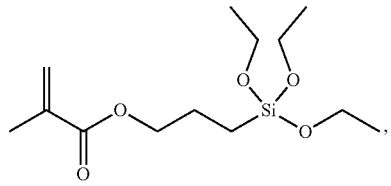 [SMILES: C=C(C)C(=O)OCCC[Si](OCC)(OCC)OCC]

83

3-(triethoxysilyl)propyl acrylate (TESPA)

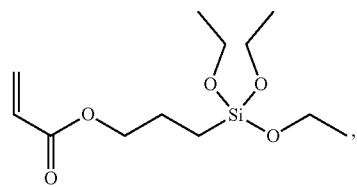 [SMILES: C=CC(=O)OCCC[Si](OCC)(OCC)OCC], 3-(dimethoxy(1-methylethoxy)silyl]propyl methacrylate (

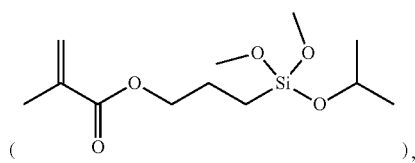 [SMILES: C=C(C)C(=O)OCCC[Si](OC)(OC)OC(C)C]), 3-(ethoxydimethoxysilyl)propyl 2-methyl-2-propenoate (

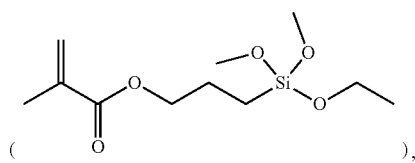 [SMILES: C=C(C)C(=O)OCCC[Si](OC)(OC)OCC]), 3-(Tripropoxysilyl)propyl 2-methyl-2-propenoate

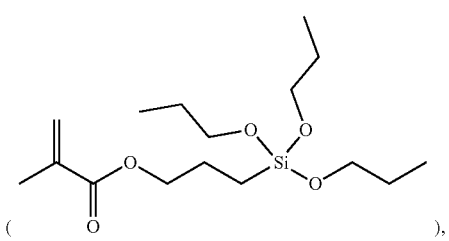,

2-Methyl-3-(triethoxysilyl)propyl 2-methyl-2-propenoate

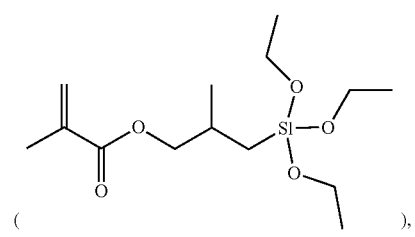,

84

3-(Methyldipropoxysilyl)propyl 2-methyl-2-propenoate

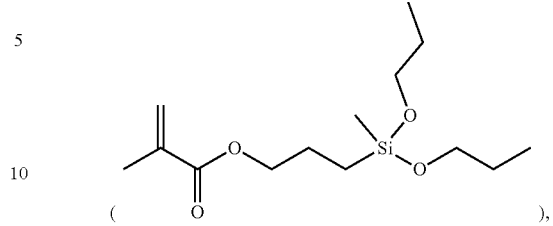, 3-(Diethoxymethylsilyl)propyl 2-methyl-2-propenoate

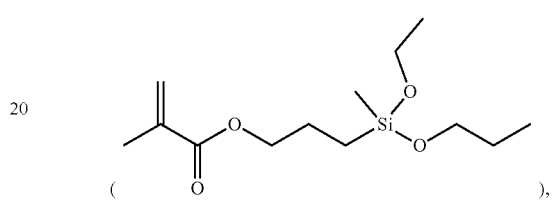,

3-[Diethoxy(2-hydroxyethoxy)silyl]propyl 2-methyl-2-propenoate

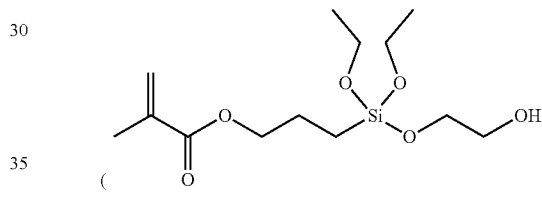, or 3-(Butyldimethoxysilyl)propyl 2-methyl-2-propenoate

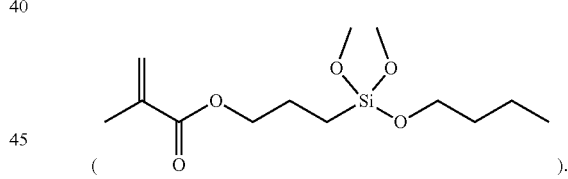.

In embodiments, the polymer coating includes polymerized units of glycidyloxypropyl trimethoxysilane (GPTMS). In embodiments, the polymer coating includes polymerized units of alkoxysilyl polymers and polymerized units of polyethylene glycol methacrylate (PEGMA).

In embodiments, the solid support includes a photoresist, alternatively referred to herein as a resist. A "resist" as used herein is used in accordance with its ordinary meaning in the art of lilthography and refers to a polymer matrix (e.g., a polymer network). In embodiments, the photoresist is a silsesquioxane resist, an epoxy-based polymer resist, poly (vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist.

In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, $Al_2O_3$, $TiO_2$ or $Ta_2O_5$). In embodiments, the photoresist includes metal atoms, such as Si, Zr, Mg, Al, Ti or Ta atoms. In embodiments, the solid support is a glass slide about 75 mm by about 25 mm. In embodiments, the solid support includes a resist (e.g., a photoresist or nanoimprint resist including a crosslinked polymer matrix attached to the solid support).

In embodiments, prior to contacting the solid support with a plurality of particles, the solid support is subjected to lithographic patterning methods (e.g., nanolithographic to microlithographic patterning). Typically, features smaller than 10 micrometers are considered microlithographic, and features smaller than 100 nanometers are considered nanolithographic. Lithographic techniques make use of masks or templates to transfer patterns over a large area simultaneously. A powerful microfabrication technique is photolithography, i.e. the lithography using a UV light source and a photosensitive material as resist. As the name suggests, the photoresist (alternatively referred to as a resist) is an active material layer that can be patterned by selective exposure and must "resist" chemical/physical attach of the underlying substrate. In embodiments, the resist is a crosslinked polymer matrix. In embodiments, the resist includes silsesquioxane molecules. In embodiments, the resist includes polymerized epoxy-containing monomers, or polymerized poly(vinylpyrrolidone-vinyl acrylic acid) copolymers. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly(vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276). In embodiments, the resist is removed prior to loading. Alternatively, in embodiments, the resist includes the plurality of wells and remains in contact with the solid support while contacting the support with a plurality of particles.

In embodiments, the solid support includes a photoresist. A photoresist is a light-sensitive polymer material used to form a patterned coating on a surface. The process begins by coating a substrate (e.g., a glass substrate) with a light-sensitive organic material. A mask with the desired pattern is used to block light so that only unmasked regions of the material will be exposed to light. In the case of a positive photoresist, the photo-sensitive material is degraded by light and a suitable solvent will dissolve away the regions that were exposed to light, leaving behind a coating where the mask was placed. In the case of a negative photoresist, the photosensitive material is strengthened (either polymerized or cross-linked) by light, and a suitable solvent will dissolve away only the regions that were not exposed to light, leaving behind a coating in areas where the mask was not placed. In embodiments, the solid support includes an epoxy-based photoresist (e.g., SU-8, SU-8 2000, SU-8 3000, SU-8 GLM2060). In embodiments, the solid support includes a negative photoresist. Negative refers to a photoresist whereby the parts exposed to UV become cross-linked (i.e., immobilized), while the remainder of the polymer remains soluble and can be washed away during development. In embodiments, the solid support includes an Off-stoichiometry thiol-enes (OSTE) polymer (e.g., an OSTE resist). In embodiments, the solid support includes a Hydrogen Silsesquioxane (HSQ) polymer (e.g., HSQ resist). In embodiments, the solid support includes a crosslinked polymer matrix on the surface of the wells and the interstitial regions.

In embodiments, the solid support includes a nanoimprint resist. In embodiments, the solid support includes a photoresist and polymer layer, wherein the photoresist is between the solid support and the polymer layer (e.g., as depicted in FIGS. 1A-IC). In embodiments, the photoresist is on the interstitial areas and not the surface of the wells. Suitable photoresist compositions are known in the art, such as, for example the compositions and resins described in U.S. Pat. Nos. 6,897,012; 6,991,888; 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer. In embodiments, the resist is an amorphous (non-crystalline) fluoropolymer (e.g., CYTOP® from Bellex), a crystalline fluoropolymer, or a fluoropolymer having both amorphous and crystalline domains. In embodiments, the resist is a suitable polysiloxane, such as polydimethylsiloxane (PDMS).

In embodiments, the solid support includes a resist (e.g., a nanoimprint lithography (NIL) resist). Nanoimprint resists can include thermal curable materials (e.g., thermoplastic polymers), and/or UV-curable polymers. In embodiments, the solid support is generated by pressing a transparent mold possessing the pattern of interest (e.g., the pattern of wells) into photo-curable liquid film, followed by solidifying the liquid materials via a UV light irradiation. Typical UV-curable resists have low viscosity, low surface tension, and suitable adhesion to the glass substrate. For example, the solid support surface, but not the surface of the wells, is coated in an organically modified ceramic polymer (ORMOCER®, registered trademark of Fraunhofer-Gesellschaft zur Forderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference. In embodiments, the solid support surface, and the surface of the wells, is coated in an organically modified ceramic polymer (ORMOCER®, registered trademark of Fraunhofer-Gesellschaft zur Forderung der angewandten Forschung e. V. in Germany). In embodiments, the resist (e.g., the organically modified ceramic polymer) is not removed prior to particle deposition. In embodiments, the wells are within the resist polymer and not the solid support.

In embodiments, the wells are separated from each other by interstitial regions including a polymer layer as described herein (e.g., an amphiphilic copolymer). In embodiments, the solid support further includes a photoresist, wherein the photoresist does not contact the bottom of the well. In embodiments, the solid support does not include a polymer (e.g., the solid support is a patterned glass slide). In embodiments, the wells do not include a polymer (e.g., an amphiphilic polymer as described herein) prior to particle loading. In embodiments, the solid support further includes a photoresist, wherein the photoresist is in contact with the bottom of the well and the interstitial space. In embodiments, the polymer layer is substantially free of oligonucleotide moieties (e.g., oligonucleotide moieties are not covalently bound to the solid support and/or the polymer layer, including the interstitial space). In embodiments, the wells include a polymer (e.g., an amphiphilic polymer and/or resist as described herein) prior to particle loading.

In embodiments, the solid support includes a passivated polymer layer (alternatively referred to as a passivated polymer coating). In embodiments, the solid support includes a passivated polymer layer, wherein the passivated polymer layer includes an amphiphilic copolymer. The term "amphiphilic copolymer" is used in accordance with its ordinary meaning and refers to a copolymer composed of polymerized hydrophilic (e.g., PEG monomers and hydrophobic monomers (e.g., alkoxysilyl or (poly(propylene oxide) monomers). The term "amphiphilic copolymer" is used in accordance with its ordinary meaning and refers to a copolymer composed of polymerized hydrophilic (e.g., PEG monomers or HEMA monomers) and hydrophobic monomers (e.g., alkoxysilyl or (poly(propylene oxide) monomers).

Amphiphilic copolymers can have both hydrophilic and hydrophobic properties. In embodiments, the polymer layer includes an amphiphilic acrylate copolymer or amphiphilic methacrylate copolymer.

In embodiments, the amphiphilic (co)polymer includes a poloxamer. In some embodiments, the solid support includes a poloxamer layer. In some embodiments, the poloxamer is a polyoxyethylene-polyoxypropylene copolymers. In some embodiments, the poloxamer is poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, and poloxamer 407. In embodiments, the poloxamer is poloxamer 184, poloxamer 188, poloxamer 338, or poloxamer 407 (also known as F127).

In embodiments, the solid support includes a passivated polymer layer, wherein the passivated polymer layer includes a brush copolymer or a comb polymer. A comb polymer includes a main polymer chain with two or more three-way branch points and linear side chains.

A brush polymer includes a main polymer chain with linear, unbranched side chains and where one or more of the branch points has four-way functionality or larger. In embodiments, the passivated polymer layer does not include oligonucleotide moieties. In embodiments, the passivated polymer layer is substantially free of oligonucleotides. In embodiments, the passivated polymer layer does not include oligonucleotide capture moieties. In embodiments, the passivated polymer layer binds to the resist of the array. In embodiments, nucleic acid content is not transferred to the solid support, rather the oligonucleotide moieties are localized to the polymer shell of the particle.

In some embodiments, the solid support includes a hydrophobic polymer layer. In embodiments, the solid support includes a perfluorinated polymer. In embodiments, the solid support includes a polyfluorinated polymer. In embodiments, the solid support includes polymerized units of a fluorine-containing methacrylate (e.g., $CH_2{=}C(CH_3)COOC{-}(CF_3)_2CF_2CF_2CF_3$). Non-limiting examples and synthetic protocols of fluorine-containing methacrylate monomers may be found in Zhang, D., (2018). Materials (Basel, Switzerland), 11(11), 2258 (2018), which is incorporated herein by reference. In embodiments, the fluorinated polymer is an amorphous (non-crystalline) fluoropolymer (e.g., CYTOP® from Bellex), a crystalline fluoropolymer, or a fluoropolymer having both amorphous and crystalline domains.

In some embodiments, the solid support includes a hydrophilic polymer layer. In some embodiments, the hydrophilic polymer is a silane functionalized polymer. In some embodiments, the silane functionalized polymer is a silane functionalized polyethylene glycol (Si-PEG) polymer or a silane functionalized poly(acrylamide) (Si-PAm).

In embodiments, the passivated polymer layer or the amphiphilic polymer includes polymerized units of alkoxysilyl polymers. In embodiments, the passivated polymer layer includes polymerized units of alkoxysilyl polymers (e.g., TMSPM) and polymerized units of polyethylene glycol methacrylate (PEGMA. In embodiments, the amphiphilic copolymer includes polymerized units of alkoxysilyl polymers and polymerized units of polyethylene glycol methacrylate (PEGMA), or polyethylene glycol acrylate (PEGA). In embodiments, the amphiphilic copolymer includes polymerized units of 3-(trimethoxysilyl)propyl methacrylate (TMSPM), 3-(trimethoxysilyl)propyl methacrylate (TMSPA) and polymerized units of polyethylene glycol methacrylate (PEGMA), or polyethylene glycol acrylate (PEGA). In embodiments, the amphiphilic copolymer includes polymerized units of 3-(trimethoxysilyl)propyl methacrylate (TMSPM) and polymerized units of polyethylene glycol methacrylate (PEGMA). In embodiments, the amphiphilic copolymer includes polymerized units of 3-(trimethoxysilyl)propyl methacrylate (TMSPM), polymerized units of polyethylene glycol methacrylate (PEGMA) and polymerized units of hydroxyethylmethacrylate (HEMA). In embodiments, the amphiphilic copolymer includes polymerized units of polyethylene glycol methacrylate (PEGMA) and polymerized units of hydroxyethylmethacrylate (HEMA).

In an aspect is provided a microfluidic device including the solid support which includes a particle and/or plurality of particles as described herein. In embodiments, the microfluidic device includes a flow cell. In embodiments, the microfluidic device includes an imaging system or detection apparatus. Any of a variety of detection apparatus can be configured to detect the reaction vessel or solid support where reagents interact. Examples include luminescence detectors, surface plasmon resonance detectors and others known in the art.

Exemplary systems having fluidic and detection components that can be readily modified for use in a system herein include, but are not limited to, those set forth in U.S. Pat. Nos. 8,241,573, 8,039,817; or US Pat. App. Pub. No. 2012/0270305 A1, each of which is incorporated herein by reference. In embodiments, the microfluidic device further includes one or more excitation lasers.

In embodiments, the microfluidic device is a nucleic acid sequencing device including: a stage configured to hold an array or solid support as described herein, including embodiments; an array or solid support as described herein, including embodiments; and a detector for obtaining sequencing data. In some embodiments, the detector is an imaging detector, such as a CCD, EMCCD, or s-CMOS detector.

Nucleic acid sequencing devices utilize excitation beams to excite labeled nucleotides in the DNA containing sample to enable analysis of the base pairs present within the DNA. Many of the next-generation sequencing (NGS) technologies use a form of sequencing by synthesis (SBS), wherein modified nucleotides are used along with an enzyme to read the sequence of DNA templates in a controlled manner. In embodiments, sequencing includes a sequencing by synthesis event, where individual nucleotides are identified iteratively (e.g., incorporated and detected into a growing complementary strand), as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'—OH group available to direct further sequence extension and therefore the polymerase cannot add further nucleotides. Once the identity of the base incorporated into the growing chain has been determined, the 3' reversible terminator may be removed to allow addition of the next successive nucleotide. In embodiments, the nucleic acid sequencing device utilizes the detection of four different nucleotides that include four different labels.

The term "nucleic acid sequencing device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Singular Genomics™ such as the G4™ sequencing platform, Illumina™, Inc. (e.g., HiSeq™ MiSeq™, NextSeq™, or NovaSeq™ systems), Life Technologies™ (e.g., ABI PRISM™, or SOLiD™ systems), Pacific Biosciences (e.g., systems using SMRT™ Technology such as the Sequel™ or RS II™ systems), or Qiagen (e.g., Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or $(NH_4)_2SO_4$)), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9- trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/ or a solid-state imaging device. The solid-state imaging device may include a charge coupled device (CCD) and/or a complementary metal oxide semiconductor (CMOS).

The system may also include circuitry and processors, including systems using microcontrollers, reduced instruction set computers (RISC), application specific integrated circuits (ASICs), field programmable gate array (FPGAs), logic circuits, and any other circuit or processor capable of executing functions described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the device includes a thermal control assembly useful to control the temperature of the reagents.

In an aspect is a kit, including the solid support as described herein. In an aspect is provided a kit, including the plurality of particles as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes an array with particles already loaded into the wells. In embodiments, the particles are in a container. In embodiments, the particles are in aqueous suspension or as a powder within the container. The container may be a storage device or other readily usable vessel capable of storing and protecting the particles. The kit may also include a flow cell. In embodiments, kit includes the solid support and a flow cell carrier (e.g., a flow cell carrier as described in US 2021/0190668, which is incorporated herein by reference for all purposes).

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol µ DNA polymerase, Pol X DNA polymerase, Pol σ DNA polymerase, Pol α DNA polymerase, Pol δ DNA polymerase, Pol ε DNA polymerase, Pol η DNA polymerase, Pol t DNA polymerase, Pol κ DNA polymerase, Pol λ DNA polymerase, Pol γ DNA polymerase, Pol θ DNA polymerase, Pol ν DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution (e.g., the degrading agent) can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can include one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In an aspect is provided a kit, including the array as described herein. In an aspect is provided a kit, including the solid support as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes an array with particles already loaded into the wells. In embodiments, the particles are in a container. In embodiments, the particles are in aqueous suspension or as a powder within the container. The container may be a storage device or other readily usable vessel capable of storing and protecting the particles. The kit may also include a flow cell. In embodiments, kit includes the solid support and a flow cell carrier (e.g., a flow cell carrier as described in US 2021/0190668, which is incorporated herein by reference for all purposes).

In an aspect is provided a kit, including the plurality of particles as described herein. Generally, the kit includes one or more containers providing a composition and one or more additional reagents (e.g., a buffer suitable for polynucleotide extension).

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol t DNA polymerase, Pol κ DNA polymerase, Pol λ DNA polymerase, Pol γ DNA polymerase, Pol θ DNA polymerase, Pol ν DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant $P.$ $abyssi$ polymerase (e.g., such as a mutant $P.$ $abyssi$ polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

III. Methods

In an aspect is provided a method of attaching an oligonucleotide to a solid support. In embodiments, the method includes: contacting the solid support with a particle including a degradable particle core and a polymer shell attached to the particle core (e.g., surrounding or encapsulating a substantial portion of the particle core), wherein the polymer shell includes a first bioconjugate reactive moiety covalently linked to the polymer shell; contacting the particle with a degrading agent thereby decomposing the degradable particle core and forming a polymer composition (i.e., the remnant of the polymer shell following decomposition of the particle core) attached to solid support; and contacting the first bioconjugate reactive moiety with an oligonucleotide including a second bioconjugate reactive moiety and forming a bioconjugate linker, thereby attaching the oligonucleotide to the solid support. In embodiments, the method further includes contacting the solid support (e.g., a nanopatterned glass slide or a multiwell container including a plurality of wells) with a plurality of the particles. For example, the method includes contacting the solid support with a plurality of particles, wherein each particle includes a degradable particle core and a polymer shell attached to the particle core.

In embodiments, the method further includes contacting the solid support with a plurality of the oligonucleotides and attaching a plurality of nucleotides to the solid support. In embodiments, the method includes attaching a first plurality (e.g., a plurality of oligonucleotides including a first sequence, such as a first amplification primer sequence, or a complement thereof) and a second plurality (e.g., a plurality of oligonucleotides including a second sequence, such as a second amplification primer sequence, or a complement thereof).

In embodiments, the method includes contacting the solid support with a particle including a degradable particle core and a polymer shell attached to the particle core (e.g., surrounding or encapsulating a substantial portion of the particle core), wherein the polymer shell includes an oligonucleotide moiety covalently linked to the polymer shell; contacting the particle with a degrading agent thereby decomposing the degradable particle core and forming a polymer composition including the oligonucleotide moiety (i.e., the remnant of the polymer shell following decomposition of the particle core) attached to solid support, thereby attaching the oligonucleotide to the solid support. In embodiments, the particle includes a plurality of oligonucleotides. In embodiments decomposing does not include melting. In embodiments, decomposing includes dissolving the degradable particle core.

In embodiments, the method includes: contacting the solid support with a particle including a pH-sensitive particle core and a polymer shell attached to the particle core at a first pH, wherein the polymer shell includes a first bioconjugate reactive moiety covalently linked to the polymer shell; contacting the particle with an acid or base (i.e., decreasing or increasing the pH) thereby decomposing the pH-sensitive particle core and forming a polymer composition (i.e., the remnant of the polymer shell following decomposition of the particle core) attached to solid support; and contacting the first bioconjugate reactive moiety with an oligonucleotide including a second bioconjugate reactive moiety and forming a bioconjugate linker, thereby attaching the oligonucleotide to the solid support. In embodiments, the method includes increasing the pH (e.g., increasing the pH to 8.0, 9.0, 10.0, 11.0, 12.0, or higher) thereby degrading the pH-sensitive particle core. In embodiments, the method includes decreasing the pH (e.g., decreasing the pH to 6.0, 5.0, 4.0, 3.0, 2.0 or 1.0, or lower) thereby degrading the pH-sensitive particle core.

In embodiments, the first pH is a neutral pH. In embodiments, the first pH is about 6.5 to about 7.5. In embodiments, the first pH is about 7.0. In embodiments, the first pH is about 7.1.

In embodiments, the first pH is about 7.2. In embodiments, the first pH is about 7.3. In embodiments, the first pH is about 7.4. In embodiments, the first pH is about 7.5. In embodiments, the second pH is 1.0, 2.0, 3.0, 4.0, 5.0, or 6.0. In embodiments, the second pH is 8.0, 9.0, 10.0, 11.0, or 12.0.

In embodiments, the method includes: contacting the solid support with a particle including a pH-sensitive particle core and a polymer shell attached to the particle core at a first pH, wherein the polymer shell includes an oligonucleotide moiety covalently linked to the polymer shell; contacting the particle with an acid or base solution (i.e., decreasing or increasing the pH) thereby decomposing the pH-sensitive particle core and forming a polymer composition (i.e., the remnant of the polymer shell following decomposition of the particle core) attached to solid support, thereby attaching the oligonucleotide to the solid support.

In embodiments, one or more particles are attached to a surface inside a well (e.g., the bottom or axial walls within the well). In embodiments, one or more particles are attached to a surface outside a well (e.g., the interstitial space outside a well). In embodiments, one or more particles are directly or indirectly attached to the solid support, yet are not within the well of the solid support. In embodiments, a plurality of particles contacts the solid support and a portion of the plurality of particles are contained within the wells and a portion of the plurality of particles are outside of the wells. In embodiments, the method includes removing the particles not attached to, or not within, a well. For example, the method includes removing the one or more particles attached to the surface outside a well. Degrading or dissolving the degradable particle core deposits the polymer shell at (or around) the location of the particle. Thus, if the particles are outside of the wells, if a degrading agent contacts the particles prior to removing particles the particles outside of the wells, the polymer will be deposited and attached to interstitial space, permitting oligonucleotide attachment outside of the wells. In embodiments, the particles not within the wells are removed prior to contacting the solid support and/or the particles with the degrading agent.

The particles not deposited within wells may be removed from the solid support via physical means (e.g., polishing with a cleaning article, such as a lens wipe, towel, squeegee, or brush). For example, a physical force may be deployed to remove the particles from the interstitial space while retaining particles that are trapped inside the wells of the support. The physical force may include applying a linear motion (e.g., applying downward pressure with a lens wipe) that pushes particles off the interstitial space of the support. This may aid to remove the particles in the interstitial space between wells, enabling only particles and polymer are present inside of the wells and the interstitial space is void of particles/polymer. In embodiments, the interstitial space (i.e., the space between the wells) is substantially free of polymer shell. Other forces for removal from the interstitial space could include a circular motion to brush particles off, or a hydrodynamic flow force that washes the particles away without removing particles from the wells (e.g., laminar flow, or if particles are sufficiently trapped, turbulent flow as well). In embodiments, removing includes polishing the solid support with a cleaning article.

In embodiments, removing includes washing the solid support with an aqueous solution to remove particles not deposited within the wells.

In embodiments, wherein the solid support is a multiwell container including a plurality of wells, greater than 50%, 60%, 70%, 80%, 90% or 95% of the wells include one or more particles. In embodiments, 50% of the wells include one or more particles. In embodiments, 55% of the wells include one or more particles. In embodiments, 60% of the wells include one or more particles. In embodiments, 65% of the wells include one or more particles. In embodiments, 70% of the wells include one or more particles. In embodiments, 75% of the wells include one or more particles. In embodiments, 80% of the wells include one or more particles.

In embodiments, 85% of the wells include one or more particles. In embodiments, 90% of the wells include one or more particles. In embodiments, 95% of the wells include one or more particles. In embodiments, 98% of the wells include one or more particles. In embodiments, 99% of the wells include one or more particles. In embodiments, 100% of the wells include one or more particles. In embodiments, the space between the wells is substantially free of particles.

In embodiments, the oligonucleotide is covalently attached to the particle shell prior to contacting the particle with a degrading agent. In embodiments, the oligonucleotide is covalently attached to the particle shell after contacting the particle with a degrading agent.

In embodiments, the degradable particle core is a metal-organic framework (MOF) core. In embodiments, the MOF core is a Isoreticular Metal-Organic Framework (IR-MOF) core, Zeolitic Imidazolate Framework (ZIF) core, Porous Coordination Network (PCN) core, Materials Institute Lavoisier (MIL) MOF core, Porous Coordination Polymer (PCP) core, or University of Oslo (UiO) MOF core. In embodiments, the MOF core is an Isoreticular Metal-Organic Framework (IR-MOF) core. In embodiments, the MOF core is Zeolitic Imidazolate Framework (ZIF) core. In embodiments, the MOF core is Porous Coordination Network (PCN) core. In embodiments, the MOF core is Materials Institute Lavoisier (MIL) MOF core. In embodiments, the MOF core is Porous Coordination Polymer (PCP) core. In embodiments, the MOF core is a University of Oslo (UiO) MOF core. In embodiments, the MOF core is a Northwestern University (NU) MOF core. In embodiments, the MOF core is a Hong Kong University of Science and Technology (HKUST-n) core.

In embodiments, the MOF particle is synthesized by joining metal-containing units, also known as secondary building units (SBUs), with organic linkers using reticular synthesis. In embodiments, the MOF particle may vary in size and nature of its structure without changing its underlying topology. In embodiments, the MOF particle may be post-synthetically modified so that organic units and metal-organic complexes may be incorporated by reactions with linkers so that the reactivity of the pores is changed. In embodiments, the MOF particle may be multivariate wherein multiple organic functionalities are incorporated within a single framework. Isoreticular MOFs (IR-MOF) are synthesized by [Zn4O]6+SBU and a series of aromatic carboxylates. IR-MOFs are octahedral microporous crystalline materials. Zeolitic imidazolate frameworks are synthesized using various elements that have valence electrons and imidazole derivatives. They are zeolite topological structured materials. ZIFs include ZIF-8, ZIF-90, ZIF-L, ZIF-71, ZIF-67, and ZIF-7. Porous coordination networks are stereo-octahedron materials, and they have a hole-cage-hole topology with a 3D structure. Some of the PCNs are PCN-333, PCN-224, PCN-222, and PCN-57. Materials Institute Lavoisier MOFs (MIL MOFs) are synthesized using elements that have valence electrons and an organic compound containing two carboxylic functional groups. The pore size arrangement of MIL MOFs could be converted freely under outward incitement. MIL MOFs contain MIL-101, MIL-100, MIL-53, MIL-88, MIL-125, etc. Porous coordination polymer materials are synthesized by carboxylic acid, pyridine, and its derivative as the PBU and transition metal ions as the SBU. University of Oslo MOF based on dicarboxylic acid as the PBU and Zr6(μ3-O)4(μ3-OH) as the SBU.

In embodiments, the MOF particle is MOF-5; MOF-177 [$Zn_4O(BTB)_2$ wherein BTB=4, 4',4''-benzene-1,3,5-triyl-bribenzoate]; MOF-200 [$Zn_4O(BBC)_2$ wherein $BBC^{3-}$ is 4,4',4''-(benzene-1,3,5-triyl-tris(benzene-4,1-diyl)tribenzoate]; MOF-210 [$(Zn_4O)_3(BTE)_4(BPDC)_3$ wherein BTE=4, 4',4''-(benzene-1,3,5-triyl-tris(ethyne-2,1-diyl))tribenzoate and BPDC=bipheyl-4,4'-dicarboxylate]; NU-110[$Cu_3$(BHEHPI) wherein $BHEHPI^{6-}$ is 5,5',5''-((((benzene-1,3,5-triyltris(benzene-4,1-diyl))tris(ethyne-2,1-diyl))-tris(benzene-4,1,-diyl))tris(ethyne-2,1-diyl))triisophthalate]; IRMOF-1; IRMOF-16 [$Zn_4O(TPDC)_3$ wherein $TPDC^{2-}$ is terphenyl-5,5''-dicarboxylate]; MOF-180 [$Zm_4O(BTE)_2$], HKUST-1 [$Cu_3(BTC)_2$ wherein $BTC^{3-}$ is benzene-1,3,5-tricarboxylate]; MOF-399 [$Zn_3(TPBTM)$ wherein $TPBTM^{6-}$ is 5,5',5''-((benzene-1,3,5-tricarbonyl)tris(azanediyl))tri-isophthalate]; $Cu_3(TPBTM)$; $Cu_3(TDPAT)$ wherein $TDPAT^{6-}$ is 5,5',5''-(1,3,5-triazine-2,4,6-triyl)tris(azanediyl) triisophthalate; NOTT-112 [$Cu_3(BTPI)$] wherein $BTPI^{6-}$ is 5,5',5''-(benzene-1,3,5-triyl-tris)benzene-4,1-diyl))triisophthalate]; NOTT-116, also known as PCN-68, [$Cu_3(PTEI)$ wherein $PTEI^{6-}$ is 5,5',5''-((benzene-1,3,5-triyl-trisbenzene-4,1-diyl)tris(ethyne-2,1-diyl))triisophthalate]; PCN-61 [$Cu_3$(BTEI) wherein $BTEI^{6-}$ is 5,5',5''-(benzene-1,3,5-triyl-tris(ethyne-2,1-diyl))triisophthalate]; PCN-66 [$Cu_3(NTEI)$ wherein $NTEI^{6-}$ is 5,5',5''-((nitrilotris(benzene-4,1-diyl))tris(ethyne-2,1-diyl))triisophthalate]; PCN-69, also known as NOTT-119, [$Cu_3(BTTI)$ wherein $BTTI^{6-}$ is 5,5',5''=(benzene-1,3,5-triyl-tris(biphenyl-4,4'-dyl))triisophthalate]; PCN-610, also known as NU-100, [$Cu_3(TTEI)$ wherein $TTEI^{6-}$ is 5,5',5''-(((benzene-1,3,5-triyl-tris(ethyne-2,1-diyl))tris(benzene-4,1-diyl))tris(ethyne-2,1-diyl))triisophthalate]; NU-108 [$Cu_3(BTETCA)$ wherein $BTETCA^{6-}$ is 5,5''''',5'''''-(benzene-1,3,5-triyl-tris(ethyne-2,1-diyl))tris(([1,1':3'1''-terphenyl]-4,4''-dicarboxylate))]; NU-109 [$Cu_3$(BNETPI) wherein $BNETPI^{6-}$ is 5,5',5''-(((benzene-1,3,5-triyl-tris(ethyne-2,1-diyl))tris(benzene-4,1-diyl))tris(buta-1,3-diyne-4,1-diyl))triisophthalate]; NU-110 and NU-111 [$Cu_3(BHEI)$, wherein $BHEI^{6-}$ is 5,5',5''-(benzene-1,3,5-ytiyl-tris(buta-1,3-diyne-4,1-diyl))triisophthalate]. In embodiments, the MOF particle is $M_3(BTC)_2$ wherein M is Zn(II), Fe(II), Mo(II), Cr(II) and Ru(II), MOF-74 [$M_2(DOT)$ wherein DOT is dioxidoterephthalate using divalent metal ions such as Mg, Co, Ni and Mn and $M^{2+}$ is Zn or Mg]. In embodiments, the MOF particle is IRMOF-74-I, IRMOF-74-II, IRMOF-74-III, IRMOF-74-IV, IRMOF-74-V, IRMOF-74-VI, IRMOF-74-VII, IRMOF-74-VIII, IRMOF-74-IX, IRMOF-74-X and IRMOF-74-XI. In embodiments, the MOF particle is MTV-MOF-5, $Ag_6(OH_2)(H_2O_4)$ $(TIPA)_5$, PCN-14, MOF-2, MOF-11, MOF-73 or POST-1. In embodiments the MOF particle is UiO-66, MOT-525, MOF-545, MOF-11, IRMOF-3, UMCM-I-$NH_2$, MIL-101, Mn-BTT, MOF-48, PIZA-3, MIL-101(Cr), MIL-53, MIL-68, MOF-5, NU-100, Ni-MOF-74, Mg-MOF-74, Fe-MOF-74, MOF-508, MOF-1001, CPM-7 or CPM-24. In embodiments, the MOF particle is MOF-LIC-1, DMOF-1, UMCM-1, ZIF-90, STAM-1, SNU-30, CAU-1, or SIM-1. In embodiments the MOF particle is ZIF-8, also known as $Zn(MIm)_2$ wherein MIm is 2-methylimidazolate.

In embodiments, the MOF particle core is MOF-5 (e.g., Cu-MOF-5, Co-MOF-5, MOF-74 (e.g., Co-MOF-74, Mg-MOF-74, Cu-MOF-74, Zn-MOF-74, or Ni-MOF-74), Cu-BTC (i.e., copper benzene-1,3,5-tricarboxylate (BTC)), HKUST-1 (Hong Kong University of Science and Technology-1), IRMOF-1, IRMOF-3, MIL-100, MIL-100(Fe), MIL-101 (e.g., MIL-101(Cr)), MIL-125 (e.g., MIL-125 (Ti)), MIL-140A, MIL-53 (e.g., MIL-53(Al)), MOF-177, MOF-199, MOF-5, MOF-808 (e.g., MOF-808(Co), MOF-808(Mn), MOF-808(Ni), or MOF-808(Zn)) NOTT-202, NOTT-202 (Nano-Organic-Templated Tecto-Framework-202), NU-1000 (Nanjing University-1000), PCN-14, PCN-222, PCN-222, PCN-224, PCN-225, PCN-227, PCN-244, PCN-245, PCN-250, UiO-66 (University of Oslo-66), UiO-67, UiO-68, UiO-69, UiO-70, UiO-71, ZIF-8 (Zinc Imidazolate Framework-8), or ZIF-90. In embodiments, the MOF is ZIF-8, a zinc-based MOF that is sensitive to pH changes, wherein MOF framework collapses when exposed to acidic conditions or basic conditions, resulting in the release of zinc ions and degradation of the carrier scaffold. In embodiments, the MOF is MOF-5, a magnesium-based MOF that is sensitive to pH changes, wherein the MOF framework collapses when exposed to acidic conditions or basic conditions, resulting in the release of magnesium ions and degradation of the carrier scaffold. In embodiments, the MOF is MIL-100(Fe), an iron-based MOF that is sensitive to pH changes. The MOF framework collapses when exposed to acidic conditions or basic conditions, resulting in the release of iron ions and degradation of the carrier scaffold. In embodiments, the MOF is PCN-222, a copper-based MOF that is sensitive to pH changes. The MOF framework collapses when exposed to acidic conditions or basic conditions, resulting in the release of copper ions and degradation of the carrier scaffold. In embodiments, the MOF is UiO-66, a zinc-based MOF that is sensitive to pH changes. The framework collapses when exposed to acidic conditions or basic, resulting in the release of zinc ions and degradation of the carrier scaffold.

In embodiments, the degradable particle core is a polystyrene (PS) particle, or polymethyl methacrylate (PMMA) particle, or latex particle.

In embodiments, the polymer shell may be referred to as a particle shell, polymer film, polymer composition, and the like. In embodiments, the polymer shell includes polyacrylamide (AAm), poly(N-(5-azidoacetamidylpentyl)acrylamide-co-acrylamide (PAZAM), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly (lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, glycidyl methacrylate (GMA), glycidyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes polyacrylamide (AAm), glicydyl methacrylate (GMA), polyethylene glycol methacrylate (PEGMA), polyethylene glycol acrylate (PEGA), isocyanatoethyl methacrylate (IEM), or a copolymer thereof.

In embodiments, the particle shell includes polyacrylamide (AAm), poly-N-isopropylacrylamide, poly N-isopropylpolyacrylanide, polyethylene glycol acrylate, methacrylate, polyacrylic acid, poly(hydroxyethyl methacrylate) (PHEMA), poly(methyl methacrylate) (PMMA), poly(N-isopropylacrylamide) (PNIPAAm), glicydyl nethacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes poly(hydroxyethyl methacrylate) (PHEMA), poly(methyl methacrylate) (PMMA), poly(N-isopropylacrylarnide) (PNIPAAm), glicydyl methacrylate (GMA), glicydyl methacrylate (GMA) azide, hydroxyethylmethacrylate (HEMA), hydroxyethylacrylate (HEA), hydroxypropylnethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide.

In embodiments, the particle shell includes polymerized units of polyethylene glycol methacrylate (PEGMA) and glicydyl methacrylate (GMA) azide. In embodiments, the ratio of GMA azide to PEGMA is about 1:1, 1:2, 1:3, 1:4, 1:5, 1:6, 1:7 or about 1:8.

In some embodiments, the polymer shell includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the polymer shell includes polymerized units of polyacrylamide (AAm), glicydyl methacrylate (GMA), polyethylene glycol methacrylate (PEGMA), polyethylene glycol methacrylate (PEGMA), isocyanatoethyl methacrylate (IEM), or a copolymer thereof. In embodiments, the polymer shell includes polymerized units of polyethylene glycol methacrylate (PEGMA) and glicydyl methacrylate (GMA). In embodiments, the polymer shell includes polymerized units of polyethylene glycol methacrylate (PEGMA) and isocyanatoethyl methacrylate (IEM). In embodiments, the polymer shell includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the polymer shell includes polymerized units of 3-azido-2-hydroxypropyl methacrylate, 2-azido-3-hydroxypropyl methacrylate, or 2-(((2-azidoethoxy)carbonyl) amino)ethyl methacrylate. In embodiments, the polymer shell includes polymerized units of 3-azido-2-hydroxypropyl methacrylate. In embodiments, the polymer shell includes polymerized units of 3-azido-2-hydroxypropyl methacrylate 2-azido-3-hydroxypropyl methacrylate. In embodiments, the polymer shell includes polymerized units of 3-azido-2-hydroxypropyl methacrylate 2-(((2-azidoethoxy)carbonyl)amino)ethyl methacrylate.

In embodiments, the polymer shell includes a copolymer of two or more of the following polymerizable monomers, wherein at least one of the polymerizable monomers includes a bioconjugate reactive moiety: polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/ N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly (N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), and/or isocyanatoethyl methacrylate (IEM).

In some embodiments, the particle polymer includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis (acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle polymer includes polymerized units of polyethylene glycol methacrylate (PEGMA) and glicydyl methacrylate (GMA). In embodiments, the particle polymer includes polymerized units of polyethylene glycol methacrylate (PEGMA) and isocyanatoethyl methacrylate (IEM). In embodiments, the particle polymer includes polymerized units of glicydyl methacrylate azide (GMA azide) and polyethylene glycol methacrylate (PEGMA). In embodiments, the ratio of GMA azide to PEGMA is 1:1. In embodiments, the ratio of GMA azide to PEGMA is 1:2. In embodiments, the ratio of GMA azide to PEGMA is 1:3. In embodiments, the ratio of GMA azide to PEGMA is 1:4. In embodiments, the ratio of GMA azide to PEGMA is 1:5. In embodiments, the ratio of GMA azide to PEGMA is 1:6. In embodiments, the ratio of GMA azide to PEGMA is 1:7. In embodiments, the ratio of GMA azide to PEGMA is 1:8. In embodiments, the particle polymer includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle polymer includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the particle polymer includes polymerized units of 3-azido-2-hydroxypropyl methacrylate. In embodiments, the particle polymer includes polymerized units of 3-azido-2-hydroxypropyl methacrylate 2-azido-3-hydroxypropyl methacrylate. In embodiments, the particle polymer includes polymerized units of 3-azido-2-hydroxypropyl methacrylate 2-(((2-azidoethoxy)carbonyl)amino)ethyl methacrylate. In embodiments, the particle polymer includes polymerized units of a) polyethylene glycol methacrylate (PEGMA) and glicydyl methacrylate (GMA), b) polyethylene glycol methacrylate (PEGMA) and isocyanatoethyl methacrylate (IEM), or c) polyethylene glycol methacrylate (PEGMA) and glicydyl methacrylate (GMA) azide, wherein the particle core is a silica particle. In embodiments, the particle includes a plurality of particle polymers (e.g., a plurality of polyethylene glycol methacrylate (PEGMA) and glicydyl methacrylate (GMA) azide copolymers). In embodiments, the particle includes a plurality of brush particle polymers. In embodiments, the polymer shell has polymerized units of polyethylene glycol methacrylate (PEGMA) monomer having formula

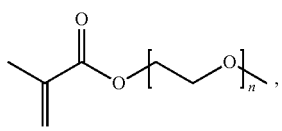

wherein n is 1 to 100. In embodiments, the polymer shell has polymerized units of polyethylene glycol methacrylate (PEGMA) monomer having formula

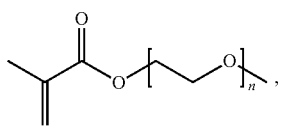

wherein n is 2 to 10. In embodiments, n is 2 to 6. In embodiments, n is 2, 3 or 4. In embodiments, n is 6, 7, 8, 9, 10, 11, or 12.

The polymer may be polymerized from a mixture of functionalized and non-functionalized monomers, such that at least some functionalized monomers that provide attachment points (e.g., azide moieties) for primers (e.g., DBCO-containing oligonucleotide primers) are spaced from one another by one or more monomers lacking such attachment points (e.g., PEG or AAm). The frequency of monomer units attached to primers within a polymer can be adjusted by changing the concentration of the corresponding functionalized monomer in the mixture of monomers. In embodiments, monomer units of the polymer shell that are attached to a polynucleotide primer are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the polymer shell that are attached to a polynucleotide primer (referred to herein as oligonucleotide moieties) are separated by, on average, about or at least about 1, 2, 3, 4, 5, 6, 7, 8, 9, 10, 15, 20, 25, 30, 40, 50, or more monomer units that are not attached to a primer, referred to herein as (ng). In embodiments, monomer units of the polymer shell that are attached to a polynucleotide primer are separated by, on average, about or at least about 4 to 8 monomer units that are not attached to a primer. In embodiments, monomer units of the polymer shell that are attached to a polynucleotide primer are separated by, on average, about 4 to 8 monomer units that are not attached to a primer. In embodiments, monomer units of the polymer shell that are attached to a polynucleotide primer are separated by, on average, about or at least about 6, 7, or 8 monomer units that are not attached to a primer. In embodiments, primer-attached monomers are separated by, on average, about 1-50, 2-40, 3-30, 4-25, or 5-20 monomers not attached to primers. In embodiments, monomer units of the polymer that are attached to a polynucleotide primer are separated by 3 monomer units that are not attached to a primer (referred to as having a degree of polymerization of 3, also referred to as 3 ng). In embodiments, monomer units of the polymer shell that are attached to a polynucleotide primer are separated by 6 ng. In embodiments, monomer units the polymer shell that are attached to a polynucleotide primer are separated by 9 ng. The mixture can include monomers with different functional groups (e.g., azides, alkynes, DBCO, etc.) as described herein.

In embodiments, the method further includes hybridizing a labeled probe to the oligonucleotide and detecting the labeled probe, thereby detecting the oligonucleotide. In embodiments, the method includes binding a DNA binding dye, such as SYBR™ green or SYBR™ gold (available from Thermo Fisher Scientific, Waltham, Mass.) or the alike for use with a Qubit™ fluorometer (e.g., available from Thermo Fisher Scientific, Waltham, Mass.), or PicoGreen™ dye (e.g., available from Thermo Fisher Scientific, Waltham, Mass.) for use on a suitable fluorescence spectrometer or a real-time PCR machine or digital-droplet PCR machine. In embodiments, the method further includes quantifying the target nucleic acid molecule or amplicons (i.e., amplification products thereof). Methods for quantifying a target polynucleotide or amplicon are well known to one skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. Real-Time PCR: Current Technology and Applications, Caister Academic Press. (2009). RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are well known in the art. In embodiments, the method includes hybridizing a probe to the oligonucleotide and detecting the probe. In embodiments, the oligonucleotide moieties are quantified by introducing a nucleic acid stain (FAM (6-fluorescein amidite) labeled oligonucleotide) in the presence of a buffer is allowed to incubate with the oligonucleotides for 10 minutes. After a wash, the substrate containing the stained oligos may be imaged and subjected to post-processing analysis to determine the presence and brightness.

In embodiments, the method includes hybridizing a target polynucleotide (e.g., a target polynucleotide from a library of nucleic acid molecules) to the oligonucleotide and extending with a polymerase the oligonucleotide to form a complement of the target polynucleotide. In embodiments, the method includes amplifying the complement of the target polynucleotide. In embodiments, the method includes amplifying the target polynucleotide and the complement of the target polynucleotide.

In embodiments, amplifying includes of rolling circle amplification (RCA), exponential rolling circle amplification (eRCA), recombinase polymerase amplification (RPA), helicase dependent amplification (HDA), or template walking amplification. In embodiments, amplifying includes thermal bridge polymerase chain reaction (t-bPCR) amplification, chemical bridge polymerase chain reaction (c-bPCR) amplification or chemical-thermal bridge polymerase chain reaction (cT-bPCR) amplification).

In an aspect is provided a method of amplifying a target polynucleotide, the method including contacting the solid support as described herein, including embodiments, with a sample including a target polynucleotide; hybridizing a primer oligonucleotide to the polynucleotide sequence and extending the primer oligonucleotide sequence with a polymerase, thereby amplifying the target polynucleotide to produce an amplification product, wherein amplifying includes extension of the oligonucleotide moiety hybridized to the target polynucleotide.

In embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, amplifying includes a bridge polymerase chain reaction amplification. In embodiments, amplifying includes a thermal bridge polymerase chain reaction (t-bPCR) amplification. In embodiments, amplifying includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions. In embodiments, amplifying includes generating a double-stranded amplification product.

In embodiments, amplifying includes incubation in a denaturant. In embodiments, the denaturant is acetic acid, ethylene glycol, hydrochloric acid, nitric acid, formamide, guanidine, sodium salicylate, sodium hydroxide, dimethyl sulfoxide (DMSO), propylene glycol, urea, or a mixture thereof. In embodiments, the denaturant is an additive that lowers a DNA denaturation temperature. In embodiments, the denaturant is betaine, dimethyl sulfoxide (DMSO), ethylene glycol, formamide, glycerol, guanidine thiocyanate, 4-methylmorpholine 4-oxide (NMO), or a mixture thereof. In embodiments, the denaturant is betaine, dimethyl sulfoxide (DMSO), ethylene glycol, formamide, glycerol, guanidine thiocyanate, or 4-methylmorpholine 4-oxide (NMO).

In embodiments, amplifying includes a plurality of cycles of strand denaturation, primer hybridization, and primer extension. Although each cycle will include each of these three events (denaturation, hybridization, and extension), events within a cycle may or may not be discrete. For example, each step may have different reagents and/or reaction conditions (e.g., temperatures). Alternatively, some steps may proceed without a change in reaction conditions. For example, extension may proceed under the same conditions (e.g., same temperature) as hybridization. After extension, the conditions are changed to start a new cycle with a new denaturation step, thereby amplifying the amplicons. Primer extension products from an earlier cycle may serve as templates for a later amplification cycle. In embodiments, the plurality of cycles is about 5 to about 50 cycles. In embodiments, the plurality of cycles is about 10 to about 45 cycles. In embodiments, the plurality of cycles is about 10 to about 20 cycles. In embodiments, the plurality of cycles is about 20 to about 30 cycles. In embodiments, the plurality of cycles is 10 to 45 cycles. In embodiments, the plurality of cycles is 10 to 20 cycles. In embodiments, the plurality of cycles is 20 to 30 cycles. In embodiments, the plurality of cycles is about 10 to about 45 cycles. In embodiments, the plurality of cycles is about 20 to about 30 cycles. In embodiments, amplifying includes 1 to 60 minutes of solid-phase rolling circle amplification (RCA), solid-phase exponential rolling circle amplification (eRCA), solid-phase recombinase polymerase amplification (RPA), solid-phase helicase dependent amplification (HDA), or template walking amplification. In embodiments, amplifying includes 1 to 100 thermal bridge polymerase chain reaction (t-bPCR) amplification, chemical bridge polymerase chain reaction (c-bPCR) amplification or chemical-thermal bridge polymerase chain reaction (cT-bPCR) amplification). In embodiments, a bridge PCR amplification method produces a first set of amplicons that are complementary to an original template, and a second set of amplicons that have nucleic acid sequences substantially identical to the original template, where both the first and second sets of amplicons are attached to a substrate (e.g., a substrate of a flow cell). In embodiments, amplifying includes 1 to 100 bridge-PCR amplification cycles.

In embodiments, the amplifying occurs at discrete locations in an ordered array of amplification sites on the surface. In some embodiments, the surface does not include an ordered array of amplification sites. For example, the surface may be uniformly coated with amplification primers, rather than coating some areas (amplification sites) and not others (interstitial regions).

In embodiments, the method further includes: (i) hybridizing and extending a first sequencing primer in a first sequencing cycle and detecting one or more labels in a first detection region to generate a sequencing read for the first template polynucleotide, wherein the first sequencing primer is complementary to the first sequencing primer binding sequence, and (ii) hybridizing and extending a second sequencing primer in a second sequencing cycle and detecting one or more labels in a second detection region to generate a sequencing read for the second template polynucleotide, wherein the second sequencing primer is complementary to the second sequencing primer binding sequence.

In an aspect is provided a method of sequencing a polynucleotide, the method including contacting a solid support including two or more wells with the plurality of particles as described herein, including embodiments, thereby depositing one or more particles in a well; contacting the one or more particles with a degrading agent to decompose the degradable particle core; hybridizing a sequencing primer to the oligonucleotide and extending the sequencing primer to incorporate one or more nucleotides; and detecting the incorporated nucleotides. In embodiments, the method includes contacting the particle with a target polynucleotide and amplifying the target polynucleotide.

In an aspect is provided a method of sequencing a template polynucleotide. In embodiments, the method includes contacting a solid support (e.g., a solid support as described herein) with a sample including a template polynucleotide. In embodiments, the method include hybridizing the template polynucleotide to the oligonucleotide moiety. In embodiments, the method includes extending the oligonucleotide moiety to generate a complement of the template polynucleotide immobilized to the particle. In embodiments, the method includes forming a plurality of amplification products by subjecting the solid support to suitable amplification conditions (e.g., as described herein). In embodiments, the method includes contacting the immobilized template polynucleotide, or complement thereof, with a sequencing primer, and with a polymerase, incorporating one or more nucleotides into an extension strand. In embodiments, the method includes detecting the one or more nucleotides incorporated into the extension strand.

In embodiments, sequencing includes hybridizing a sequencing primer to an amplification product, or a complement thereof, incorporating one or more modified nucleotides into the sequencing primer with a polymerase to create an extension strand, and detecting the one or more incorporated nucleotides.

In embodiments, the solid support includes a surface, the surface comprising a plurality of wells separated from each other by interstitial regions on the surface, wherein one or more wells includes a particle, as described herein. In embodiments, the method includes amplifying the target polynucleotide to produce an amplification product, wherein amplifying includes extension of the oligonucleotide moiety hybridized to the target polynucleotide.

In embodiments, the primer oligonucleotide is hybridized to the polynucleotide sequence and extended with a polymerase. The construction of the oligonucleotide primer allows for selective targeting, enabling detection of specific targets within the cell. In embodiments, the oligonucleotide primer includes at least one target-specific region. In embodiments, the oligonucleotide primer includes two target-specific regions. In embodiments, the oligonucleotide primer includes at least one flanking-target region (i.e., an oligonucleotide sequence that flanks the region of interest). In embodiments, the oligonucleotide primer includes two flanking-target regions. A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a target sequence (e.g., a gene of interest). In embodiments, the target-specific region is capable of hybridizing to at least a portion of the target sequence. In embodiments, the target-specific region is substantially non-complementary to other target sequences present in the sample.

In embodiments, the oligonucleotide is about 10 to about 250 nucleotides in length. In embodiments, the oligonucleotide is about 15 to about 60 nucleotides in length. In embodiments, the method includes contacting the particle with a first plurality of oligonucleotides and a second plurality of oligonucleotides, wherein each plurality includes an amplification primer sequence or an amplification primer binding sequence. In embodiments, the sequence of the oligonucleotides of the first plurality is different from the sequence of the oligonucleotides of the second plurality.

In embodiments, the oligonucleotide includes a spatial barcode. In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample. In some embodiments, the spatial barcode includes 10-50 nucleotides. The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter. For example, the spatial barcode may include 10, 11, 12, 13, 14, 15, 16, 17, 18, 19, 20, 21, 22, 23, 24, 25, 26, 27, 28, 29, 30, 31, 31, 32, 33, 34, 35, 36, 37, 38, 39, 40, 41, 42, 43, 44, 45, 46, 47, 48, 49, or 50 nucleotides. In particular embodiments, the spatial barcode includes 20 nucleotides. The spatial barcode can be a first spatial barcode, and the capture probe can include a second spatial barcode different from the first spatial barcode. For multiple capture probes that are attached to a common array feature, the one or more spatial barcode sequences of the multiple capture probes can include sequences that are the same for all capture probes coupled to the feature, and/or sequences that are different across all capture probes coupled to the feature.

In embodiments of the methods provided herein, the contacting step of the template polynucleotide to the oligonucleotide is performed under non-hybridizing conditions. In embodiments of the methods provided herein, the contacting step is performed under non-hybridizing conditions initially, then the conditions are changed to hybridizing conditions. In embodiments of the methods provided herein, the contacting step is performed under hybridizing conditions initially, then the conditions are changed to non-hybridizing conditions. In general, contacting the sample under non-hybridizing conditions can facilitate distribution of target polynucleotides within a polymeric particle prior to subsequent steps (e.g., amplification). Examples of non-hybridizing conditions include but are not limited to low salt, high temperature, and/or presence of additives such as formamide. The precise nature of non-hybridizing conditions (e.g., the temperature, or the amounts of salt or formamide) will vary with factors such as the length, GC-content, or melting temperature (Tm) of primers (or the target-hybridizing portion thereof) present in the reaction. In embodiments, primers are designed to have Tm's within 15, 10, 5, 3 or fewer degrees of one another. In embodiments, non-hybridizing conditions comprises a temperature that is about or at least about 5, 10, 15, 20, or more degrees above the average Tm of primers in the reaction.

In embodiments, amplifying includes a plurality of cycles of strand denaturation, primer hybridization, and primer extension. In embodiments, amplifying includes thermally cycling between (i) about 80-95° C. for about 15-30 sec for denaturation, and (ii) about 50-75° C. for about 1 minute for annealing/extension of the primer. In embodiments, amplifying includes thermally cycling between about 72-80° C. for about 5 seconds to about 30 seconds for denaturation; and (ii) about 60-70° C. for about 30 to 90 seconds for annealing/extension of the primer. In embodiments, amplifying includes thermally cycling between (i) about 67-80° C. for about 5 seconds to about 30 seconds for denaturation; and (ii) about 60-70° C. for about 30 to 90 seconds for annealing/extension of the primer. In embodiments, amplifying includes thermally cycling between about 35° C. and about 65° C. In embodiments, amplifying includes thermally cycling between about 40° C. and about 60° C. In embodiments, amplifying includes thermally cycling between about 40° C. and about 58° C. In embodiments, amplifying includes thermally cycling between about 42° C. and about 62° C. In embodiments, amplifying includes thermally cycling between 35° C. and 65° C. In embodiments, amplifying includes thermally cycling between 40° C. and 60° C. In embodiments, amplifying includes thermally cycling between 40° C. and 58° C. In embodiments, amplifying includes thermally cycling between 42° C. and 62° C. In embodiments, amplifying includes thermally cycling about +/−45° C. In embodiments, amplifying includes thermally cycling about +/−40° C. In embodiments, amplifying includes thermally cycling about +/−35° C. In embodiments, amplifying includes thermally cycling about +/−30° C. In embodiments, amplifying includes thermally cycling about +/−25° C. In embodiments, amplifying includes thermally cycling about +/−20° C. In embodiments, amplifying includes thermally cycling about +/−15° C. In embodiments, amplifying includes thermally cycling about +/−10° C. In embodiments, amplifying includes thermally cycling about +/−5° C. In embodiments, amplifying includes thermally cycling about +/−2° C. In embodiments, the device as described herein is configured to perform amplifying of a target polynucleotide. Primer binding sequences usually have a length in the range of between 3 to 36 nucleotides, also 5 to 24 nucleotides, also from 12 to 36 nucleotides.

In embodiments, the method further includes sequencing the amplification product(s). Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes (i.e., unique for each nucleotide dATP, dTTP, dCTP, and dGTP). In embodiments, the sequencing readout (i.e., detection) is accomplished by epifluorescence imaging. A variety of sequencing chemistries are available, non-limiting examples of which are described herein.

In embodiments, sequencing is performed according to a "sequencing-by-binding" method (see, e.g., U.S. Pat. Pubs. US2017/0022553 and US2019/0048404, each of which is incorporated herein by reference in its entirety), which refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide. As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

In embodiments, sequencing includes a plurality of sequencing cycles. In embodiments, sequencing includes 10 to 100 sequencing cycles. In embodiments, sequencing includes 50 to 100 sequencing cycles. In embodiments, sequencing includes 50 to 300 sequencing cycles. In embodiments, sequencing includes 50 to 150 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue. In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample, and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." Nature methods 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, or multi-photon microscopy.

In embodiments, sequencing includes extending a sequencing primer to incorporate a nucleotide containing a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product of a target nucleic acid). In embodiments, the sequencing includes sequencing-by-synthesis, sequencing by ligation, or pyrosequencing, and generates a sequencing read. In embodiments, the sequencing includes sequencing-by-binding and generates one or more sequencing reads. In embodiments, sequencing includes monitoring the sequential incorporation of complementary nucleotides. In embodiments, sequencing includes incorporating one or more modified nucleotides into the sequencing primer with a polymerase to create an extension strand, and detecting the one or more incorporated nucleotides so as to identify each incorporated nucleotide in the extension strand, thereby generating one or more sequencing reads.

In some embodiments, the method includes about 5 to about 200 sequencing cycles (e.g., about 5 to about 200 sequencing cycles per sequencing primer). In some embodiments, the method includes about 8 to about 200 sequencing cycles. In some embodiments, the method includes about 10 to about 200 sequencing cycles. In some embodiments, the method includes about 15 to about 200 sequencing cycles. In some embodiments, the method includes about 20 to about 200 sequencing cycles. In some embodiments, the method includes about 30 to about 200 sequencing cycles. In some embodiments, the method includes about 4 0 to about 200 sequencing cycles. In some embodiments, the method includes about 50 to about 200 sequencing cycles. In embodiments, the method includes about 5 sequencing cycles. In embodiments, the method includes about 8 sequencing cycles. In embodiments, the method includes about 10 sequencing cycles. In embodiments, the method includes about 15 sequencing cycles. In embodiments, the method includes about 20 sequencing cycles. In embodiments, the method includes about 30 sequencing cycles. In embodiments, the method includes about 40 sequencing cycles. In embodiments, the method includes about 50 sequencing cycles. In embodiments, the method includes about 75 sequencing cycles. In embodiments, the method includes about 100 sequencing cycles. In embodiments, the method includes about 125 sequencing cycles. In embodiments, the method includes about 150 sequencing cycles. In embodiments, the method includes about 175 sequencing cycles. In embodiments, the method includes about 200 sequencing cycles. In some embodiments, the method includes about 5 to about 200 sequencing cycles per sequencing primer. Thus, depending on the number of sequencing primers used, multiple sets of sequencing cycles may be employed (e.g., a first set of 200 cycles, a second set of 200 cycles, a third set of 200 cycles) resulting in a cumulative total of sequencing cycles that is the sum of each set of sequencing cycles.

In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated.

In embodiments, the method includes sequencing the first and/or the second strand of a amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738, 072, 7,541,444 and 7,057,026. Once such a modified nucleotide has been incorporated into the growing polynucleotide chain complementary to the region of the template being sequenced, there is no free 3'—OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360; 5,188,934; (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. In embodiments, sequencing includes detecting a sequence of signals and generating one or more sequencing reads. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by Nnucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US Patent Publication 2018/0274024, WO 2017/205336, US Patent Publication 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, the method further includes quantifying the biomolecule (e.g., target nucleic acid molecule or amplicons). Methods for quantifying a target polynucleotide or amplicon are well known to one skilled in the art. For example, during amplification of the target nucleic acid, quantitative techniques such as real-time polymerase chain reaction (RT-PCR) can be used to quantify the copy number of target nucleic acid molecules present in the clonal object as discussed in Logan et al. Real-Time PCR: Current Technology and Applications, Caister Academic Press. (2009). RT-PCR follows the general principle of polymerase chain reaction, however inclusion of detection molecules, such as non-specific fluorescent dyes that intercalate with any double-stranded DNA, or sequence-specific DNA probes consisting of oligonucleotides that are labeled with a fluorescent reporter, which permits detection only after hybridization of the probe with its complementary DNA target, allows for the detection of nucleic acid formed during amplification. The rate of detectable molecules is proportional to the copy number of target nucleic acid molecules present in the clonal object. Furthermore, quantifying the target nucleic acid molecule or amplicons can be done following amplification using standard gel electrophoresis and/or Southern blot techniques, which are well known in the art.

In embodiments, the polymer shell includes a plurality of first bioconjugate reactive moieties. In embodiments, the polymeric bioconjugate linker is formed through a reaction between a polymer shell (e.g., a polymer covalently attached to the surface of the particle) including a first bioconjugate reactive moiety and an oligonucleotide including a second bioconjugate reactive moiety. For example, the oligonucleotide is attached to the particle shell polymer, following degradation of the degradable particle core, via reaction between a particle polymer (e.g., a polymer covalently attached to the surface of the particle) including a first bioconjugate reactive moiety (e.g., an azide) and an oligonucleotide including a second bioconjugate reactive moiety (e.g., DBCO). In some embodiments, the particle is a functionalized particle including a degradable particle core and a particle shell, wherein said particle shell includes a plurality of bioconjugate reactive moieties, a plurality of oligonucleotide moieties, or a combination thereof, wherein each of the bioconjugate reactive moieties and each of the oligonucleotide moieties includes a linker binding the bioconjugate reactive moieties and oligonucleotide to the particle core.

In some embodiments, each of the plurality of bioconjugate reactive moieties include an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In some embodiments, each of the plurality of bioconjugate reactive moieties include an amine moiety, azide moiety, dibenzocyclooctyne (DBCO) moiety, epoxy moiety, or isocyanate moiety. In embodiments, each of the plurality of bioconjugate reactive moieties include an amine moiety, azide moiety, alkyne moiety, dibenzocyclooctyne (DBCO) moiety, epoxy moiety, or isocyanate moiety. In embodiments, the bioconjugate reactive moiety is an azido moiety. In embodiments, the first bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the second bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the first and the second bioconjugate reactive moieties are different. In embodiments, the first and the second bioconjugate reactive moieties are reactive with each other (e.g., an azide moiety and an DBCO moiety) to form a bioconjugate linker.

In embodiments, the first bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the first bioconjugate reactive moiety is an amine moiety, azide moiety, alkyne moiety, dibenzocyclooctyne (DBCO) moiety, epoxy moiety, or isocyanate moiety.

In embodiments, the second bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the second bioconjugate reactive moiety is an amine moiety, azide moiety, alkyne moiety, dibenzocyclooctyne (DBCO) moiety, epoxy moiety, or isocyanate moiety.

In embodiments, the first bioconjugate reactive moiety is an amine moiety, azide moiety, alkyne moiety, dibenzocyclooctyne (DBCO) moiety, epoxy moiety, or isocyanate moiety; and the second bioconjugate reactive moiety is an amine moiety, azide moiety, alkyne moiety, dibenzocyclooctyne (DBCO) moiety, epoxy moiety, or isocyanate moiety, wherein the second bioconjugate reactive moiety is different than the first bioconjugate reactive moiety.

In embodiments, the polymer shell includes a plurality of polymerized units of shell monomers. In embodiments, the polymer shell includes a copolymer of two or more of the following polymerizable monomers, wherein at least one of the polymerizable monomers includes a bioconjugate reactive moiety: polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), and/or isocyanatoethyl methacrylate (IEM).

In embodiments, the oligonucleotide moiety (alternatively referred to herein as primer or polynucleotide primer) is covalently attached to the polymer. In embodiments, the 5' end of the oligonucleotide moiety contains a functional group that is tethered to the polymer (i.e., the particle shell polymer or the polymeric particle). Non-limiting examples of covalent attachment include amine-modified oligonucleotide moieties reacting with epoxy or isothiocyanate groups on the polymer, succinylated oligonucleotide moieties reacting with aminophenyl or aminopropyl functional groups on the polymer, dibenzocyclocctyne-modified oligonucleotide moieties reacting with azide functional groups on the particle polymer (or vice versa), trans-cyclooctyne-modified oligonucleotide moieties reacting with tetrazine or methyl tetrazine groups on the polymer (or vice versa), disulfide modified oligonucleotide moieties reacting with mercaptofunctional groups on the polymer, amine-functionalized oligonucleotide moieties reacting with carboxylic acid groups on the polymer via 1-ethyl-3-(3-dimethylaminopropyl)-carbodiimide hydrochloride (EDC) chemistry, thiol-modified oligonucleotide moieties attaching to a polymer via a disulfide bond or maleimide linkage, alkyne-modified oligonucleotide moieties attaching to a polymer via copper-catalyzed click reactions to azide functional groups on the polymer, and acrydite-modified oligonucleotide moieties polymerizing with free acrylic acid monomers on the polymer to form polyacrylamide or reacting with thiol groups on the polymer.

In embodiments, the average longest dimension of the particle is about 100 nm to about 3000 nm. In embodiments, the average longest dimension of the particle is from about 150 nm to about 600 nm. In embodiments, the average longest dimension of the particle is from about 350 nm to about 600 nm. In embodiments, the average longest dimension of the particle is from about 400 nm to about 500 nm. In embodiments, the average longest dimension of the particle is about 450 nm. In embodiments, the average longest dimension of the particle is from about 150 nm to about 1,000 nm.

In embodiments, the average longest dimension of the degradable particle core is about 100 nm to about 3000 nm. In embodiments, the average longest dimension of the degradable particle core is from about 150 nm to about 600 nm. In embodiments, the average longest dimension of the degradable particle core is from about 350 nm to about 600 nm. In embodiments, the average longest dimension of the degradable particle core is from about 400 nm to about 500 nm. In embodiments, the average longest dimension of the degradable particle core is about 450 nm.

In embodiments, the average longest dimension of the nanoparticle is from about 100 nm to about 400 nm. In embodiments, the average longest dimension of the nanoparticle is about 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 225 nm, 230 nm, 235 nm, 240 nm, 245 nm, 250 nm, 255 nm, 260 nm, 265 nm, 270 nm, 275 nm, 280 nm, 285 nm, 290 nm, 295 nm, 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average longest dimension of the nanoparticle is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm. In embodiments, the average longest dimension of the nanoparticle is less than about 1000 nm. In embodiments, the average longest dimension of the nanoparticle is less than about 900 nm. In embodiments, the average longest dimension of the nanoparticle is less than about 800 nm. In embodiments, the average longest dimension of the nanoparticle is less than about 700 nm. In embodiments, the average longest dimension of the nanoparticle is less than about 600 nm. In embodiments, the average longest dimension of the nanoparticle is less than about 500 nm. In embodiments, the average longest dimension of the nanoparticle is less than about 400 nm. In embodiments, the average longest dimension of the nanoparticle is less than about 300 nm. In embodiments, the average longest dimension of the nanoparticle is less than about 200 nm. In embodiments, the average longest dimension of the nanoparticle is less than about 100 nm. In embodiments, the average longest dimension of the nanoparticle is 400 nm without the particle shell. In embodiments, the average longest dimension of the nanoparticle is about 550 to about 650 nm with the particle shell. In embodiments, the average longest dimension of the nanoparticle is about 580 to about 650 nm with the particle shell containing immobilized oligonucleotides.

In some embodiments, the average longest dimension of the particle is from about 200 nm to about 1000 nm. In embodiments, the average longest dimension of the particle is from about 150 nm to about 600 nm. In some embodiments, the average longest dimension of the particle is from about 350 nm to about 600 nm. In some embodiments, the average longest dimension of the particle is from about 400 nm to about 500 nm. In some embodiments, the average longest dimension of the particle is about 500 nm. In some embodiments, the average longest dimension of the particle is about 400 nm. In some embodiments, the average longest dimension of the particle is about 400 nm, 450 nm, 500 nm, or 550 nm. In some embodiments, the average longest dimension of the particle is about 410 nm, 420 nm, 430 nm, 440 nm or 450 nm. In some embodiments, the average longest dimension of the particle is about 460 nm, 470 nm, 480 nm, 490 nm or 500 nm. In embodiments, the average longest dimension of the particle is at least, about, or at most 100, 200, 300, 400, 500, 600, 700, 800, 900, 1000 nm, or a number or a range between any two of these values. In embodiments, the shell diameter is about 0.1-10 microns, 0.25-5 microns, 0.5-2 microns, 1 micron, or a number or a range between any two of these values. In embodiments, the particle shell diameter is at least, about, or at most 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 µm or a number or a range between any two of these values. In embodiments, the core diameter is about 150-700 nanometers, and/or the shell diameter (alternatively referred to as the particle polymer) is about 0.25-5 µm (microns).

In embodiments, the solid support includes a plurality of wells in a surface. For example, the solid support may be a planar support (e.g., a glass slide) including an arranged pattern of depressions etched directly into the support (e.g., FIGS. 2A-2C). Alternatively, the solid support may include a planar support including a polymer or resist attached to the support, wherein the polymer or resist includes an arrangement of depressions (i.e., wells) etched directly into the polymer or resist (e.g., FIG. 2D). For example, in embodiments both the surface of the interior of the wells (e.g., the bottom and axial walls of the well) and the surface of the planar support include the resist.

In embodiments, the solid support includes about $1 \times 10^5$ to about $5 \times 10^{10}$ wells. In embodiments, density of wells on the solid support may be tuned. For example, in embodiments, the multiwell container includes a density of at least about 100 wells per $mm^2$, about 1,000 wells per $mm^2$, about 0.1 million wells per $mm^2$, about 1 million wells per $mm^2$, about 2 million wells per mm$^2$, about 5 million wells per mm$^2$, about 10 million wells per mm$^2$, about 50 million wells per mm$^2$, or more. In embodiments, the multiwell container includes no more than about 50 million wells per mm$^2$, about 10 million wells per mm$^2$, about 5 million wells per mm$^2$, about 2 million wells per mm$^2$, about 1 million wells per mm$^2$, about 0.1 million wells per mm$^2$, about 1,000 wells per mm$^2$, about 100 wells per mm$^2$, or less. In embodiments, the solid support includes about 500, 1,000, 2,500, 5,000, or about 25,000 wells per mm$^2$. In embodiments, the solid support includes about $1\times10^6$ to about $1\times10^{12}$ wells. In embodiments, the solid support includes about $1\times10^7$ to about $1\times10^{12}$ wells. In embodiments, the solid support includes about $1\times10^8$ to about $1\times10^{12}$ wells. In embodiments, the solid support includes about $1\times10^6$ to about $1\times10^9$ wells. In embodiments, the solid support includes about $1\times10^9$ to about $1\times10^{10}$ wells. In embodiments, the solid support includes about $1\times10^7$ to about $1\times10^9$ wells. In embodiments, the solid support includes about $1\times10^8$ to about $1\times10^8$ wells. In embodiments, the solid support includes about $1\times10^6$ to about $1\times10^8$ wells. In embodiments, the solid support includes about $1\times10^6$, $1\times10^7$, $1\times10^8$, $1\times10^9$, $1\times10^{10}$, $1\times10^{11}$, $1\times10^{12}$, $5\times10^{12}$, or more wells. In embodiments, the solid support includes about $1.8\times10^9$, $3.7\times10^9$, $9.4\times10^9$, $1.9\times10^{10}$, or about $9.4\times10^{10}$ wells. In embodiments, the solid support includes about $1\times10^6$ or more wells. In embodiments, the solid support includes about $1\times10^7$ or more wells. In embodiments, the solid support includes about $1\times10^8$ or more wells. In embodiments, the solid support includes about $1\times10^9$ or more wells. In embodiments, the solid support includes about $1\times10^{10}$ or more wells. In embodiments, the solid support includes about $1\times10^{11}$ or more wells. In embodiments, the solid support includes about $1\times10^{12}$ or more wells. In embodiments, the solid support is a glass slide. In embodiments, the solid support is about 75 mm by about 25 mm. In embodiments, the solid support includes one, two, three, or four channels. In embodiments, the interstitial regions are substantially free of polymer shell, following degradation of the particles.

In embodiments, the plurality of oligonucleotides is present at a density of about 100 oligonucleotides per μm$^2$ to about 1,000,000 oligonucleotides per μm$^2$. In embodiments, the plurality of oligonucleotides is present at a density of about 100 oligonucleotides per μm$^2$ to about 1,000 oligonucleotides per μm$^2$. In embodiments, the plurality of oligonucleotides is present at a density of about 100 oligonucleotides per μm$^2$ to about 10,000 oligonucleotides per μm$^2$. In embodiments, the plurality of oligonucleotides is present at a density of about 100 oligonucleotides per μm$^2$ to about 100,000 oligonucleotides per μm$^2$. In embodiments, the plurality of oligonucleotides is present at a density of about 100 oligonucleotides per μm$^2$ to about 500,000 oligonucleotides per μm$^2$. In embodiments, the plurality of oligonucleotides is present at a density of about 100, 1,000, 10,000, 50,000, 100,000, 250,000, 500,000, 750,000, or 1,000,000 oligonucleotides per μm$^2$.

In embodiments, the arrays include about 10,000,000 wells/cm$^2$ to about 5,000,000,000 wells/cm$^2$. In embodiments, the arrays include about 100,000,000 wells/cm$^2$ to about 1,000,000,000 wells/cm$^2$. In embodiments, the arrays include about 100,000 wells/cm$^2$ to about 100,000,000 wells/cm$^2$. In embodiments, the arrays include about or about 10,000,000 wells/cm$^2$ to about 50,000,000 wells/cm$^2$.

In embodiments, the wells have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 μm, or a number or a range between any two of these values. In embodiments, the mean or median separation is about or at least about 0.1 μm. In embodiments, the mean or median separation is about or at least about 0.2 μm. In embodiments, the mean or median separation is about or at least about 0.3 μm. In embodiments, the mean or median separation is about or at least about 0.4 μm. In embodiments, the mean or median separation is about or at least about 0.5 μm. In embodiments, the mean or median separation is about or at least about 0.6 μm. In embodiments, the mean or median separation is about or at least about 0.7 μm. In embodiments, the mean or median separation is about or at least about 0.8 μm. In embodiments, the mean or median separation is about or at least about 0.9 μm. In embodiments, the mean or median separation is about or at least about 1.0 μm. In embodiments, the mean or median separation is about or at least about 1.1 μm. In embodiments, the mean or median separation is about or at least about 1.2 μm. In embodiments, the mean or median separation is about or at least about 1.3 μm. In embodiments, the mean or median separation is about or at least about 1.4 μm. In embodiments, the mean or median separation is about or at least about 1.5 μm. In embodiments, the mean or median separation is about or at least about 1.6 μm. In embodiments, the mean or median separation is about or at least about 1.7 μm. In embodiments, the mean or median separation is about or at least about 1.8 μm. In embodiments, the mean or median separation is about or at least about 1.9 μm. In embodiments, the mean or median separation is about or at least about 2.0 μm. In embodiments, the mean or median separation is about or at least about 2.1 μm. In embodiments, the mean or median separation is about or at least about 2.2 μm. In embodiments, the mean or median separation is about or at least about 2.3 μm. In embodiments, the mean or median separation is about or at least about 2.4 μm. In embodiments, the mean or median separation is about or at least about 2.5 μm. In embodiments, the mean or median separation is about or at least about 2.6 μm. In embodiments, the mean or median separation is about or at least about 2.7 μm. In embodiments, the mean or median separation is about or at least about 2.8 μm. In embodiments, the mean or median separation is about or at least about 2.9 μm. In embodiments, the mean or median separation is about or at least about 3.0 μm. In embodiments, the mean or median separation is about or at least about 3.1 μm. In embodiments, the mean or median separation is about or at least about 3.2 μm. In embodiments, the mean or median separation is about or at least about 3.3 μm. In embodiments, the mean or median separation is about or at least about 3.4 μm. In embodiments, the mean or median separation is about or at least about 3.5 μm. In embodiments, the mean or median separation is about or at least about 3.6 μm. In embodiments, the mean or median separation is about or at least about 3.7 μm. In embodiments, the mean or median separation is about or at least about 3.8 μm. In embodiments, the mean or median separation is about or at least about 3.9 μm. In embodiments, the mean or median separation is about or at least about 4.0 μm. In embodiments, the mean or median separation is about or at least about 4.1 μm. In embodiments, the mean or median separation is about or at least about 4.2 μm. In embodiments, the mean or median separation is about or at least about 4.3 µm. In embodiments, the mean or median separation is about or at least about 4.4 µm. In embodiments, the mean or median separation is about or at least about 4.5 µm. In embodiments, the mean or median separation is about or at least about 4.6 µm. In embodiments, the mean or median separation is about or at least about 4.7 µm. In embodiments, the mean or median separation is about or at least about 4.8 µm. In embodiments, the mean or median separation is about or at least about 4.9 µm. In embodiments, the mean or median separation is about or at least about 5.0 µm. The mean or median separation may be measured center-to-center (i.e., the center of one well to the center of a second well). In embodiments of the methods provided herein, the wells have a mean or median separation (measured center-to-center) from one another of about 0.5-5 µm. The mean or median separation may be measured edge-to-edge (i.e., the edge of well to the edge of a second well). In embodiments, the wells have a mean or median separation (measured edge-to-edge) from one another of about 0.2-1.5 µm. In embodiments, the wells have a mean or median separation (measured center-to-center) from one another of about 0.7-1.5 µm.

Neighboring features of an array can be discrete one from the other in that they do not overlap. Accordingly, the features can be adjacent to each other or separated by a gap (e.g., an interstitial space). In embodiments where features are spaced apart, neighboring sites can be separated, for example, by a distance of less than 10 µm, 5 µm, 1 µm, 0.9 µm, 0.8 µm, 0.7 µm, 0.6 µm, 0.5 µm, or less. The layout of features on an array can also be understood in terms of center-to-center distances between neighboring features. An array useful in the invention can have neighboring features with center-to-center spacing of less than about 10 µm, 5 µm, 1 µm, 0.9 µm, 0.8 µm, 0.7 µm, 0.6 µm, 0.5 µm, 0.4 µm, or less. In embodiments, the array has neighboring features with center-to-center spacing of less than about 10 µm. In embodiments, the array has neighboring features with center-to-center spacing of less than about 5 µm. In embodiments, the array has neighboring features with center-to-center spacing of less than about 1 µm. In embodiments, the array has neighboring features with center-to-center spacing of less than about 0.9 µm. In embodiments, the array has neighboring features with center-to-center spacing of less than about 0.8 µm. In embodiments, the array has neighboring features with center-to-center spacing of less than about 0.7 µm. In embodiments, the array has neighboring features with center-to-center spacing of less than about 0.6 µm. In embodiments, the array has neighboring features with center-to-center spacing of less than about 0.5 µm. In embodiments, the array has neighboring features with center-to-center spacing of less than about 0.4 µm. Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

In embodiments, the wells are separated from each other by about 0.5 µm to about 2.0 µm. In embodiments, the wells are separated from each other by about 0.7 µm to about 1.5 µm. In embodiments, the wells are about 0.2 µm to about 2 µm in diameter, and wherein the wells are about 0.5 µm to about 2 µm in depth. In some embodiments, the wells of the array are separated from each other by about 0.2 µm to about 2.0 µm. In some embodiments, the wells of the array are separated from each other by about 0.7 µm to about 1.5 µm.

In some embodiments, the wells of the array are separated from each other by at least or at most 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm. In some embodiments, the wells of the array are from about 0.2 µm to about 2 µm in diameter, and wherein the wells of the array are about 0.5 µm to about 2 µm in depth. In some embodiments, the wells of the array are from about 0.2 µm to about 2 µm in diameter, and wherein the wells of the array are about 0.5 µm to about 1.5 µm in depth. Each well of the multiwell container is capable of retaining a volume of liquid. For example, the volume of the wells can be at least about $1 \times 10^{-3}$ µm$^3$, about $1 \times 10^{-2}$ µm$^3$, about 0.1 µm$^3$, about 1 µm$^3$, about 10 µm$^3$, about 100 µm$^3$, or more. In embodiments, the volume of the wells can be at most about $1 \times 10^4$ µm$^3$, about $1 \times 10^3$ µm$^3$, about 100 µm$^3$, about 10 µm$^3$, about 1 µm$^3$, about 0.1 µm$^3$, or less. In embodiments, the depth of the well is measured from the bottom of the well to the top of the array. In embodiments, the depth of the well is measured from the bottom of the well to the top of the interstitial region. In embodiments, the depth of the well is measured from the bottom of the well to the top of the photoresist. In embodiments, the array is a nanoarray which can have nanowells having a diameter sufficient to allow only one particle into the well. It is understood that the size of the nanowell will be dependent upon the size of the particle. In some embodiments, the diameter of the nanowells are less than 700 nm, less than 600 nm, less than 500 nm, less than 400 nm, less than 300 nm, less than 200 nm, or less than 100 nm. It is also understood that the size of the wells on the array can be of various sizes and will ultimately depend on the systems and/or apparatus used to analyze later reactions.

In embodiments, the solid support includes a plurality of wells (e.g., a billion or more wells). In embodiments, the wells (e.g., each well) is separated from each other by about 0.2 µm to about 2.0 µm. In embodiments, the wells (e.g., each well) is separated from each other by about 0.3 µm to about 2.0 µm. In embodiments, the wells (e.g., each well) is separated from each other by about 0.4 µm to about 2.0 µm. In embodiments, the wells (e.g., each well) is separated from each other by about 0.5 µm to about 2.0 µm. In embodiments, the wells (e.g., each well) is separated from each other by about 1.0 µm to about 2.0 µm. In embodiments, the wells (e.g., each well) is separated from each other by about 1.0 µm to about 1.5 µm. In embodiments, the wells of the solid support are all the same size. In embodiments, the solid support includes wells that are from about 0.1 µm to about 3 µm in diameter. In embodiments, the solid support includes wells that are from about 0.2 µm to about 3 µm in diameter. In embodiments, the solid support includes wells that are from about 0.3 µm to about 3 µm in diameter. In embodiments, the solid support includes wells that are from about 0.4 µm to about 3 µm in diameter. In embodiments, the solid support includes wells that are from about 0.5 µm to about 3 µm in diameter. In embodiments, the solid support includes wells that are from about 0.6 µm to about 3 m in diameter. In embodiments, the solid support includes wells that are from about 0.7 µm to about 3 µm in diameter. In embodiments, the solid support includes wells that are from about 0.8 m to about 3 µm in diameter. In embodiments, the solid support includes wells that are from about 0.9 µm to about 3 µm in diameter. In embodiments, the solid support includes wells that are from about 1.0 µm to about 3 µm in diameter. In embodiments, the solid support includes wells that are from about 0.1 µm to about 2 µm in diameter. In embodiments, the solid support includes wells that are from about 0.2 µm to about 2 µm in diameter. In embodiments, the solid support includes wells that are from about 0.3 µm to about 2 µm in diameter. In embodiments, the solid support includes wells that are from about 0.4 µm to about 2 µm in diameter. In embodiments, the solid support includes wells that are from about 0.5 µm to about 2 µm in diameter. In embodiments, the solid support includes wells that are from about 0.6 µm to about 2 m in diameter. In embodiments, the solid support includes wells that are from about 0.7 µm to about 2 µm in diameter. In embodiments, the solid support includes wells that are from about 0.8 m to about 2 µm in diameter. In embodiments, the solid support includes wells that are from about 0.9 µm to about 2 µm in diameter. In embodiments, the solid support includes wells that are from about 1.0 µm to about 2 µm in diameter. In embodiments, the solid support includes wells that are from about 1.0 µm to about 1.5 µm in diameter. In embodiments, the solid support includes wells that are about 0.1 µm to about 2 µm in depth. In embodiments, the solid support includes wells that are about 0.2 µm to about 2 µm in depth. In embodiments, the solid support includes wells that are about 0.3 µm to about 2 µm in depth. In embodiments, the solid support includes wells that are about 0.4 µm to about 2 µm in depth. In embodiments, the solid support includes wells that are about 0.5 µm to about 2 µm in depth. In embodiments, the solid support includes wells that are about 0.6 µm to about 2 µm in depth. In embodiments, the solid support includes wells that are about 0.7 µm to about 2 µm in depth. In embodiments, the solid support includes wells that are about 0.8 µm to about 2 µm in depth. In embodiments, the solid support includes wells that are about 0.9 µm to about 2 µm in depth. In embodiments, the solid support includes wells that are about 1.0 µm to about 2 µm in depth. In embodiments, the solid support includes wells that are about 0.1 µm to about 1.5 µm in depth. In embodiments, the solid support includes wells that are about 0.2 µm to about 1.5 µm in depth. In embodiments, the solid support includes wells that are about 0.3 µm to about 1.5 µm in depth. In embodiments, the solid support includes wells that are about 0.4 µm to about 1.5 µm in depth. In embodiments, the solid support includes wells that are about 0.5 µm to about 1.5 µm in depth. In embodiments, the solid support includes wells that are about 0.6 µm to about 1.5 µm in depth. In embodiments, the solid support includes wells that are about 0.7 µm to about 1.5 µm in depth. In embodiments, the solid support includes wells that are about 0.8 µm to about 1.5 µm in depth. In embodiments, the solid support includes wells that are about 0.9 µm to about 1.5 µm in depth. In embodiments, the solid support includes wells that are about 1.0 µm to about 1.5 µm in depth. In embodiments, one or more wells are different sizes (e.g., one population of wells are 1.0 µm in diameter, and a second population are 0.5 µm in diameter). In embodiments, the solid support is a glass slide about 75 mm by about 25 mm. In embodiments, the solid support includes a resist (e.g., a photoresist or nanoimprint resist including a cross-linked polymer matrix attached to the solid support).

In embodiments, each well includes a plurality of nanowells. In embodiments, each nanowell is about 0.1 µm to about 2.0 µm in depth, and wherein the nanowells are about 0.1 µm to about 2.0 µm in diameter. In embodiments, each nanowell is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm in depth. In embodiments, each nanowell is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 µm in diameter.

In embodiments, the solid support includes a polymer layer. In embodiments the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

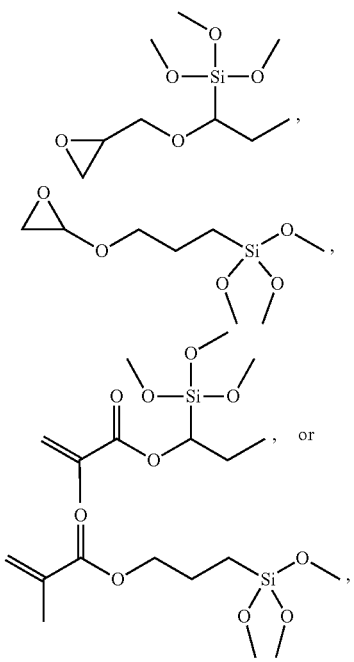

or a copolymer thereof.

In embodiments, the solid support includes a photoresist, alternatively referred to herein as a resist. A "resist" as used herein is used in accordance with its ordinary meaning in the art of lilthography and refers to a polymer matrix (e.g., a polymer network). In embodiments, the photoresist is a silsesquioxane resist, an epoxy-based polymer resist, poly (vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist. In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, Al$_2$O$_3$, TiO$_2$ or Ta$_2$O$_5$). In embodiments, the photoresist includes metal atoms, such as Si, Zr, Mg, Al, Ti or Ta atoms. In embodiments, the solid support includes an organically modified ceramic polymer resist.

In embodiments, the solid support includes polymerized units of alkoxysilyl methacrylate, alkoxysilyl acrylate, alkoxysilyl methylacrylamide, alkoxysilyl acrylamide, or a copolymer thereof. In embodiments, the solid support includes a resist, wherein the resist is a silsesquioxane resist, an epoxy-based polymer resist, poly(vinylpyrrolidone-vinyl acrylic acid) copolymer resist, an Off-stoichiometry thiolenes (OSTE) resist, amorphous fluoropolymer resist, a crystalline fluoropolymer resist, polysiloxane resist, or a organically modified ceramic polymer resist.

In embodiments, the method further includes sequencing the amplification product(s). Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. In embodiments, sequencing the target polynucleotide, or a complement thereof, by hybridizing a sequencing primer to the target polynucleotide, or a complement thereof, and extending the sequencing primer with a polymerase to incorporate one or more nucleotides; and detecting the incorporated nucleotides. A variety of sequencing chemistries are available, non-limiting examples of which are described herein.

Figure 1B:
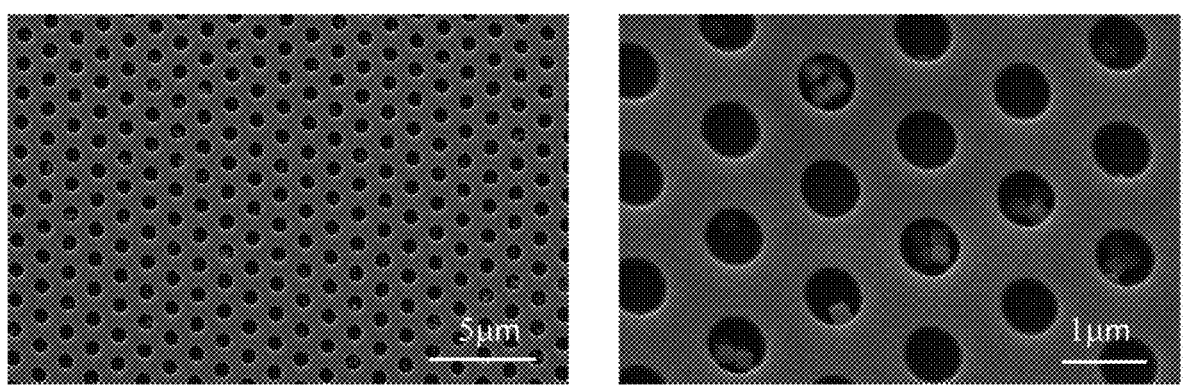
Figure 1B:
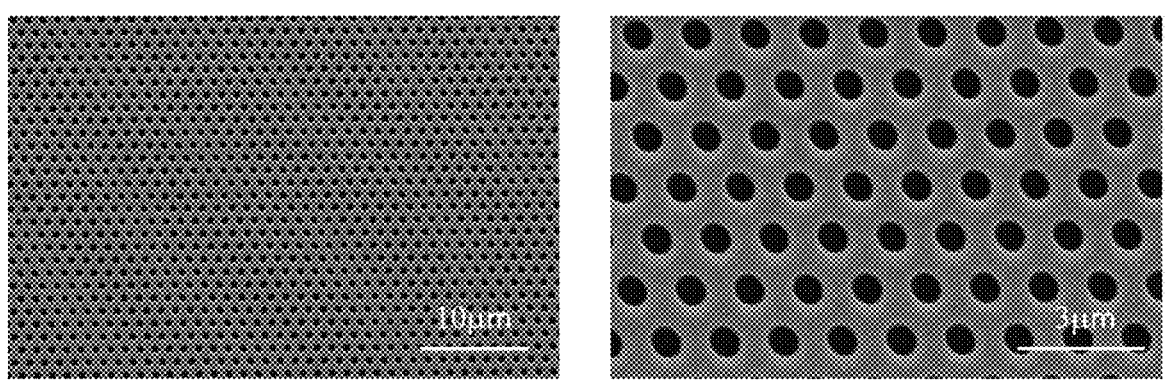

In an aspect is provided a method of attaching a polymer composition to a solid support, the method including contacting a solid support including two or more wells with the plurality of particles as described herein, including embodiments, thereby depositing the one or more particles in a well; contacting the one or more particles with a degrading agent thereby decomposing the degradable particle core and forming a polymer composition attached to the well, for example as shown in FIG. 1B and further illustrated in FIG. 7. In embodiments, the method further includes covalently linking an oligonucleotide moiety to polymer composition (e.g., the polymerized units of shell monomers) via a polymeric bioconjugate linker. In embodiments, the polymer composition includes a plurality of polymerized units of shell monomers wherein one or more shell monomers includes an oligonucleotide moiety covalently linked to the shell monomer. In embodiments, this method further includes hybridizing a biomolecule to the oligonucleotide and detecting the biomolecule, thereby detecting the oligonucleotide. In further embodiments, the oligonucleotide moiety is capable of hybridizing to a complementary sequence of a template nucleic acid. In embodiments, the particle can be affixed to the surface of a substrate (e.g., a flow cell or within a well) via chemical, physioadsorptive, or both forces. In embodiments, the polymer coated particles are affixed to the surface of the substrate by loading them into open wells on the surface of the substrate. In embodiments, the particles may be affixed to the surface of the substrate via centrifugation.

In an aspect is provided a method of forming a multilayer polymer composition, the method including: contacting a solid support with a first plurality of first particles to form a first layer of first particles, wherein each first particle includes a first degradable particle core and a first polymer shell attached to the particle core, wherein the first polymer shell includes a first bioconjugate reactive moiety; contacting the first layer of first particles with a first degrading agent and decomposing the first degradable particle core and forming a first polymer layer; contacting the solid support with a second plurality of second particles to form a second layer of second particles, wherein each second particle includes a second degradable particle core and a second polymer shell attached to the particle core, wherein the second polymer shell includes a second bioconjugate reactive moiety; and contacting the second with a second degrading agent and decomposing the second degradable particle core and forming a second polymer layer, thereby forming a multilayer polymer composition.

In embodiments, the method further includes binding a biomolecule to the first layer by contacting the first layer with a biomolecule including a third bioconjugate reactive moiety and forming a bioconjugate linker, thereby attaching the biomolecule to the first layer. In embodiments, the method further includes binding a biomolecule to the second layer by contacting the second layer with a biomolecule including a fourth bioconjugate reactive moiety and forming a bioconjugate linker, thereby attaching the biomolecule to the second layer.

In embodiments, the biomolecule is a probe. In embodiments, the probe is a labeled oligonucleotide. In embodiments, the probe is a complementary oligonucleotide moiety (i.e., complementary to the oligonucleotide covalently linked to the particle shell. In embodiments, the biomolecule is a protein or an oligonucleotide. In embodiments, the method includes hybridizing a labeled probe to the oligonucleotide and detecting the labeled probe, thereby detecting the oligonucleotide.

In embodiments, the method includes hybridizing a target polynucleotide to the oligonucleotide and extending with a polymerase the oligonucleotide to form a complement of the target polynucleotide. In embodiments, the method further includes amplifying the complement of the target polynucleotide. In embodiments, amplifying includes of rolling circle amplification (RCA), exponential rolling circle amplification (eRCA), recombinase polymerase amplification (RPA), helicase dependent amplification (HDA), or template walking amplification. In embodiments, amplifying includes thermal bridge polymerase chain reaction (t-bPCR) amplification, chemical bridge polymerase chain reaction (c-bPCR) amplification or chemical-thermal bridge polymerase chain reaction (cT-bPCR) amplification).

It will be appreciated that any of the amplification methodologies described herein or known in the art can be utilized with universal or target-specific primers to amplify the target polynucleotide. Suitable methods for amplification include, but are not limited to, the polymerase chain reaction (PCR), strand displacement amplification (SDA), transcription mediated amplification (TMA) and nucleic acid sequence-based amplification (NASBA), for example, as described in U.S. Pat. No. 8,003,354, which is incorporated herein by reference in its entirety. The above amplification methods can be employed to amplify one or more nucleic acids of interest. Additional examples of amplification processes include, but are not limited to, bridge-PCR, recombinase polymerase amplification (RPA), loop-mediated isothermal amplification (LAMP), rolling circle amplification (RCA), strand displacement amplification, RCA with exponential strand displacement amplification. In embodiments, amplification comprises an isothermal amplification reaction. In embodiments, amplification comprises bridge amplification. In general, bridge amplification uses repeated steps of annealing of primers to templates, primer extension, and separation of extended primers from templates. Because primers are attached within the core polymer, the extension products released upon separation from an initial template is also attached within the core. The 3' end of an amplification product is then permitted to anneal to a nearby reverse primer that is also attached within the core, forming a "bridge" structure. The reverse primer is then extended to produce a further template molecule that can form another bridge. In embodiments, forward and reverse primers hybridize to primer binding sites that are specific to a particular target nucleic acid. In embodiments, forward and reverse primers hybridize to primer binding sites that have been added to, and are common among, target polynucleotides. Adding a primer binding site to target nucleic acids can be accomplished by any suitable method, examples of which include the use of random primers having common 5' sequences and ligating adapter nucleotides that include the primer binding site. Examples of additional clonal amplification techniques include, but are not limited to, bridge PCR, solid-phase rolling circle amplification (RCA), solid-phase exponential rolling circle amplification, solid-phase recombinase polymerase amplification (RPA), solid-phase helicase dependent amplification (HDA), template walking amplification, emulsion PCR on particles (beads), or combinations of the aforementioned methods. Optionally, during clonal amplification, additional solution-phase primers can be supplemented in the flow cell for enabling or accelerating amplification.

In embodiments, amplifying includes contacting the plurality of particles with one or more reagents for amplifying the target polynucleotide. Examples of reagents include but are not limited to polymerase, buffer, and nucleotides (e.g., an amplification reaction mixture). In certain embodiments, the term "amplifying" refers to a method that includes a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In embodiments, amplifying generates an amplicon. In embodiments, an amplicon contains multiple, tandem copies of the circularized nucleic acid molecule of the corresponding sample nucleic acid. The number of copies can be varied by appropriate modification of the amplification reaction including, for example, varying the number of amplification cycles run, using polymerases of varying processivity in the amplification reaction and/or varying the length of time that the amplification reaction is run, as well as modification of other conditions known in the art to influence amplification yield. Generally, the number of copies of a nucleic acid in an amplicon is at least 100, 200, 500, 1000, 2000, 3000, 4000, 5000, 6000, 7000, 8000, 9000 and 10,000 copies, and can be varied depending on the application. As disclosed herein, one form of an amplicon is as a nucleic acid "ball" localized to the particle and/or well of the array. The number of copies of the nucleic acid can therefore provide a desired size of a nucleic acid "ball" or a sufficient number of copies for subsequent analysis of the amplicon, e.g., sequencing.

In embodiments of the methods provided herein, arraying the particles occurs prior to contacting the particles with a sample that includes a target polynucleotide. In other embodiments, arraying the particles occurs after contacting the particles with a sample that includes a target polynucleotide. In other embodiments, arraying the particles occurs after amplifying the target polynucleotide.

In embodiments, the first particle includes a plurality of first bioconjugate reactive moieties. In embodiments, the first polymer shell and/or the second polymer shell includes a plurality of polymerized units of shell monomers. In embodiments, the average longest dimension of the first particle and/or second particle is about 100 nm to about 3000 nm. In embodiments, the average longest dimension of the first degradable particle core and/or the second degradable core is about 100 nm to about 3000 nm. In embodiments, the average longest dimension of the first particle and/or second particle is from about 150 nm to about 600 nm. In embodiments, the average longest dimension of the first particle and/or second particle is from about 350 nm to about 600 nm. In embodiments, the average longest dimension of the first particle and/or second particle is from about 400 nm to about 500 nm. In embodiments, the average longest dimension of the first particle and/or second particle is about 450 nm.

In embodiments, the degradable particle core includes a metal-organic framework (MOF) core. In embodiments, the degradable particle core is a Isoreticular Metal-Organic Framework (IR-MOF) core, Zeolitic Imidazolate Framework (ZIF) core, Porous Coordination Network (PCN) core, Materials Institute Lavoisier (MIL) MOF core, Porous Coordination Polymer (PCP) core, or University of Oslo (UiO) MOF core. In embodiments, the MOF particle is a Zeolitic Imidazolate Framework 8 (ZIF-8) core or a UiO-66 MOF core. In embodiments, the degradable particle core does not dissolve in deionized water (e.g., water absent a degrading agent).

In embodiments, the degradable particle core is a polystyrene (PS) particle, or polymethyl methacrylate (PMMA) particle, or latex particle. In embodiments, the degradable particle core includes disulfide-polymers. Disulfide bonds may be incorporated into polymeric materials in a variety of ways, for example using disulfide containing cross-linkers, redox-responsive self-assembly of amphiphilic polymers, biodegradable polymers, and/or linear and dendritic disulfide-containing monomers. For example, 2,2'-(ethylenedioxy)diethanethiol (EDDET) monomers may be polymerized to form a degradable particle core. Additionally, acrydite moieties include thiol groups capable of forming a disulfide bond and may be polymerized. In embodiments, the degradable particle core includes a plurality of polymerized monomers (e.g., as described herein) and includes a reversible crosslinker. Reversible crosslinking may allow for the polymer to linearize or dissociate under appropriate conditions. In embodiments, the reversible crosslinker includes a thiol moiety or a disulfide (e.g., a cystamine or a modified cystamine). In embodiments, the degradable particle core includes one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. In embodiments, the degradable particle core includes poly(acrylamide-co-acrylic acid) crosslinked with disulfide linkages. The preparation of the degradable particle core includes a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). For thiol and disulfide containing degradable particle cores a suitable degrading agent may be a reducing agent (e.g., dithiothreitol (DTT) or tris(2-carboxyethyl)phosphine (TCEP)).

In embodiments, wherein the first polymer shell and/or the second polymer shell includes polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, wherein the first polymer shell and/or the second polymer shell includes polyacrylamide (AAm), glicydyl methacrylate (GMA), polyethylene glycol methacrylate (PEGMA), polyethylene glycol acrylate (PEGA), isocyanatoethyl methacrylate (IEM), or a copolymer thereof.

In embodiments, the first bioconjugate reactive moiety and/or the second bioconjugate reactive moiety is an amine moiety, aldehyde moiety, alkyne moiety, azide moiety, carboxylic acid moiety, dibenzocyclooctyne (DBCO) moiety, tetrazine moiety, epoxy moiety, isocyanate moiety, furan moiety, maleimide moiety, thiol moiety, or transcyclooctene (TCO) moiety. In embodiments, the first bioconjugate reactive moiety and/or the second bioconjugate reactive moiety is an amine moiety, azide moiety, alkyne moiety, dibenzocyclooctyne (DBCO) moiety, epoxy moiety, or isocyanate moiety.

In embodiments, the method includes sequencing the target polynucleotide, or a complement thereof, by hybridizing a sequencing primer to the target polynucleotide, or a complement thereof, and extending the sequencing primer to incorporate one or more nucleotides; and detecting the incorporated nucleotides.

In an aspect is provided a method of sequencing a target polynucleotide, the method including: (i) contacting a solid support including a plurality of particles (e.g., particles described herein) with a degrading agent and decomposing the particles thereby forming a polymer film (e.g., wherein the polymer film is substantially the same composition as the polymer shell) attached to solid support, wherein each particle includes a degradable particle core and a polymer shell attached to the particle core, wherein the polymer shell includes a first bioconjugate reactive moiety; (ii) contacting the polymer film with an oligonucleotide including a second bioconjugate reactive moiety and binding the oligonucleotide to the polymer film; (iii) hybridizing a target polynucleotide to the oligonucleotide and extending the oligonucleotide with a polymerase to form a complement of the target polynucleotide; and (iv) sequencing the complement of the target polynucleotide. In embodiments, the method includes amplifying the complement of the target polynucleotide (e.g., amplifying the complement of the target and/or the target polynucleotide using methods known in the art and described herein).

In another aspect is provided a method of sequencing a target polynucleotide, the method including: (i) contacting a solid support including a plurality of particles with a degrading agent and decomposing the particles thereby forming a polymer film attached to solid support, wherein each particle includes a degradable particle core and a polymer shell attached to the particle core, wherein the polymer shell includes an oligonucleotide moiety covalently attached to the polymer shell; (ii) hybridizing a target polynucleotide to the oligonucleotide moiety and extending the oligonucleotide with a polymerase to form a complement of the target polynucleotide; and (iii) sequencing the complement of the target polynucleotide.

In embodiments, the solid support includes a plurality of wells. In embodiments, the plurality of wells includes one or more particles. In embodiments, one or more particles are attached to a surface inside a well, and one or more particles are attached to a surface outside a well. In embodiments, the method includes removing the one or more particles attached to the surface outside a well prior to step (i). In embodiments, removing includes polishing the solid support with a cleaning article.

In embodiments, the solid support includes about $1\times10^5$ to about $5\times10^{10}$ wells. In embodiments, the wells are separated from each other by about 0.5 µm to about 2.0 µm. In embodiments, the wells are separated from each other by about 0.7 µm to about 1.5 µm. In embodiments, the wells are about 0.2 µm to about 2 µm in diameter, and wherein the wells are about 0.5 µm to about 2 µm in depth. In embodiments, the surface of the solid support and the surface of the interior of the well includes polymerized units of alkoxysilyl methacrylate, alkoxysilyl acrylate, alkoxysilyl methylacrylamide, alkoxysilyl acrylamide, or a copolymer thereof.

In embodiments, sequencing includes sequencing by synthesis, sequencing by binding, sequencing by ligation, or pyrosequencing. In embodiments, sequencing includes hybridizing a sequencing primer to the target polynucleotide, or a complement thereof, and incorporating one or more nucleotides into the sequencing primer with a polymerase to create an extension strand; and detecting the one or more incorporated nucleotides.

In embodiments, the polymer shell includes polyacrylamide (AAm), poly(N-(5-azidoacetamidylpentyl)acrylamide-co-acrylamide (PAZAM), poly-N-isopropylacrylamide, poly N-isopropylpolyacrylamide, polyethylene glycol acrylate, methacrylate, polyacrylic acid, poly(hydroxyethyl methacrylate) (PHEMA), poly(methyl methacrylate) (PNMIA), poly(N-isopropylacrylamide) (PNIPAAm), glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol metbacrylate (PEGMA), polyethylene glycol acrylate (PEGA), isocyanatoethyl methacrylate (IEM), or a copolymer thereof.

Different degrading agents may be used to dissolve, degrade, and/or break apart the degradable particle core. Different MOFs will preferentially digest under different conditions especially with regard to pH. For example, the ZIF-8 MOF is much more sensitive to acidic conditions than basic conditions. The ZIF-8 MOF will digest at around pH 3-5 in the acidic range but needs relatively harsh basic conditions to digest (pH of about 12-14). Other MOFs such as UiO-66 ($Zr^{4+}$ and terephthalic acid) for example will digest much more easily in basic conditions.

In embodiments, the degrading agent is a chelator. A chelator is a compound that binds to metal ions from solution. Examples of chelating agents include ethylenediaminetetraacetic acid (EDTA), citric acid, ethylene glycol-bis(3-aminoethyl ether)-N,N,N',N'-tetraacetic acid (EGTA), polyaminopolycarboxylic acid (PAP), 1,2-diaminocyclohexanetetraacetic acid (DCTA), nitrilotriacetic acid (NTA), dimercaptosuccinic acid (DMSA)1,2-bis(o-aminophenoxy)ethane-N,N,N',N'-tetraacetic acid (BAPTA), and polyphosphates. In embodiments, the chelator includes a nitrogen aromatic moiety.

In embodiments, the degrading agent is a 0.1 to 1.0 M solution of an acid or base. In embodiments, the degrading agent is a 0.1 to 0.5 M solution of an acid or base solution. In embodiments, the degrading agent is a 0.1 M solution of an acid or base solution. In embodiments, the degrading agent is a 0.2 M solution of an acid or base solution. In embodiments, the degrading agent is a 0.3 M solution of an acid or base solution. In embodiments, the degrading agent is a 0.4 M solution of an acid or base solution. In embodiments, the degrading agent is a 0.5 M solution of an acid or base solution. In embodiments, the degrading agent is a 0.6 M solution of an acid or base solution. In embodiments, the degrading agent is a 0.7 M solution of an acid or base solution. In embodiments, the degrading agent is a 0.8 M solution of an acid or base solution. In embodiments, the degrading agent is a 0.9 M solution of an acid or base solution. In embodiments, the degrading agent is a 1.0 M solution of an acid or base solution. In embodiments, the degrading agent is a 0.1 M solution of an acid solution. In embodiments, the degrading agent is a 0.1 M solution of HCl. In embodiments, the degrading agent is a 0.2 M solution of an acid solution. In embodiments, the degrading agent is a 0.2 M solution of HCl. In embodiments, the degrading agent is a 0.3 M solution of an acid solution. In embodiments, the degrading agent is a 0.3 M solution of HCl. In embodiments, the degrading agent is a 0.4 M solution of an acid solution. In embodiments, the degrading agent is a 0.4 M solution of HCl. In embodiments, the degrading agent is a 0.5 M solution of an acid solution. In embodiments, the degrading agent is a 0.5 M solution of HCl. In embodiments, the degrading agent is a 0.6 M solution of an acid solution. In embodiments, the degrading agent is a 0.6 M solution of HCl. In embodiments, the degrading agent is a 0.7 M solution of an acid solution. In embodiments, the degrading agent is a 0.7 M solution of HCl. In embodiments, the degrading agent is a 0.8 M solution of an acid solution. In embodiments, the degrading agent is a 0.8 M solution of HCl. In embodiments, the degrading agent is a 0.9 M solution of an acid solution. In embodiments, the degrading agent is a 0.9 M solution of HCl. In embodiments, the degrading agent is a 1.0 M solution of an acid solution. In embodiments, the degrading agent is a 1.0 M solution of HCl. In embodiments, the degrading agent is a 0.1 M solution of a base solution. In embodiments, the degrading agent is a 0.1 M solution of NaOH solution. In embodiments, the degrading agent is a 0.2 M solution of a base solution. In embodiments, the degrading agent is a 0.2 M solution of NaOH solution. In embodiments, the degrading agent is a 0.3 M solution of a base solution. In embodiments, the degrading agent is a 0.3 M solution of NaOH solution. In embodiments, the degrading agent is a 0.4 M solution of a base solution. In embodiments, the degrading agent is a 0.4 M solution of NaOH solution. In embodiments, the degrading agent is a 0.5 M solution of a base solution. In embodiments, the degrading agent is a 0.5 M solution of NaOH solution. In embodiments, the degrading agent is a 0.6 M solution of a base solution. In embodiments, the degrading agent is a 0.6 M solution of NaOH solution. In embodiments, the degrading agent is a 0.7 M solution of a base solution. In embodiments, the degrading agent is a 0.7 M solution of NaOH solution. In embodiments, the degrading agent is a 0.8 M solution of a base solution. In embodiments, the degrading agent is a 0.8 M solution of NaOH solution. In embodiments, the degrading agent is a 0.9 M solution of a base solution. In embodiments, the degrading agent is a 0.9 M solution of NaOH solution. In embodiments, the degrading agent is a 1.0 M solution of a base solution. In embodiments, the degrading agent is a 1.0 M solution of NaOH solution.

In embodiments, the degradable particle core is contacted with an acid or base solution to degrade the particle core. In embodiments, degrading the particle core causes the release of the polymer shell. In embodiments, the degradable particle core is contacted with an acid or base solution for about 10 sec to about 20 min. In embodiments, the degradable particle core is contacted with an acid or base solution for about 30 sec to about 15 min. In embodiments, the degradable particle core is contacted with an acid or base solution for about 1 min to about 10 min. In embodiments, the degradable particle core is contacted with an acid or base solution for about 2 min to about 8 min. In embodiments, the degradable particle core is contacted with an acid or base solution for about 1 min, 2 min, 3 min, 4 min, 5 min, 6 min, 7 min, 8 min, 9 min or 10 min. In embodiments, the degradable particle core is contacted with an acid or base solution for about 5 min, 6 min, 7 min, 8 min, 9 min or 10 min.

In embodiments, the degrading agent is a buffered solution including a pH of greater than 9.0. In embodiments, the degrading agent is a buffered solution including a pH of greater than 10.0. In embodiments, the degrading agent is a buffered solution including a pH of greater than 11.0. In embodiments, the degrading agent has a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In embodiments, the degrading agent includes NaOH.

In embodiments, the degrading agent includes a hydroxide ion (e.g., sodium hydroxide, potassium hydroxide, calcium hydroxide, magnesium hydroxide). In embodiments, the degrading agent is ammonia. In embodiments, the degrading agent is sodium bicarbonate. In embodiments, the degrading agent is potassium carbonate. In embodiments, the degrading agent is sodium carbonate. In embodiments, the degrading agent is potassium bicarbonate. In embodiments, the degrading agent is sodium citrate.

In embodiments, the mass of the particle core reduces upon incubation with a degrading agent. In embodiments, the shape of the particle core reduces upon incubation with a degrading agent. In embodiments, the degradable particle core is removed to release material (i.e., the particle polymer) through the presence of an external stimulus. For example, the degradable particle core may be removed or dissolved by contacting the particles with a degrading agent thereby decomposing the degradable particle core. In embodiments, the external stimulus is a change in pH. In embodiments, the pH is altered with a base to degrade the particle core. In embodiments, the base is NaOH. In embodiments, the pH is altered with an acid to degrade the particle core. In embodiments, the acid is HCl. In embodiments, the external stimulus is the presence of a compound such as phosphate. In embodiments, degrading the particle core causes the release of the polymer shell. In embodiments, the degradable particle core is degraded under conditions that would not degrade and/or alter an oligonucleotide. In embodiments, the mass of the degradable particle core reduces upon incubation and/or contact with the external stimulus. In embodiments, the degradable particle core is incubated in PBS (phosphate buffered saline) or an alkaline solution (e.g., NaOH). Pre-soaking the degradable particle core in an alkaline buffered solution greatly enhances the subsequent degradation upon basic or acidic digestion of the particle core.

In embodiments, the degradable particle core is contacted with a degrading agent comprising about 0.1 to 1.0 M of an acid (e.g., HCl) or a base (e.g., NaOH). In embodiments, the degradable particle core is contacted with about 0.1 to 0.5 M solution of an acid or base solution. In embodiments, the degradable particle core is contacted with about 0.1 M solution of an acid or base solution. In embodiments, the degradable particle core is contacted with about 0.2 M solution of an acid or base solution. In embodiments, the degradable particle core is contacted with about 0.3 M solution of an acid or base solution. In embodiments, the degradable particle core is contacted with about 0.4 M solution of an acid or base solution. In embodiments, the degradable particle core is contacted with about 0.5 M solution of an acid or base solution. In embodiments, the degradable particle core is contacted with about 0.6 M solution of an acid or base solution. In embodiments, the degradable particle core is contacted with about 0.7 M solution of an acid or base solution. In embodiments, the degradable particle core is contacted with about 0.8 M solution of an acid or base solution. In embodiments, the degradable particle core is contacted with about 0.9 M solution of an acid or base solution. In embodiments, the degradable particle core is contacted with about 1.0 M solution of an acid or base solution. In embodiments, the degradable particle core is contacted with about 0.1 M solution of an acid solution. In embodiments, the degradable particle core is contacted with about 0.1 M solution of HCl. In embodiments, the degradable particle core is contacted with about 0.2 M solution of an acid solution. In embodiments, the degradable particle core is contacted with about 0.2 M solution of HCl. In embodiments, the degradable particle core is contacted with about 0.3 M solution of an acid solution. In embodiments, the degradable particle core is contacted with about 0.3 M solution of HCl. In embodiments, the degradable particle core is contacted with about 0.4 M solution of an acid solution. In embodiments, the degradable particle core is contacted with about 0.4 M solution of HCl. In embodiments, the degradable particle core is contacted with about 0.5 M solution of an acid solution. In embodiments, the degradable particle core is contacted with about 0.5 M solution of HCl. In embodiments, the degradable particle core is contacted with about 0.6 M solution of an acid solution. In embodiments, the degradable particle core is contacted with about 0.6 M solution of HCl. In embodiments, the degradable particle core is contacted with about 0.7 M solution of an acid solution. In embodiments, the degradable particle core is contacted with about 0.7 M solution of HCl. In embodiments, the degradable particle core is contacted with about 0.8 M solution of an acid solution. In embodiments, the degradable particle core is contacted with about 0.8 M solution of HCl. In embodiments, the degradable particle core is contacted with about 0.9 M solution of an acid solution. In embodiments, the degradable particle core is contacted with about 0.9 M solution of HCl. In embodiments, the degradable particle core is contacted with about 1.0 M solution of an acid solution. In embodiments, the degradable particle core is contacted with about 1.0 M solution of HCl. In embodiments, the degradable particle core is contacted with about 0.1 M solution of a base solution. In embodiments, the degradable particle core is contacted with about 0.1 M solution of NaOH solution. In embodiments, the degradable particle core is contacted with about 0.2 M solution of a base solution. In embodiments, the degradable particle core is contacted with about 0.2 M solution of NaOH solution. In embodiments, the degradable particle core is contacted with about 0.3 M solution of a base solution. In embodiments, the degradable particle core is contacted with about 0.3 M solution of NaOH solution. In embodiments, the degradable particle core is contacted with about 0.4 M solution of a base solution. In embodiments, the degradable particle core is contacted with about 0.4 M solution of NaOH solution. In embodiments, the degradable particle core is contacted with about 0.5 M solution of a base solution. In embodiments, the degradable particle core is contacted with about 0.5 M solution of NaOH solution. In embodiments, the degradable particle core is contacted with about 0.6 M solution of a base solution. In embodiments, the degradable particle core is contacted with about 0.6 M solution of NaOH solution. In embodiments, the degradable particle core is contacted with about 0.7 M solution of a base solution. In embodiments, the degradable particle core is contacted with about 0.7 M solution of NaOH solution. In embodiments, the degradable particle core is contacted with about 0.8 M solution of a base solution. In embodiments, the degradable particle core is contacted with about 0.8 M solution of NaOH solution. In embodiments, the degradable particle core is contacted with about 0.9 M solution of a base solution. In embodiments, the degradable particle core is contacted with about 0.9 M solution of NaOH solution. In embodiments, the degradable particle core is contacted with about 1.0 M solution of a base solution. In embodiments, the degradable particle core is contacted with about 1.0 M solution of NaOH solution.

In embodiments, the degrading agent includes a pH of less than 7.0. In embodiments, the degrading agent includes a pH of 0.5. In embodiments, the degrading agent includes a pH of 0.6. In embodiments, the degrading agent includes a pH of 0.7. In embodiments, the degrading agent includes a pH of 0.8. In embodiments, the degrading agent includes a pH of 0.9. In embodiments, the degrading agent includes a pH of 1.0. In embodiments, the degrading agent includes a pH of 1.1. In embodiments, the degrading agent includes a pH of 1.2. In embodiments, the degrading agent includes a pH of 1.3. In embodiments, the degrading agent includes a pH of 1.4. In embodiments, the degrading agent includes a pH of 1.5. In embodiments, the degrading agent includes a pH of 1.6. In embodiments, the degrading agent includes a pH of 1.7. In embodiments, the degrading agent includes a pH of 1.8. In embodiments, the degrading agent includes a pH of 1.9. In embodiments, the degrading agent includes a pH of 2.0. In embodiments, the degrading agent includes a pH of 2.1. In embodiments, the degrading agent includes a pH of 2.2. In embodiments, the degrading agent includes a pH of 2.3. In embodiments, the degrading agent includes a pH of 2.4. In embodiments, the degrading agent includes a pH of 2.5. In embodiments, the degrading agent includes a pH between 0.5 and 2.0.

In embodiments, the degrading agent includes a pH of greater than 7.0. In embodiments, the degrading agent includes a pH of 12.5. In embodiments, the degrading agent includes a pH of 12.6. In embodiments, the degrading agent includes a pH of 12.7. In embodiments, the degrading agent includes a pH of 12.8. In embodiments, the degrading agent includes a pH of 12.9. In embodiments, the degrading agent includes a pH of 13.0. In embodiments, the degrading agent includes a pH of 13.1. In embodiments, the degrading agent includes a pH of 13.2. In embodiments, the degrading agent includes a pH of 13.3. In embodiments, the degrading agent includes a pH of 13.4. In embodiments, the degrading agent includes a pH of 13.5. In embodiments, the degrading agent includes a pH of 13.6. In embodiments, the degrading agent includes a pH of 13.7. In embodiments, the degrading agent includes a pH of 13.8. In embodiments, the degrading agent includes a pH of 13.9. In embodiments, the degrading agent includes a pH of 14.0. In embodiments, the degrading agent includes a pH between 12.0 and 14.0.

In embodiments, the degradable particle core is contacted with degrading agent including an acid or base solution to degrade the particle core. In embodiments, the degradable particle core is contacted with degrading agent including an acid or base solution to degrade the particle core prior to attaching the oligonucleotides. In embodiments, degrading the particle core causes the release of the polymer shell as shown in FIG. 7. In embodiments, the degradable particle core is contacted with a degrading agent (e.g., an acid or base solution) for about 10 sec to about 20 min. In embodiments, the degradable particle core is contacted with a degrading agent (e.g., an acid or base solution) for about 30 sec to about 15 min. In embodiments, the degradable particle core is contacted with a degrading agent (e.g., an acid or base solution) for about 1 min to about 10 min. In embodiments, the degradable particle core is contacted with a degrading agent (e.g., an acid or base solution) for about 2 min to about 8 min. In embodiments, the degradable particle core is contacted with a degrading agent (e.g., an acid or base solution) for about 1 min, 2 min, 3 min, 4 min, 5 min, 6 min, 7 min, 8 min, 9 min or 10 min. In embodiments, the degradable particle core is contacted with a degrading agent (e.g., an acid or base solution) for about 5 min, 6 min, 7 min, 8 min, 9 min or 10 min.

In embodiments, the method includes contacting the solid support as described herein with a polynucleotide including a primer binding sequence (e.g., a sequence complementary to an immobilized oligonucleotide); hybridizing the primer binding sequence to a first immobilized oligonucleotide of the second plurality of immobilized oligonucleotides; and extending the first immobilized oligonucleotide with a polymerase to form a first immobilized polynucleotide. In embodiments, the polynucleotide further includes a primer sequence, and the immobilized polynucleotide includes a complement of the primer sequence. In embodiments, the method includes hybridizing the complement of the primer sequence to a second immobilized oligonucleotide of the first plurality of immobilized oligonucleotides and extending the second immobilized oligonucleotide with a polymerase to form a second immobilized polynucleotide. In embodiments, the method further includes amplifying the first and second immobilized polynucleotides to form amplification products. In embodiments, the polynucleotide further includes a primer sequence, and extending the immobilized oligonucleotide includes forming a first immobilized polynucleotide including a complement of the primer sequence. In embodiments, the method includes hybridizing the complement of the primer sequence to a second immobilized primer of the first plurality of immobilized oligonucleotides, and extending the second immobilized primer with a polymerase to form a second immobilized polynucleotide. In embodiments, the method includes amplifying the first and second immobilized polynucleotides to form amplification products.

In an aspect is provided a method of making an array of nucleic acids on a surface, the method including: a) providing a solid support including a surface, the surface including a plurality of wells wherein the wells are separated from each other by interstitial regions on the surface; b) providing a plurality of particles as described herein, wherein each particle includes a plurality of bioconjugate reactive moieties; c) arraying the particles onto the surface; d) contacting the particles with a plurality of oligonucleotide moieties, wherein each oligonucleotide moiety includes a bioconjugate reactive moiety that reacts and forms a bioconjugate linker that covalently links the oligonucleotide moiety to the particle.

In another aspect is provided a method of attaching an oligonucleotide to a solid support, the method including: contacting a solid support with a particle including a degradable particle core and a polymer shell attached to the degradable particle core; wherein the polymer shell includes a plurality of first bioconjugate reactive moieties; contacting the particle with a degrading agent thereby decomposing the degradable particle core and forming a polymer composition attached to the solid support; contacting the polymer composition with a first oligonucleotide moiety including a second bioconjugate reactive moiety and covalently attaching the first oligonucleotide moiety to the polymer composition via a first bioconjugate linker, wherein the first bioconjugate linker is formed via a reaction between a first bioconjugate reactive moiety and the second bioconjugate reactive moiety. In embodiments, the method further includes contacting the polymer composition with a second oligonucleotide moiety comprising a third bioconjugate reactive moiety and covalently attaching said second oligonucleotide moiety to the polymer composition via a second bioconjugate linker, wherein the bioconjugate linker is formed via a reaction between a said first bioconjugate reactive moiety and said third bioconjugate reactive moiety. In embodiments, the method includes contacting the solid support with a plurality of particles comprising a degradable particle core and a polymer shell attached to said degradable particle core.

In embodiments, the particle is as described herein, including embodiments. In embodiments, the average longest dimension of the degradable particle core is about 100 nm to about 3000 nm. In embodiments, the degradable particle core includes a metal-organic framework (MOF) particle. In embodiments, the particle is a Zeolitic Imidazolate Framework 8 (ZIF-8) particle. In embodiments, the particle is degradable particle core is a polystyrene (PS) particle, polymethyl methacrylate (PMMA) particle, or latex particle.

In embodiments, the first oligonucleotide moiety is about 10 to about 250 nucleotides in length. In embodiments, the second oligonucleotide moiety is about 10 to about 250 nucleotides in length. In embodiments, the first oligonucleotide moiety is about 15 to about 60 nucleotides in length. In embodiments, the second oligonucleotide moiety is about 15 to about 60 nucleotides in length.

In embodiments, the solid support comprises a polymer layer. In embodiments, the polymer layer comprises polymerized units of alkoxysilyl methacrylate, alkoxysilyl acrylate, alkoxysilyl methacrylamide, alkoxysilyl methylacrylamide, or a copolymer thereof. In embodiments, the solid support comprises a resist, wherein the resist is a silsesquioxane resist, an epoxy-based polymer resist, poly(vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist.

In embodiments, the target polynucleotide is derived from a sample. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can comprise nucleic acids obtained from one or more subjects. In some embodiments, a sample comprises nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments, a subject is suspected of having a genetic variation or a disease or condition associated with a genetic variation. In embodiments, the target polynucleotide is a linear DNA molecule. In embodiments, the target polynucleotide is a circular DNA molecule.

EXAMPLES

Example 1. Controlled Deposition of Nucleic Acid Templates within Nanoarrays

Arrays (e.g., micro- and nano-arrays) are an important tool in biomedical research, providing a two-dimensional platform that arranges biological samples and enables high-throughput analyses. Delivering breakthroughs in proteomics, multiplexed immunoassays, and complex genomic analyses, microarrays can be designed to host thousands, or even up to billions, of features that can be subjected to simultaneous reaction conditions. Arrays are typically fabricated by spotting, imprinting, or directly synthesizing biomolecules on solid supports such as glasses, silicon wafers, and other functionalized substrates. In general terms, a target of interest (e.g., a protein or gene sequence) is immobilized as discrete features, or spots, on substrates, or by adopting microfabrication techniques from the semiconductor industry. In general terms, targets of interest (e.g., proteins or nucleic acids) are immobilized as discrete features on a substrate. Each feature may contain one to thousands of identical targets if subjected to an amplification technique. A successful detection event occurs when a labeled probe is brought into contact with the array, and if the probe interacts with the target, an increase of fluorescence intensity over a background level is produced, which can be measured using an appropriate detector.

Array techniques that rely on the random distribution of features typically suffer from a low ratio of incorporation event/pixel, due to a high number of dark pixels with no features (for example, if the density of features is too diffuse), or a high number of pixels that carry multiple overlapping features of different sequence (if the density of features is too concentrated) or both (due to the random nature of feature placement). An ideal and more efficient use of the imaging pixels occurs when the features on the surface are tightly packed in a patterned format, non-overlapping, and of similar size and intensity to each other. Maximizing the number of target polynucleotides per surface area will enable scientists to analyze a complex genome on one small glass chip, about 1 $cm^2$ in size.

Although the array has become a mainstay for parallel screening of several nucleic acids and proteins, it has several disadvantages. For example, microarray applications require large sample volumes and long incubation times because of the larger spot size (e.g., 1-150 m). Bead-based microarrays were developed by David Walt at Tufts University and subsequently commercialized by BeadChip products (Walt, D. R. Science 2000, 287(5452), 451-452) and others (Brenner et al. Nat. Biotechnol. 2000, 18, 630-634), however, the large diameter of the beads (e.g., 3 μm to 40 m) limit the theoretical maximum density and practical use of the underlying array. A significant reduction in particle size is necessary to achieve higher throughput, less reagent consumption, and faster data acquisitions. For context, the average diameter of a grain of sand is 60 to 2,000 m ("Relationship of Transported Particle Size to Water Velocity." 1994 Earth Science Reference Tables. Albany, N.Y.: University of the State of New York, 1994), and manipulating nanoparticles is challenging. Particles suspended in liquids are prone to form aggregates, and given the unique properties pertinent to nanoparticles, such as shape, size, surface characteristics, composition, and electronic structures, nanoparticle aggregation is more problematic than their bulk counterparts (i.e., microparticles). Further reducing the bead size to submicron dimensions, while not aggregating and retaining the necessary functional properties to form highly dense arrays, withstand repeated cycles of complex biochemical processes that result in signal generation and detection has remained a difficult task.

It has been found that particles in the sub-micron diameter (i.e., the diameter of the particle is less than or equal to about 1 m) range that include a (co)polymeric shell permeable to sequencing reaction mixtures and amplification reaction mixtures, including amplification and sequencing reagents such as oligonucleotides, and polymerases, can be dispersed into wells of an array. These particles have various compositions, for example a solid silica core surrounded by the polymeric shell. The polymeric shell includes covalently attached oligonucleotides useful for capturing next generation sequencing (NGS) library molecules that contain complementary sequences (e.g., adapter prepared library molecules). These core-shell particles make for excellent nano-reaction vessels for localized nucleic acid amplification and detection on an array. However, the particles occupy a significant fraction e.g., 25-80% of the available space of the typical nanowell. For example, a 500 nm core particle in a 700 nm well accounts for well over 50% of the available volume. Additionally, the particles can be dislodged and/or completely removed during subsequent analyses (e.g., sequencing) in an uncontrolled manner. Spontaneous removal of a particle has detrimental effects on detection. Solutions to these and other problems in the art are thus described herein.

Described herein are particles that have a degradable core that may be controllably removed from the array. For example, an array (e.g., a multiwell container) including a plurality of depressions (e.g., wells) is contacted with a particle solution. The particle solution includes a plurality of degradable-core-shell particles, wherein the core is capable of being removed and/or degraded upon contact with a suitable degrading agent (e.g., an acid such as HCl, a base such as NaOH, reducing agent, or suitable radiation) and the shell surround this degradable core includes a polymer including covalently bound polynucleotides. The shell also includes a polymer having a plurality of bioconjugate reactive moieties. The particles may be localized within each well as each well has corresponding bioconjugate reactive moieties to selectively bind the particles and particles found within the interstitial space can be selectively removed. Once the array is loaded with a sufficient quantity of particles (e.g., when greater than 80% of the available wells include a particle), a degrading agent contacts the degradable-core-shell particles and removes the particle from the well. In embodiments, the degradable-core particle is a metal organic framework (MOF) and the degrading agent is NaOH (e.g., a buffered solution including NaOH). Following removal of the degradable core, the shell polymer remains within each well. The compositions and methods described herein advantageously localize particular functional groups (e.g., bioconjugate reactive moieties and/or oligonucleotide moieties) within the wells of the array, while maintaining the interstitial spaces void of the functional groups.

Figure 1C:
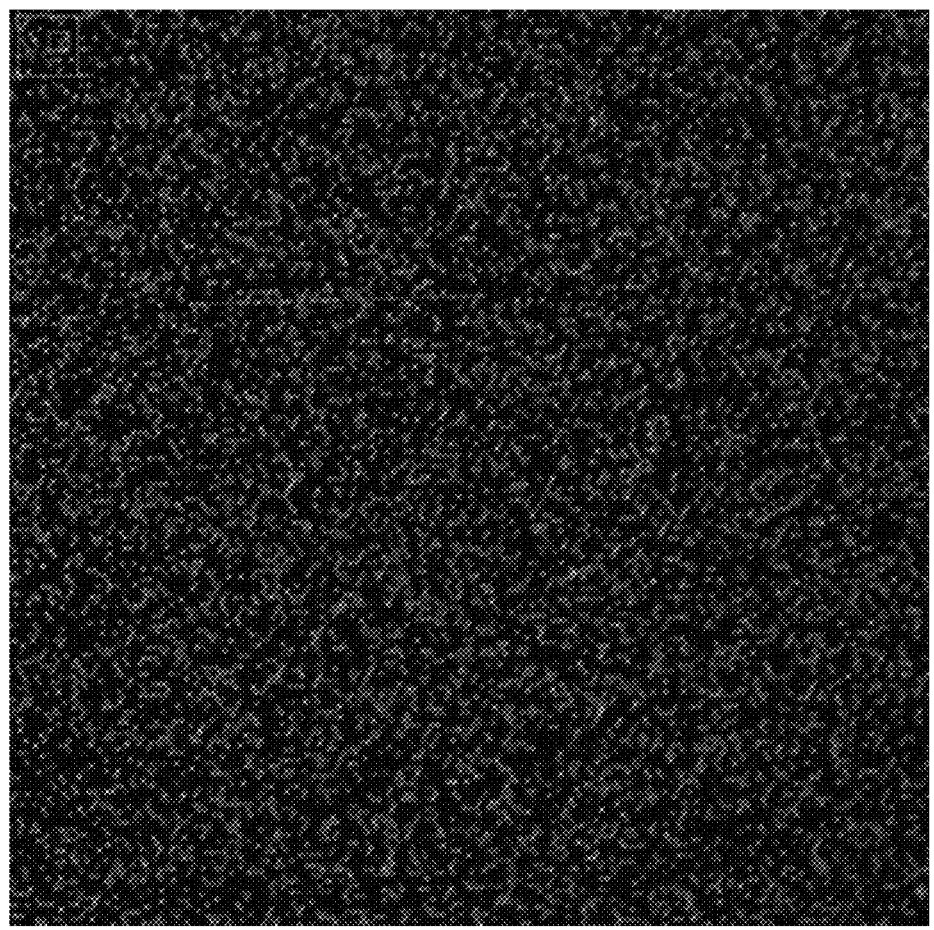

Removing the particle core while depositing the polymer in the array frees up a significant volume and provides more available surface area for key reagents (e.g., enzymes and nucleotides) to contact the polymer, relative to a traditional particle array wherein the particles remain in the wells. Additionally, controlled removal of the particle core permits higher accuracy sequencing experiments. Upon loading the particle core with a polymeric shell into the well of an array, the particle core can then be degraded, either chemically through contact with base/acid, a light mediated mechanism or through thermal means, allowing for more space in the well for cluster and amplification during sequencing. For example, FIG. 1A provides images of a patterned array containing particles loaded into the wells. Each particle is a MOF particle core with an average diameter of about 350 nm, which has a polymer shell that includes covalently attached polynucleotides. FIG. 1B provides images of the same patterned array following an alkaline (e.g., NaOH) wash which removes the particle core leaving behind in the particle-containing well only the polymer which contains immobilized polynucleotides. The polymer with immobilized nucleic acids can be bound to the wells of the array by covalent or non-covalent means. This is confirmed by hybridizing a complementary fluorescent probe as depicted as spots in FIG. 1C. The brighter spots correspond to two or more particles originally being loaded into the well, resulting in a greater amount of polynucleotides available for detection.

In embodiments, the array and associated particles including a degradable carrier core and polymeric shell as described herein address the problem of achieving a high array density with high coverage of monoclonal clusters per $cm^2$. Highly efficient loading is achieved with a pattern of high-density sites separated by a non-binding surface (e.g., interstitial space), wherein the particle type and size, preparation methods, and areas of discrete spaced apart regions are selected so that substantially all such regions contain at least one or more particle with a degradable carrier core and polymeric shell. An array that achieves high coverage of monoclonal templates is advantageous for detection and data analysis of signals collected from the arrays during sequencing analysis.

Polynucleotides on particles of the invention herein, confined to the restricted area of discrete, create punctate clusters and provide a more concentrated or intense signal, particularly when fluorescent probes are used in analytical operations, thereby providing higher signal-to-noise values and greater confidence in detection. By generating punctate clusters in an ordered array that will provide a signal, data collection is simplified and less sophisticated image analysis systems are needed to detect fewer pixels compared to traditional systems. As described supra, a benefit provided by embodiments of the array may include an increased signal intensity during sequencing-by-synthesis. The increase in signal intensity may reduce an error rate by reducing the number of clusters, for example, that emit a low intensity of light. Maintaining the interstitial spaces of the array free from non-specifically bound oligonucleotides, and subsequently amplified clusters, helps quarantine signal production to regions that have a potential broader dynamic range of signal emittance.

Examples of degradable carrier cores that can be utilized for these particles are metal-organic framework (MOF) carriers such as Zeolitic Imidazolate Framework 8 (e.g., ZIF-8), hydrophobic particles made through emulsion such as polystyrene (PS) or polymethyl methacrylate (PMMA), or latex particles. Other MOF carriers can also be utilized in these particles include UiO-66, a Zr based MOFs, mesoporous iron (III) carboxylate MIL-100(Fe) or those as described in Furukawa et al (see Science, vol. 341, No. 6149, 1230444, 2013). Any of these MOF carriers can be modified as described by Cohen (see Chem. Reviews, Vol. 112, No. 2, p. 970-1000, 2012).

The particles include a shell (e.g., a copolymeric shell including polyacrylamide (Aam), poly-N-isopropylacrylamide, poly N-isopropylpolyacrylamide, zwitterionic monomers, polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate azide (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof). In embodiments, the particle carrier is ZIF-8 and the (co)polymeric shell includes PEGMA and GMA azide. The polymeric shell is permeable to sequencing reaction mixtures and amplification reaction mixtures, including reagents, oligonucleotides, and polymerases. An advantage of the copolymer compositions provided herein is that they prevent nanoparticle aggregation.

The particles of the invention may be loaded into wells through several methods known in the art. For example, particle loading may simply be gravity driven. Gravity driven loading may also be accelerated by subsequently spinning the particles down towards the array in a centrifuge, or with an orbital mixer to increase the particle settling rate. Such combinations are optimized so that one or more particle is loaded into a given well, while achieving near complete coverage of the array with high uniformity. Additional particle loading techniques may involve agitating (e.g., vortexing), capillary assisted wetting, and/or centrifugation. In other embodiments, washing with an alkaline solution such as NaOH may be used as a post-loading cleaning technique to remove excess particle carriers. Post-cleaning may also simply consist of rinsing with a solvent, shaking, sonicating, physical removal of particles from the interstitial spaces, or a combination thereof to remove non-specifically bound particles.

The co-polymeric shell of the particle can be decorated with bioconjugate reactive moieties (e.g., where the bioconjugate reactive moiety includes an amine moiety, aldehyde moiety, alkyne moiety, azide moiety, carboxylic acid moiety, dibenzocyclooctyne (DBCO) moiety, norbornene moiety, tetrazine moiety, epoxy moiety, isocyanate moiety, furan moiety, maleimide moiety, thiol moiety, or transcyclooctene (TCO) moiety), such that either before, or after, loading the particles into a well, one or more oligonucleotide moieties may be bound to the polymeric shell. In some embodiments, the oligonucleotides moiety is about 5 to about 45 nucleotides in length. In embodiments, the oligonucleotide moiety is capable of hybridizing to a complementary sequence of a template nucleic acid. The co-polymeric shell of the particle can be decorated with immobilized (e.g., covalently bound) oligonucleotide moieties.

Figure 2D:
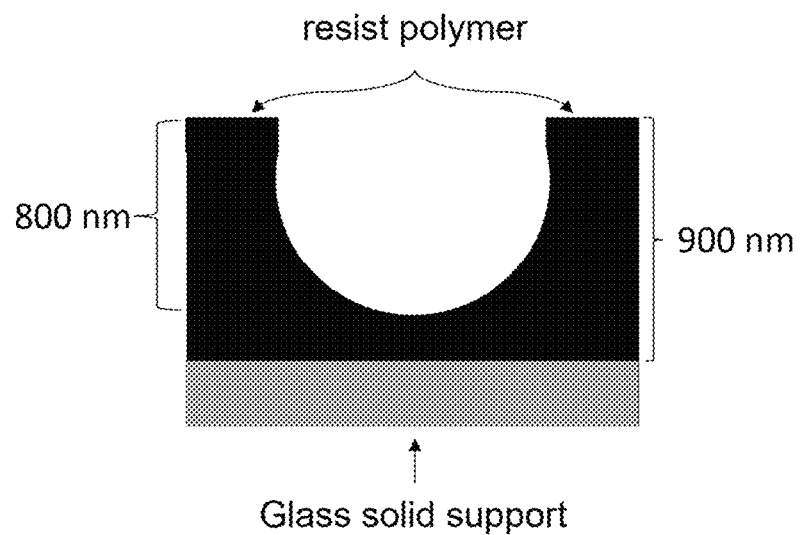

In order to obtain high coverage of monoclonal templates with minimal background, the solid support of the array may be coated with a passivating polymer (e.g., a copolymer such as a silane functionalized polyethylene glycol (Si-PEG) copolymer or a silane functionalized poly(acrylamide) (Si-Pam)). The passivating polymer may be hydrophilic or hydrophobic (e.g., polyfluorinated polymer) and may be a comb polymer or brush polymer that is useful at preventing non-specific binding of additional agents to the array (e.g., oligonucleotides in solution). Illustrations of the different well shapes of the array are depicted in FIGS. 2A-2C. Using known nanolithographic fabrication techniques, a glass substrate may be etched such that the well is anisotropic (FIG. 2A), partially anisotropic (FIG. 2B), or isotropic (FIG. 2C). The array may include a photoresist (e.g., a fluorinated polymer later) prior to receiving an additional polymer coating (e.g., a poloxamer or alkoxysilyl polymer). The photoresist may be removed prior to the addition of the additional polymer using known techniques in the art (e.g., solvent removal). In embodiments, the additional polymer coating on the array reduces the non-specific binding of oligonucleotide moieties. In other embodiments, the wells may be formed within a resist material entirely (e.g., as illustrated in FIG. 2D).

For example, by coating the array with a brush hydrophilic polymer (e.g., a random copolymer of p[PEGMA-co-TESPM]), significantly fewer detectable oligonucleotides are found in the interstitial regions following cluster amplification of hybridized template nucleic acids, compared to a control array lacking a hydrophilic polymer coating. The array may also be coated with a polymer (e.g., a random copolymer of p[PEGMA-co-HEMA-co-TMSPM] or p[PEGMA-co-HEMA]) to provide surfaces with a visible nanopattern. The arrayed particles may then be subjected to seeding with template polynucleotides. The remaining polymeric shell may then be subjected to amplification and sequencing (e.g., sequencing-by-synthesis) to determine the identity of the polynucleotide template(s) left behind by the particle in the array.

Example 2. Synthetic Materials and Methods

Figure 3A:
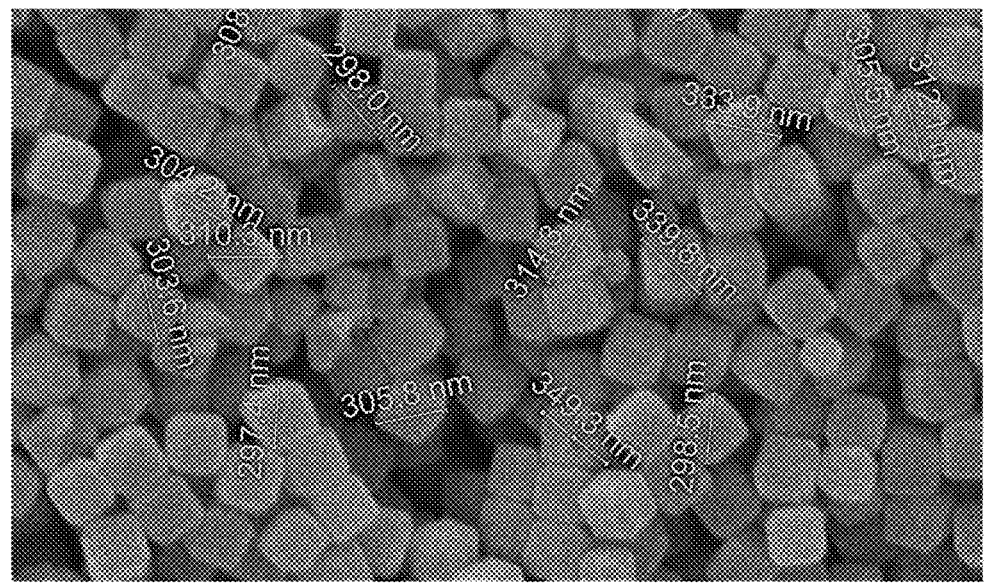
FIGS. 3A-3B provide scanning electron micrograph images of MOF particles of different sizes.
Figure 3B:
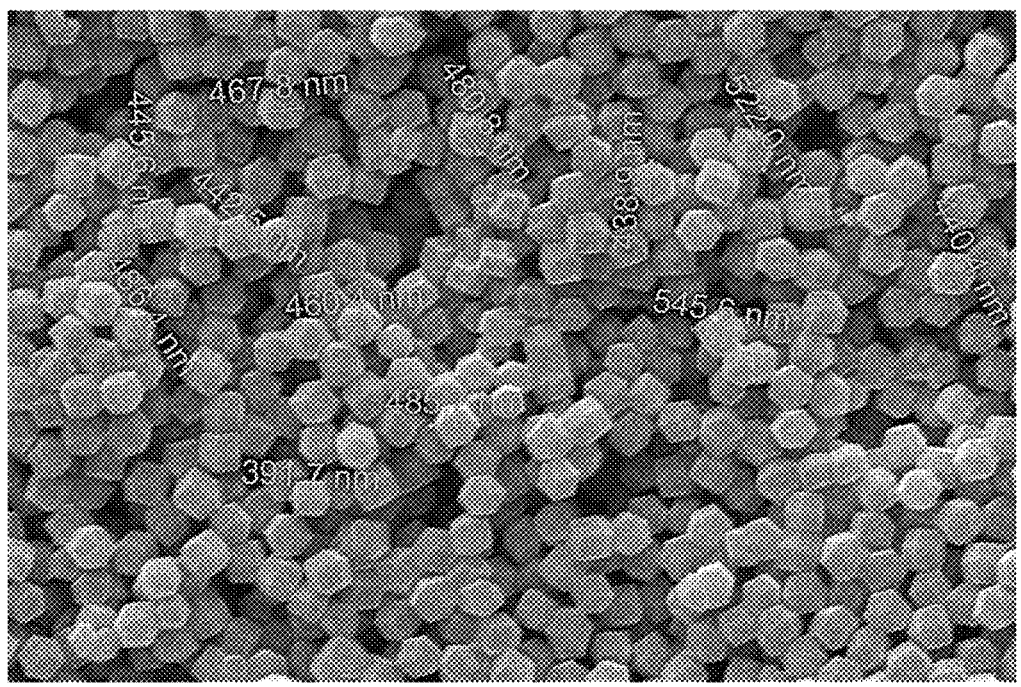

Synthesis of polymeric carrier particles useful for the methods and compositions described herein may be synthesized as follows. The MOF carrier, Zeolitic Imidazolate Framework 8 (ZIF-8), is synthesized by combining a metal salt, such as zinc, and ligand, such as 2-methylimidazole. Modulators, such as CTAB, 1-methylimidazole, sodium formate and n-butylamine, may be added to control the size of the MOF crystals as the modulator enables the MOF particles to grow larger and precipitate from solution over a longer period of time rather than immediately precipitating from solution as small amorphous particles (e.g., see FIGS. 3A and 3B providing differently sized particles). Once the ZIF-8 framework were synthesized, the 2-methylimidazole linkers are exchanged for an ATRP initiator (i.e., polymerization) such as Histamine-BiB.

Surface Initiated ATRP Particle Polymerization General Methods. The MOF particle carrier (e.g., ZIF-8 particle) was immersed in polymerization reaction mixture. This mixture depends on the type of monomers, and can include (i) solvent(s), monomer(s), initiator, and ligand or (ii) solvent(s), monomer(s) and initiator. Monomer ratios were adjusted to create polymers brushed with different spacers between neighboring side chains (ng) (i.e., determining the ratio of monomers with functional groups, e.g., azide or alkyne moieties, to monomers with non-functional groups, e.g., PEG). In embodiments, the ratio of functional groups to non-functional groups is 1:1. In embodiments, the ratio of functional groups to non-functional groups is 1:2. In embodiments, the ratio of functional groups to non-functional groups is 1:3. In embodiments, the ratio of functional groups to non-functional groups is 1:4. In embodiments, the ratio of functional groups to non-functional groups is 1:5. In embodiments, the ratio of functional groups to non-functional groups is 1:6. In embodiments, the ratio of functional groups to non-functional groups is 1:7. In embodiments, the ratio of functional groups to non-functional groups is 1:8.

Synthesis of GMA-azide. Sodium azide (NaN₃) was dissolved in deionized water and the pH of solution reduced by dropwise addition of HCl until a pH of 5.0 was reached. Approximately 30 mL of glycidyl methacrylate (GMA) was added to the sodium azide mixture via a syringe and stirred overnight to generate a mixture GMA-azides having the major and

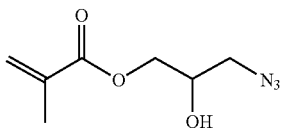

minor structures 3-azido-2-hydroxypropyl methacrylate and

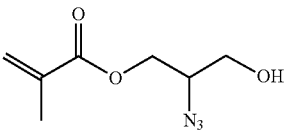

2-azido-3-hydroxypropyl methacrylate confirmed via NMR. The GMA-azide was then purified.

Synthesis of 2-(((2-azidoethoxy)carbonyl)amino) ethyl methacrylate. Starting with sodium azide (NaN₃), it was dissolved in deionized water and 30 mL of 2-bromoethanol was added via syringe. The reaction was maintained at 55° C. and stirred overnight. Approximately 25 g of 2-Isocyanatoethyl methacrylate (IEM) was added to the azido-ethanol (N₃EtOH) mixture and stirred at room temperature for 2-3 hours. A solution of dibutyltin dilaurate (DBTDL) and dichloromethane (DCM) was transferred to the IEM mixture and stirred overnight at room temperature to generate IEM-azide. The IEM-azide was then purified and confirmed via NMR to

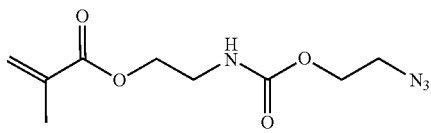 [SMILES: C=C(C)C(=O)OCCNC(=O)OCCN=[N+]=[N-]]

have the structure 2-(((2-azidoethoxy)carbonyl)amino)ethyl methacrylate

Synthesis of ZIF-8. 2-methylimidazole was dissolved in a cationic surfactant (cetyltrimethylammonium bromide (CTAB)) solution and added to a solution of Zn(Acetate)₂×2H₂O in water. The resulting solution was stirred and left at room temperature until particles precipitated from solution. These particles were centrifuged (e.g., 9000 rmp for 10 min) and washed with methanol (e.g., 3×40 mL methanol). His-BIB was dissolved in BuOH and added to a solution of ZIF-8 particles dispersed in BuOH and stirred. The resulting particles were centrifuged (e.g., 9000 rmp for 10 min) and washed with ethanol (e.g., 3×40 mL methanol). The ratio of his-Bib to 2-methylimidazole may be tuned to confine the functionalization to the surface of the particle. For example, the ratio of 2-methylimidazole is his-Bib to 1:2 permits surface functionalization Spherical ZIF-8. In a 1L glass vessel, 3.65g zinc acetate dihydrate was dissolved in 250 mL of MeOH. A second vessel was created including 4.0 g 2-methylimidazole, and 2.5 g of 1-methylimidazole was dissolved in MeOH. The two solutions were mixed together rapidly and allowed to sit at RT overnight to result in substantially spherical ZIF-8 particles averaging about 460 nm in diameter.

Cubic ZIF-8. A first solution include 1.5 g zinc acetate dihydrate was dissolved in water. A second solution including 4.3 g of 2-methylimidazole was dissolved in 0.5 mM CTAB aqueous solution. The solutions were mixed and allowed to sit at RT for 4 hours, resulting in substantially cubic ZIF-8 particles averaging about 410 nm in diameter.

Polymerization of ZIF-8 Particles. Through a column of basic alumina, PEGMA₅₀₀, Mn=500 was passed through to remove BHT inhibitor. The purified PEGMA₅₀₀ was added to ATRP-initiator functionalized ZIF-8 particles in ethanol in a flask and sonicated until the particles are dispersed. GMA-Azide, 2-hydroxyethyl 2-bromoisobutyrate (OH-EBiB), CuBr₂, 1,1,4,7,10,10-Hexamethyltriethylenetetramine (HMTETA) was then added to the reaction flask. Copper(I) bromide (CuBr) is added to the reaction flask and the flask was heated to 60° C. The reaction mixture was rinsed, centrifuged, and the supernatant is removed. Fresh ethanol was added to the particles, and this solution is vortex and sonicated several times. The supernatant was removed to provide polymerized ZIF-8 particles that were examined under microscope.

Addition of Oligonucleotide Primers to Polymerized ZIF-8 Particles. In a reactor containing ethanol/buffer solution oligonucleotide primers (e.g., S1 and S2 primer oligonucleotides) were added. To this same reactor, polymerized ZIF-8 particles were added and the mixture was sonicated and stirred overnight. The resulting polymerized ZIF-8 particles with oligonucleotide primers were spun down and washed before being dispersed in an ethanol/salt solution. Following sonication, the particles were stored in solution.

A solution of polymer in toluene was poured into a glass reaction vessel and a patterned glass slide was then added to this vessel. The reaction vessel was placed in a desiccator and sealed for 15-18 hrs. The slides were removed and placed into a container containing toluene and sonicated for 6 min. The slides were then removed and placed into another container containing toluene, sonicated 6 min and then placed into a container containing ethanol and sonicated 6 min. The polymerized slides were then dried and stored under N₂.

Particle Loading. The following are examples of general particle loading techniques. Polymerized ZIF-8 particles (i.e., core-shell particles, as described herein) were dispersed in ethanol and sonicated. This solution was added to a patterned surface slide. The slide and particle solution were incubated overnight. Following this incubation period, the slides were washed with ethanol, dried, and wiped to remove any interstitial particles (i.e., particles not confined to a well). To check the quantity of synthesized particles deposited onto the polymerized surface slides, phase contrast microscopy was performed on the slides. Alternatively, the slide and particle solution may be centrifuged to allow deposition of the particles onto the patterned slide. For example, the polymerized ZIF-8 particles were suspended in $H_2O$ and sonicated for about 30 minutes to separate any aggregates. The colloidal solution was applied to a patterned slide (i.e., a slide with a plurality of wells) such that about $2.0 \times 10^9$ to $3.0 \times 10^9$ particles per channel were deposited via a customized centrifugal device, wherein excess solvent is spun off. The slides were then repeatedly contacted with surfactant (e.g., polyoxyethylene sorbitol ester, such as Tween 20) and the excess was wiped off, followed by repeatedly contacting the slide with water and wiping off the excess with lens paper. It is advantageous to allow water to remain within the wells until further use. Polishing the excess particles not deposited in wells aids in providing bioconjugate reactive moieties and/or oligonucleotides only within the wells.

Polymerized ZIF-8 particles with oligonucleotide primers in loading solution (TE buffer with NaCl which may optionally contain ethanol) were sonicated. Following sonication, the particles in solution were added to a tray containing patterned glass slide(s) containing a photoresist and shaken for 10 min. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly(vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276). Typical photoresists coat the solid support surface, but not the surface of the wells. In embodiments, the photoresist is an organically modified ceramic polymer (ORMOCER®, registered trademark of Fraunhofer-Gesellschaft zur Forderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference. Following shaking, the tray was placed at 4° C. The slides were dried, washed, and dried again. The slides were examined under microscope to check the quantity of polymerized ZIF-8 particles with oligonucleotide primers particles deposited on the slides.

Digestion of Polymer Carrier Core. The polymer carrier core can be digested through addition of an alkaline (i.e., base) solution such as NaOH. A slide containing polymerized ZIF-8 particles, optionally with oligonucleotide primers, was immersed in a 1M NaOH alkaline solution and shaken. Alternatively, the slide may be immersed in a 0.5M HCl acid solution and shaken. The slide was then placed into a water solution and shaken to wash away any residual salts. This slide was placed into water, fresh ethanol, shaken, dried and wiped in the presence of water. The slide may then be assembled into a flow cell for use in subsequent sequencing experiments.

The deposition procedure described above was repeated on a patterned support including a plurality of wells, each well separated from each other by about 1.4 µm, wherein each well is about 0.7 µm in diameter. The deposition procedure described above was repeated on a patterned support including a plurality of wells, each well separated from each other by about 1.0 µm, wherein each well is about 0.5 µm in diameter.

Example 3. Particle Use in Clustering and Sequencing

Quality control experiments were performed using materials and methods as described above. Particles without ZIF-8 as a polymer carrier core having template polynucleotides and particles with ZIF-8 as a polymer carrier core, both with and without a subsequent base wash, having template polynucleotides were subject to clustering and sequencing conditions. All the particles, those without ZIF-8 as a polymer carrier, those that had ZIF-8 as a polymer carrier which was subsequently removed with a basic wash (i.e., a degrading agent with an alkaline pH) and those with ZIF-8 as a polymer carrier that was not removed showed similar amplification of the polynucleotide template. Sequencing of samples of *Salmonella* library also showed 99.9% accuracy using all the various particles.

Figure 5:
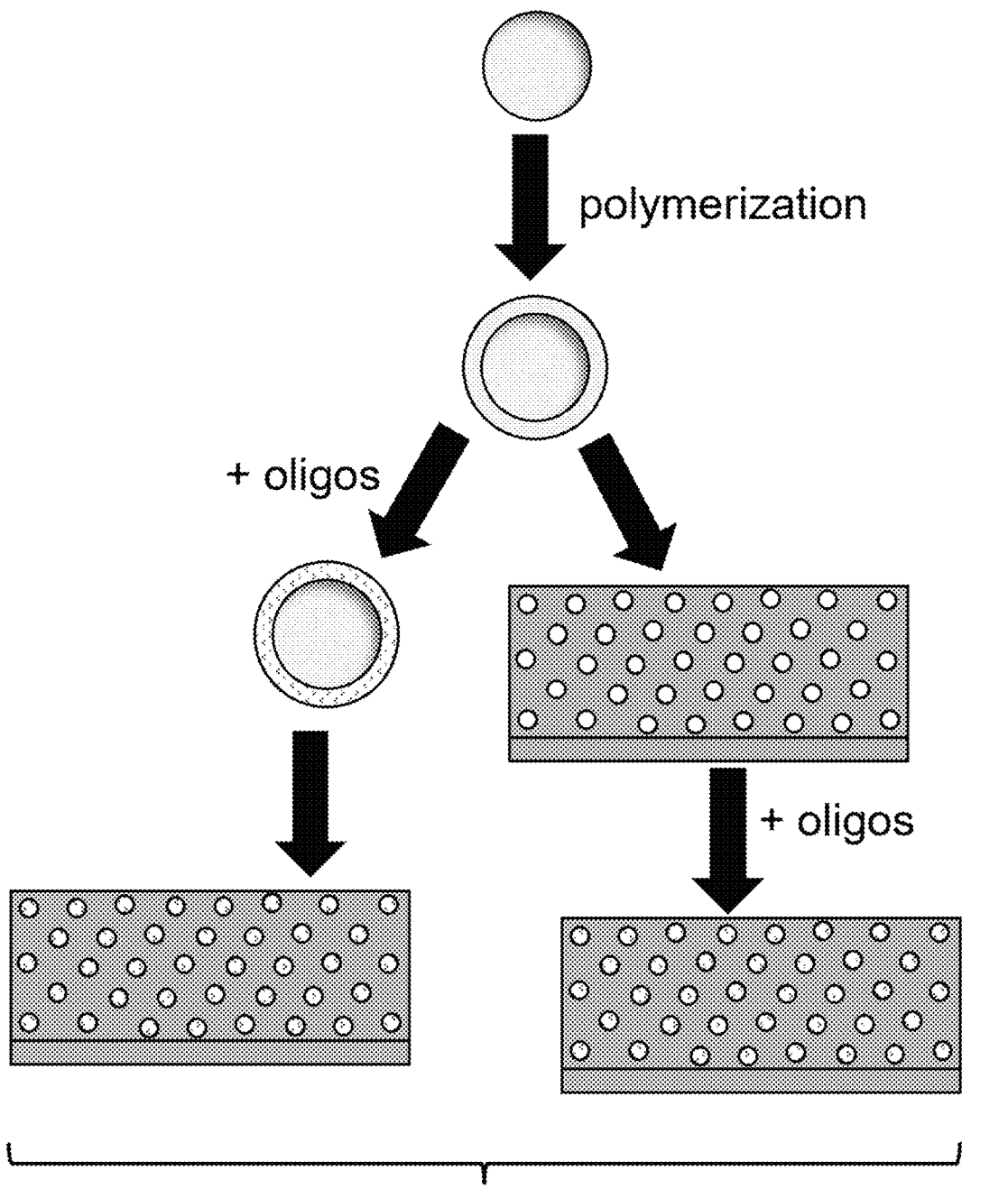
FIG. 5. An overview of the polymerization and particle loading is provided in FIG. 5. A degradable particle core is incubated with monomers under suitable polymerization conditions coats the core with a polymer shell (e.g., a copolymer as described herein). The functionalized particle now includes a plurality of bioconjugate reactive moieties (e.g., azido moieties). The functionalized particle may be loaded onto a patterned solid support (e.g., a multiwell container that optionally includes a passivating polymer as described herein) and arranged into the wells, as illustrated on the right path. Oligonucleotide moieties containing a reactive bioconjugate moiety (e.g., a DBCO moiety) are allowed to contact the particles, wherein the oligonucleotides reacts with the bioconjugate groups on the polymers and forms a polymeric bioconjugate linker, thereby covalently immobilizing the oligonucleotides to the particle. Alternatively, prior to loading into the patterned solid support, oligonucleotide moieties containing a reactive bioconjugate moiety are allowed to contact the particles and form a bioconjugate linker (left path), thereby covalently immobilizing the oligonucleotides to the particle. The oligo-containing particles are then loaded onto the multiwell container that does not include a passivating polymer. A particle loaded patterned flow cell may include about 10,000 to about 50,000, or about 25,000 immobilized oligonucleotides per square micrometer. The pattered solid support is then ready for storage, clustering (e.g., template seeding and amplification), and/or sequencing.

Alternative experiments using an acidic degrading agent were found to also be successful at depositing the polymer within the well, amplifying, and sequencing. Briefly, the polymer-coated particles are deposited into the wells according to the procedure identified supra. To minimize any potential damage to the oligonucleotides, the polymer shell included bioconjugate reactive moieties during slide deposition (e.g., the right path of FIG. 5, as illustrated in FIG. 7). Following deposition, two populations of primers (i.e., 11 µM of primer 1 and 11 µM of primer 2) were incubated overnight at 37° C. and allowed to contact and react with the bioconjugate reactive moieties present in the polymer shell. The primers may be referred to as platform primer sequences, which are used during subsequent amplification reactions (e.g., solid phase amplification) following capture of a target polynucleotide.

In embodiments, each of platform primers (e.g., immobilized platform primers) is about 12 to about 50 nucleotides in length. In embodiments, each of the platform primers (e.g., immobilized platform primers) is about 5 to about 25 nucleotides in length. In embodiments, each of the platform primers (e.g., immobilized platform primers) is about 10 to about 40 nucleotides in length. In embodiments, each of the platform primers (e.g., immobilized platform primers) is about 5 to about 100 nucleotides in length. In embodiments, each of the platform primers (e.g., immobilized platform primers) is about 20 to 200 nucleotides in length. In embodiments, each of the platform primers (e.g., immobilized platform primers) about or at least about 5, 6, 7, 8, 9, 10, 12, 15, 18, 20, 25, 30, 35, 40, 50 or more nucleotides in length.

What is claimed is:

1. A method of sequencing a target polynucleotide, said method comprising:
   (i) contacting a solid support comprising a plurality of particles with a degrading agent and decomposing said particles thereby forming a polymer film attached to solid support, wherein each particle comprises a degradable particle core and a polymer shell attached to said particle core, wherein said polymer shell comprises a first bioconjugate reactive moiety;

(ii) contacting said polymer film with an oligonucleotide comprising a second bioconjugate reactive moiety and binding said oligonucleotide to the polymer film;

(iii) hybridizing a target polynucleotide to said oligonucleotide and extending said oligonucleotide with a polymerase to form a complement of the target polynucleotide; and (iv) sequencing said complement of the target polynucleotide.

2. The method of claim 1, wherein said solid support comprises a plurality of wells.

3. The method of claim 2, wherein said plurality of wells comprises one or more particles.

4. The method of claim 2, wherein one or more particles are attached to a surface inside a well, and one or more particles are attached to a surface outside a well.

5. The method of claim 4, further comprising removing the one or more particles attached to the surface outside a well prior to step (i).

6. The method of claim 5, wherein removing comprises polishing the solid support with a cleaning article.

7. The method of claim 1, wherein the solid support comprises about $1 \times 10^5$ to about $5 \times 10^{10}$ wells.

8. The method of claim 2, wherein the wells are separated from each other by about 0.5 μm to about 2.0 μm.

9. The method of claim 2, wherein the wells are separated from each other by about 0.7 μm to about 1.5 μm.

10. The method of claim 2, wherein the wells are from about 0.2 μm to about 2 μm in diameter, and wherein the wells are about 0.5 μm to about 2 μm in depth.

11. The method of claim 1, further comprising amplifying said complement of the target polynucleotide.

12. The method of claim 11, wherein amplifying comprises of rolling circle amplification (RCA), exponential rolling circle amplification (eRCA), recombinase polymerase amplification (RPA), helicase dependent amplification (HDA), or template walking amplification.

13. The method of claim 11, wherein amplifying comprises thermal bridge polymerase chain reaction (t-bPCR) amplification, chemical bridge polymerase chain reaction (c-bPCR) amplification, or chemical-thermal bridge polymerase chain reaction (cT-bPCR) amplification).

14. The method of claim 1, wherein sequencing comprises sequencing by synthesis, sequencing by binding, sequencing by ligation, or pyrosequencing.

15. The method of claim 1, wherein sequencing comprises hybridizing a sequencing primer to the target polynucleotide, or a complement thereof, and incorporating one or more nucleotides into the sequencing primer with a polymerase to create an extension strand; and detecting the one or more incorporated nucleotides.

16. The method of claim 2, wherein the solid support comprises polymerized units of alkoxysilyl methacrylate, alkoxysilyl acrylate, alkoxysilyl methylacrylamide, alkoxysilyl acrylamide, or a copolymer thereof.

17. The method of claim 2, wherein the solid support comprises a resist, wherein the resist is a silsesquioxane resist, an epoxy-based polymer resist, poly(vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist.

18. The method of claim 1, wherein said degradable particle core is a metal-organic framework (MOF) core.

19. The method of claim 18, wherein said MOF core is a Isoreticular Metal-Organic Framework (IR-MOF) core, Zeolitic Imidazolate Framework (ZIF) core, Porous Coordination Network (PCN) core, Materials Institute Lavoisier (MIL) MOF core, Porous Coordination Polymer (PCP) core, or University of Oslo (UiO) MOF core.

20. The method of claim 18, wherein said MOF core is a Zeolitic Imidazolate Framework 8 (ZIF-8) core or a UiO-66 MOF core.

21. The method of claim 1, wherein the polymer shell comprises polyacrylamide (AAm), poly(N-(5-azidoacetamidylpentyl)acrylamide-co-acrylamide (PAZAM), poly-N-isopropylacrylamide, poly N-isopropylpolyacrylamide, polyethylene glycol acrylate, methacrylate, polyacrylic acid, poly(hydroxyethyl methacrylate) (PHEMA), poly(methyl methacrylate) (PMMA), poly(N-isopropylacrylamide) (PNIPAAm), glicydyl methacrylate (GMA), glicydyl methacrylate (GMA) azide, hydroxyethylimethacrylate (HEMA), hydroxyethylacrylate (HEA), hydroxypropylmethacrylate (HPMA), polyethylene glycol methadrylate (PEGMA), polyethylene glycol acrylate (PEGA), isocyanatoethyl methacrylate (IEM), or a copolymer thereof.

22. The method of claim 1, wherein said degrading agent is a 0.1 to 1.0 M solution of an acid or a 0.1 to 1.0 M solution of a base.

23. The method of claim 1, wherein said degrading agent comprises NaOH.

24. A method of sequencing a target polynucleotide, said method comprising:

(i) contacting a solid support comprising a plurality of particles with a degrading agent and decomposing said particles thereby forming a polymer film attached to solid support, wherein each particle comprises a degradable particle core and a polymer shell attached to said particle core, wherein said polymer shell comprises an oligonucleotide moiety covalently attached to said polymer shell;

(ii) hybridizing a target polynucleotide to said oligonucleotide moiety and extending said oligonucleotide with a polymerase to form a complement of the target polynucleotide; and (iii) sequencing said complement of the target polynucleotide.

25. The method of claim 24, wherein said solid support comprises a plurality of wells.

26. The method of claim 25, wherein one or more particles are attached to a surface inside a well, and one or more particles are attached to a surface outside a well.

27. The method of claim 26, further comprising removing the one or more particles attached to the surface outside a well prior to step (i).

28. The method of claim 27, wherein removing comprises polishing the solid support with a cleaning article.

29. The method of claim 24, wherein the solid support comprises about $1 \times 10^5$ to about $5 \times 10^{10}$ wells.

30. The method of claim 24, wherein said degradable particle core is a metal-organic framework (MOF) core.

* * * * *